US006825012B2

(12) United States Patent
Blanche et al.

(10) Patent No.: US 6,825,012 B2
(45) Date of Patent: *Nov. 30, 2004

(54) DNA MOLECULES, PREPARATION AND USE IN GENE THERAPY

(75) Inventors: Francis Blanche, Paris (FR); Béatrice Cameron, Paris (FR)

(73) Assignee: Gencell S.A. (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/981,803

(22) Filed: Oct. 19, 2001

(65) Prior Publication Data

US 2003/0032092 A1 Feb. 13, 2003

Related U.S. Application Data

(60) Continuation-in-part of application No. 09/655,728, filed on Sep. 5, 2000, now Pat. No. 6,492,164, which is a division of application No. 08/894,511, filed as application No. PCT/FR96/00274 on Feb. 21, 1996, now Pat. No. 6,143,530.

(30) Foreign Application Priority Data

Feb. 23, 1995 (WO) ............................... PCT/FR95/02117

(51) Int. Cl.$^7$ ............................. C12N 1/21; C12N 5/10; C12N 15/64; C12N 15/70; C12N 15/79
(52) U.S. Cl. .................. 435/91.42; 435/91.1; 435/91.4; 435/455; 435/320.1; 435/325; 435/252.33; 435/254.11
(58) Field of Search ............................... 435/91.1, 91.2, 435/91.4, 455, 320.1, 325, 252.33, 254.11, 91.42

(56) References Cited

U.S. PATENT DOCUMENTS

| | | | |
|---|---|---|---|
| 5,028,530 A | | 7/1991 | Lai et al. .................... 435/69.1 |
| 5,227,288 A | | 7/1993 | Blattner .......................... 435/6 |
| 5,401,632 A | | 3/1995 | Wang et al. ..................... 435/6 |
| 6,143,530 A | * | 11/2000 | Crouzet et al. ........... 435/91.42 |
| 6,492,164 B1 | * | 12/2002 | Crouzet et al. .......... 435/320.1 |

FOREIGN PATENT DOCUMENTS

| | | |
|---|---|---|
| EP | 0 160 571 A2 * | 11/1985 |
| EP | 300 422 | 1/1989 |
| EP | 350 341 | 1/1990 |
| WO | WO 94/09127 | 4/1994 |
| WO | WO 96/05297 | 2/1996 |

OTHER PUBLICATIONS

Black, L.W., "In vitro packaging into phage T4 particles and recircularization of phage lambda DNAs," Gene 46: 97–101, 1986.*

Peredelchuk et al., "A method for construction of E. coli strains with multiple DNA insertions," Gene 187 (2): 231–238, Mar. 18, 1997.*

Takabatake et al., The use of purine–rich oligonucleotides in triplex–mediated DNA isolation and generation of unidirectional deletions, Nucleic Acids Res., vol. 20, pp. 5853–5854 (1992).

Ito et al., Sequence–specific DNA purification by triplex affinity capture, Proc. Natl. Acad. Sci. USA, vol. 89, pp. 495–498 (1992).

Mizuuchi et al., The extent of DNA sequence required for a functional bacterial attachment site of phage lambda, Nucleic Acids Res., vol. 13, pp. 1193–1208 (1985).

Hasan et al., Control of cloned gene expression by promoter inversion in vivo: construction of improved vectors with a multiple cloning site and the ptac promoter, Gene, vol. 56, pp. 145–151 (1987).

Su et al., Selective binding of Escherichia coli RNA polymerase to topoisomers of minicircles carrying the TAC16 and TAC17 promoters, J. Biol. Chem., vol. 269, pp. 13511–13521 (1994).

Backman et al., Use of synchronous site–specific recombination in vivo to regulate gene expression, Biotechnology, vol. 2, pp. 1045–1049 (1984).

Eberl et al., Analysis of the multimer resolution system encoded by the parCBA operon of broad–host–range plasmid RP4, Molecular Microbiology, vol. 12, pp. 131–141 (1994).

Stark et al., Catalysis by site–specific recombinases, Trends in Genetics, vol. 8, pp. 432–439 (1992).

Orkin et al., Report and recommendations of the panel to assess the NIH investment in research on gene therapy, issued by the U.S. National Institutes of Health, (1995).

Ben–Yedidia et al., Design of peptide and polypeptide vaccines, Curr. Opin. Biotechnol., vol. 8, pp. 442–448 (1997).

Bigger et al., An araC–controlled bacterial cre expression system to produce DNA minicircle vectors for nuclear and mitochondrial gene therapy, J. Biol. Chem., vol. 276, pp. 23018–23027 (2001).

Sambrook et al., Molecular cloning—a laboratory manual, Cold Spring Harbor Laboratory Press, vol. 3, Chapter 15, 15.1–15.4 (2000).

Guzman et al., Tight regulation, modulation, and high–level expression by vectors containing the arabinose $P_{BAD}$ promoter, J. Bacteriol., vol. 177, No. 14, pp. 4121–4130 (1995).

* cited by examiner

Primary Examiner—Scott D. Priebe
(74) Attorney, Agent, or Firm—Finnegan, Henderson, Farabow, Garrett & Dunner, L.L.P.

(57) ABSTRACT

The invention provides double-stranded circular DNA molecules having one or more genes of interest, but lacking an origin of replication and a selectable marker, and methods for making such molecules.

30 Claims, 27 Drawing Sheets

1 →
2 →
3 →
4 →
5 →
6 →

C14018: 5'-AAAGGCGCCAGCTTAAAAAAAATCC-3' (SEQ ID NO: 49)
7904: 5'-CATACGTCATTATTGACGTC-3' (SEQ ID NO: 50)

TRIPLE HELIX SEQUENCE & attL (119 bp) (SEQ ID NO: 12)

5'-<u>TTCTTTTTTTTCTT</u>GAAGCCTGCTTTTTTATACTAAGTTGGCATTATAAAAAAGCATTGC-3'
3'-<u>AAGAAAAAAAAGAA</u>CTTCGGACGAAAAAATATGATTCAACCGTAATATTTTTTCGTAACG-5'

5'-TTATCAATTTGTTGCAACGAACAGGTCACTATCAGTCAAAATAAAATCATTATTTGATT-3'
3'-AATAGTTAAACAACGTTGCTTGTCCAGTGATAGTCAGTTTTATTTTAGTAATAAACTAA-5'

← pXL3909 non-recombined

← Miniplasmid MP3909

TH et attB (29bp) (SEQ ID NO:13)

5'-TTCTTTTTTTTCTTGAAGCCTGCTTTTTTATACTAACTTGAGC-3'

3'-AAGAAAAAAAGAACTTCGGACGAAAAAATATGATTGAACTCG-5'

Figure 24
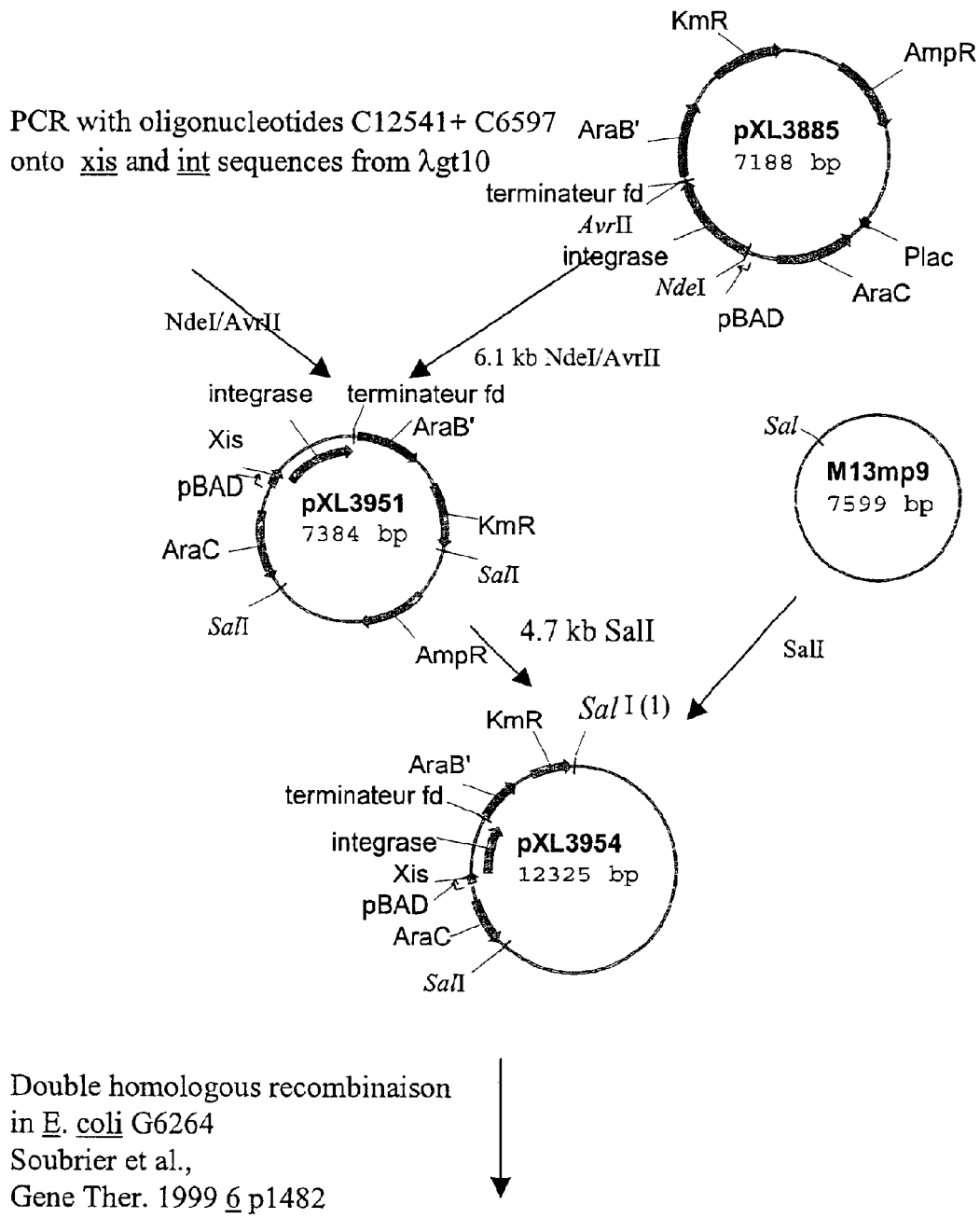
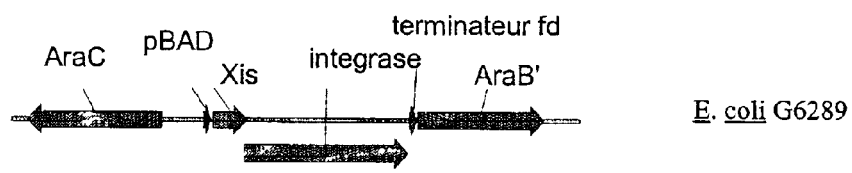
Excisionase & Integrase expressed under control of pBAD

Figure 26
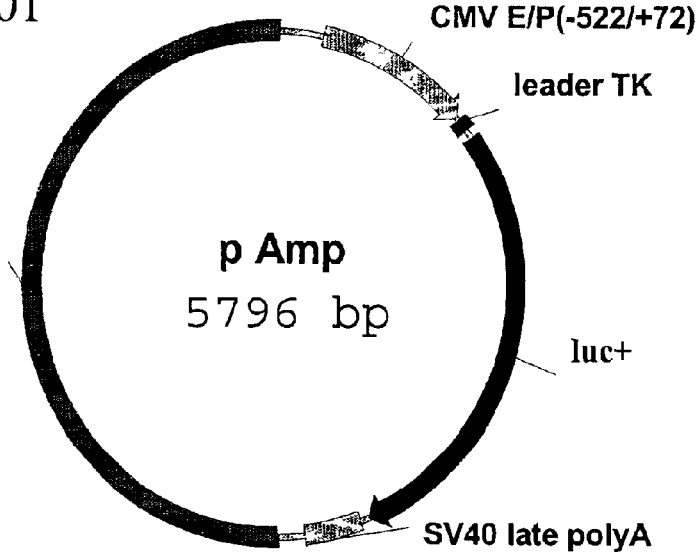
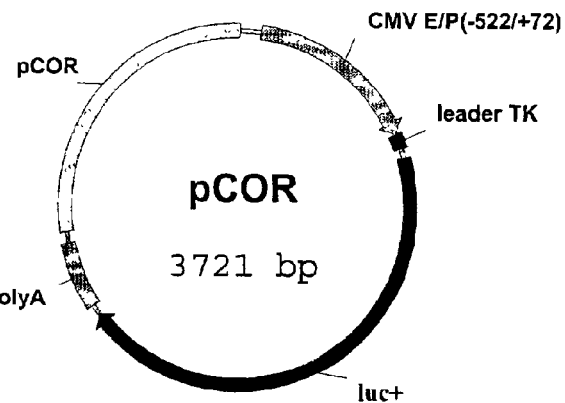
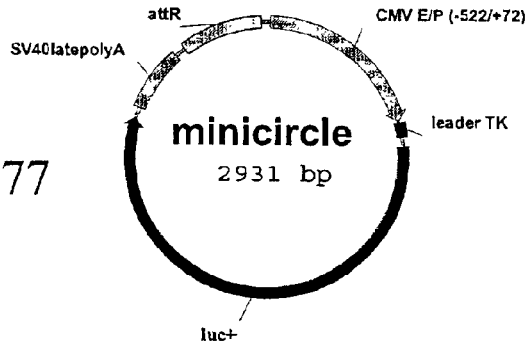

DNA MOLECULES, PREPARATION AND USE IN GENE THERAPY

This application is a continuation-in-part of U.S. patent application Ser. No. 09/655,728, filed Sep. 5, 2000, now U.S. Pat. No. 6,492,164, which was a division of U.S. patent application Ser. No. 08/894,511, filed Aug. 19, 1997, now U.S. Pat. No. 6,143,530, which was the national stage application of PCT/FR96/00274 (not published in English), filed Feb. 21, 1996, all of which are incorporated by reference herein.

Gene therapy consists in correcting a deficiency or an abnormality by introducing genetic information into the affected cell or organ. This information may be introduced either in vitro into a cell extracted from the organ and then reinjected into the body, or in vivo, directly into the tissue concerned. Being a high molecular weight, negatively charged molecule, DNA has difficulties in passing spontaneously through the phospholipid cell membranes. Different vectors are hence used in order to permit gene transfer: viral vectors on the one hand, natural or synthetic, chemical and/or biochemical vectors on the other hand. Viral vectors (retroviruses, adenoviruses, adeno-associated viruses, etc.) are very effective, in particular, in passing through membranes, but present a number of risks, such as pathogenicity, recombination, replication, immunogenicity, etc.

Chemical and/or biochemical vectors enable these risks to be avoided (for reviews, see Behr et al., Acc.Chem Res., 26, 274–278 (1993), Cotton et al., Curr. Biol., 4:705–710, 1993). These vectors are, for example, cations (calcium phosphate, DEAE-dextran, etc.) which act by forming precipitates with DNA. These precipitates can be "phagocytosed" by the cells. These vectors can also be liposomes in which DNA is incorporated and which fuse with the plasma membrane. Synthetic gene transfer vectors are generally lipids or cationic polymers that complex DNA and form a particle therewith carrying positive surface charges. These particles are capable of interacting with the negative charges of the cell membrane and then of crossing the latter. Dioctadecylamidoglycylspermine (DOGS, Transfectam™) or N-[1-(2,3-dioleyloxy)propyl]-N,N,N-trimethylammonium chloride (DOTMA, Lipofectin™) may be mentioned as examples of such vectors. Chimeric proteins have also been developed: they consist of a polycationic portion which condenses DNA, linked to a ligand which binds to a membrane receptor and carries the complex into the cells by endocytosis. It is thus theoretically possible to "target" a tissue or certain cell populations so as to improve the in vivo bioavailability of the transferred gene.

However, the use of chemical and/or biochemical vectors or of naked DNA implies the possibility of producing large amounts of DNA of pharmacological purity. In effect, in these gene therapy techniques, the medicinal product consists of the DNA itself, and it is essential to be able to manufacture, in appropriate amounts, DNAs having suitable properties for therapeutic use in man.

The plasmids currently used in gene therapy carry (i) an origin of replication, (ii) a selection marker gene such as a gene for resistance to an antibiotic (kanamycin, ampicillin, etc.) and (iii) one or more transgenes with sequences required for their expression (enhancer(s), promoter(s), polyadenylation sequences, etc.). These plasmids currently used in gene therapy (in clinical trials such as the treatment of melanomas, Nabel et al., Human Gene Therapy, 3:399–410, 1992, or in experimental studies) display, however, some drawbacks associated, in particular, with their dissemination in the body. Thus, as a result of this dissemination, a competent bacterium present in the body can, at a low frequency, receive this plasmid. The chance of this occurring is all the greater for the fact that the treatment in question entails in vivo gene therapy in which the DNA may be disseminated in the patient's body and may come into contact with bacteria which infect this patient or alternatively with bacteria of the commensal flora. If the bacterium which is a recipient of the plasmid is an enterobacterium such as E. coli, this plasmid may replicate. Such an event then leads to the dissemination of the therapeutic gene. Inasmuch as the therapeutic genes used in gene therapy treatments can code, for example, for a lymphokine, a growth factor, an anti-oncogene, or a protein whose function is lacking in the host and hence enables a genetic defect to be corrected, the dissemination of some of these genes could have unforeseeable and worrying effects (for example, if a pathogenic bacterium were to acquire the gene for a human growth factor).

Furthermore, the plasmids used in non-viral gene therapy also possess a marker for resistance to an antibiotic (ampicillin, kanamycin, etc.). Hence the bacterium acquiring such a plasmid has an undeniable selective advantage, since any therapeutic antibiotic treatment using an antibiotic of the same family as the one selecting the resistance gene of the plasmid will lead to the selection of the plasmid in question. In this connection, ampicillin belongs to the β-lactams, which is the family of antibiotics most widely used in the world.

It is hence necessary to seek to limit as far as possible the dissemination of the therapeutic genes and the resistance genes. Moreover, the genes carried by the plasmid, corresponding to the vector portion of the plasmid (function(s) required for replication, resistance gene), also run the risk of being expressed in the transfected cells. There is, in effect, a transcription background, which cannot be ruled out, due to the host's expression signals on the plasmid. This expression of exogenous proteins may be thoroughly detrimental in a number of gene therapy treatments, as a result of their potential immunogenicity and hence of the attack of the transfected cells by the immune system. In addition, immunostimulatory DNA sequences present in the plasmid backbone have been shown to trigger immune responses (Sato et al., 1996 Science 273: 352–354).

Hence, it is especially important to be able to have at one's disposal medicinal DNA molecules having a genetic purity suitable for therapeutic use. It also is especially important to have at one's disposal methods enabling these DNA molecules to be prepared in amounts appropriate for pharmaceutical use. The present invention provides a solution to these problems.

The present invention describes, in effect, DNA molecules that can be used in gene therapy, having greatly improved genetic purity and impressive properties of bioavailability. The invention also describes especially effective methods for the preparation of these molecules and for their purification.

The present invention lies, in particular, in the development of DNA molecules which can be used in gene therapy, virtually lacking any non-therapeutic region. The DNA molecules according to the invention, also designated minicircles on account of their circular structure, their small size, and their supercoiled form, display many advantages.

They make it possible, in the first place, to eliminate the risks associated with dissemination of the plasmid, such as (1) replication and dissemination which may lead to an uncontrolled overexpression of the therapeutic gene, (2) the dissemination and expression of resistance genes, and (3) the expression of genes present in the non-therapeutic portion of the plasmid, which are potentially immunogenic and/or inflammatory, and the like and (4) presence of immunostimulatory sequences. The genetic information contained in the DNA molecules according to the invention is limited, in effect, essentially to the therapeutic gene(s) and to the signals for regulation of its/their expression (neither origin of replication nor gene for resistance to an antibiotic or the like). The probability of these molecules (and hence of the genetic information they contain) being transferred to a microorganism and being stably maintained is almost zero.

Furthermore, due to their small size, DNA molecules according to the invention potentially have better bioavailability in vivo. In particular, they display improved capacities for cell penetration and cellular distribution. Thus, it is recognized that the coefficient of diffusion in the tissues is inversely proportional to the molecular weight (Jain, Cancer Res. 47: 3039–3051, 1987). Similarly, at the cellular level, high molecular weight molecules have inferior permeability through the plasma membrane. In addition, for the plasmid to enter the nucleus, which is essential for the expression of a transgene, high molecular weight also is a drawback, the nuclear pores imposing a size limit for diffusion into the nucleus (Landford et al., Cell 46: 575–582, 1986). The elimination of the non-therapeutic portions of the plasmid (in particular, the origin of replication and selectable marker gene) according to the invention also enables the size of the DNA molecules to be decreased. This decrease may be estimated at a factor of 2, recloning, for example, 3 kb for the origin of replication and the selectable marker (vector portion) and 3 kb for the transgene with the sequences required for its expression. This decrease (i) in molecular weight and (ii) in negative charge endows the molecules of the invention with improved capacities for tissue, cellular, and nuclear diffusion and bioavailability.

Hence, a first subject of the invention lies in a double-stranded DNA molecule having the following features: it is circular in shape and comprises one or more genes of interest. As stated above, the molecules of the invention essentially lack non-therapeutic regions and especially lack an origin of replication and/or a selectable marker gene. In addition, they are advantageously in supercoiled form.

The present invention also is the outcome of the development of a method, of DNA constructs, and of cell hosts that are specific and especially effective for the production of these therapeutic DNA molecules. More especially, the method according to the invention lies in the production of therapeutic DNA molecules defined above, by excision from a plasmid or from a chromosome by site-specific recombination. The method according to the invention is especially advantageous, since it does not necessitate a prior step of purification of the plasmid, is very specific, especially effective, does not decrease the amount of DNA produced, and leads directly to therapeutic molecules of very great genetic purity and of great bioavailability. This method leads, in effect, to the generation of circular DNA molecules (minicircles) essentially containing the gene of interest and the regulator sequences permitting its expression in the cells, tissue, organ, or apparatus, or even the whole body, in which the expression is desired. In addition, these molecules may then be purified by standard techniques.

The site-specific recombination may be carried out by means of various systems that lead to site-specific recombination between sequences. In one embodiment, the site-specific recombination in the method of the invention is obtained by means of two specific sequences that are capable of recombining with one another in the presence of a specific protein, generally designated a recombinase. For this reason, the DNA molecules according to the invention generally comprise, in addition to a transgene, a sequence resulting from this site-specific recombination. The sequences permitting the recombination used in the context of the invention generally comprise from 5 to 100 base pairs, and usually fewer than 50 base pairs.

The site-specific recombination may be carried out in vivo (that is to say in a host cell) or in vitro (that is to say in an isolated plasmid preparation).

In this connection, the present invention also provides particular genetic constructions suitable for the production of the therapeutic DNA molecules defined above. These genetic constructions, or recombinant DNAs, according to the invention comprise, in particular, the gene or genes of interest flanked by the two sequences permitting site-specific recombination, positioned in the direct orientation. The position in the direct orientation indicates that the two sequences follow the same 5'-3' polarity in the recombinant DNA according to the invention. The genetic constructions of the invention can be double-stranded DNA fragments (cassettes) essentially composed of the elements mentioned above. These cassettes can be used for the construction of cell hosts having these elements integrated in their genome (FIG. 1). The genetic constructions of the invention also can be plasmids, that is to say any linear or circular DNA molecule capable of replicating in a given host cell, containing the gene or genes of interest flanked by the two sequences permitting site-specific recombination, positioned in the direct orientation. The construction can be, more specifically, a vector (such as a cloning and/or expression vector), a phage, a virus, and the like. These vectors of the invention may be used to transform any competent cell host for the purpose of the production of minicircles by replication of the vector followed by excision of the minicircle (FIG. 2).

In this connection, another subject of the invention lies in a recombinant DNA comprising one or more genes of interest, flanked by two sequences permitting site-specific recombination, positioned in the direct orientation.

The recombinant DNA according to the invention may be a plasmid comprising at least:

a) an origin of replication and a selection marker gene,
  b) two sequences permitting site-specific recombination, positioned in the direct orientation, and,
  c) placed between said sequences b), one or more genes of interest.

The specific recombination system present in the genetic constructions according to the invention can be of different origins. In particular, the specific sequences and the recombinases used can belong to different structural classes, and in particular to the integrase family of bacteriophage λ or to the resolvase family of the transposon Tn3.

Among recombinases belonging to the integrase family of bacteriophage λ, there may be mentioned, in particular, the integrase of the phages lambda (Landy et al., Science 197: 1147, 1977), P22 and φ80 (Leong et al., J. Biol. Chem. 260: 4468, 1985), HP1 of *Haemophilus influenza* (Hauser et al., J. Biol. Chem. 267 6859,1992), the Cre integrase of phage P1, the integrase of the plasmid pSAM2 (EP 350, 341) or alternatively the FLP recombinase of the 2μ plasmid. When the DNA molecules according to the invention are prepared by recombination by means of a site-specific system of the integrase family of bacteriophage λ, the DNA molecules according to the invention generally comprise, in addition, a sequence resulting from the recombination between two att attachment sequences of the corresponding bacteriophage or plasmid.

Among recombinases belonging to the family of the transposon Tn3, there may be mentioned, in particular, the resolvase of the transposon Tn3 or of the transposons Tn21 and Tn522 (Stark et al., Trends Genet, 8, 432–439, 1992); the Gin invertase of bacteriophage mu, or, alternatively, the resolvase of plasmids, such as that of the par fragment of RP4 (Albert et al., Mol. Microbiol. 12: 131, 1994). When the DNA molecules according to the invention are prepared by recombination by means of a site-specific system of the family of the transposon Tn3, the DNA molecules according to the invention generally comprise, in addition to a transgene, a sequence resulting from the recombination between two recognition sequences of the resolvase of the transposon in question.

According to one embodiment, in the genetic constructions of the present invention, the sequences permitting site-specific recombination are derived from a bacteriophage. In a particular embodiment of the invention, these latter are attachment sequences (attP and attB sequences) of a bacteriophage or sequences derived from such attachment sequences. These sequences are capable of recombining specifically with one another in the presence of a recombinase referred to as an integrase with or without an excisionase. The term "sequences derived from such attachment sequences" includes the sequences obtained by modification(s) of the attachment sequences of the bacteriophages that retain the capacity to recombine specifically in the presence of the appropriate recombinase. Thus, such sequences can be reduced fragments of these sequences or, alternatively, fragments extended by the addition of other sequences (restriction sites, and the like). They can also be variants obtained by mutation(s), in particular by point mutation(s). The terms attP and attB sequences of a bacteriophage or of a plasmid denote, according to the invention, the sequences of the recombination system specific to said bacteriophage or plasmid, that is to say the attP sequence present in said phage or plasmid and the corresponding chromosomal attB sequence.

By way of examples, there may be mentioned, in particular, the attachment sequences of the phages λ, P22, ɸ80, P1, and HP1 of *Haemophilus influenzae* or, alternatively, of plasmid pSAM2 or the 2μ plasmid. The following sequences are advantageously chosen from all or part of the attachment sequences; SEQ ID No. 3 (attB sequence of phage λ; 5'-CTGCTTTTTTATACTAACTTG-3'); SEQ ID No. 4 (attp sequence of phage λ; 5'-CAGCTTTTTTATACTAAGTTG-3'); SEQ ID No. 5 (attB sequence of phage P22; 5'-CAGCGCATTCGTAATGCGAAG-3'); SEQ ID No. 6 (attP sequence of phage P22; 5'-CTTATMTTCGTMTGCGAAG-3'); SEQ ID No. 7 (attB sequence of phage Phi80; 5'-AACACTTTCTTAAATGGTT-3'); SEQ ID No. 8 (attP sequence of phage Phi80; 5'-AACACTTTCTTAAATTGTC-3'); SEQ ID No. 9 (attB sequence of phage HP1; 5'-AAGGGATTTAAAATCCCTC-3'); SEQ ID No. 10 (attp sequence of phage HP1; 5'-ATGGTATTTAAAATCCCTC-3'); and SEQ ID No. 11 (att sequence of plasmid pSAM2; 5'-TTCTCTGTCGGGGTGGCGGGATTTGAACCCA CGACCTCTTCGTCCCGAA-3'). These sequences comprise, in particular, the central region homologous to the attachment sequences of these phages.

In this connection, a plasmid according to the present invention comprises:

(a) a bacterial origin of replication and selection marker gene, (b) the attP and attB sequences of a bacteriophage selected from the phages λ, P22, ɸ80, HP1, and P1 or of plasmid pSAM2 or the 2μ plasmid, or derived sequences; and, (c) placed between said sequences b), one or more genes of interest.

According to this embodiment, the sequences in question are the attachment sequences attP and attB of the bacteriophage λ. Plasmids carrying these sequences are, for example, the plasmids pXL2648, pXL2649, and pXL2650.

One plasmid according to the present invention comprises:

(a) a bacterial origin of replication and a selection marker gene, (b) one or more genes of interest placed between attB and attP sequences of a bacteriophage selected from the phages λ, P22, ɸ80, HP1 and P1 or of a plasmid pSAM2, or the 2μ plasmid, or derived sequences thereof, the attB and attP sequences are positioned at the 5' end 3' end of the gene(s) of interest,.

Plasmids carrying these sequences are pXL3909 and pXL3948, pXL4009. When these plasmids are brought, in vivo or in vitro, into contact with the integrase of phage λ, the sequences recombine with one another to generate in vivo or in vitro, by excision, a minicircle according to the invention essentially comprising one or more gene of interest that is to say the therapeutic portion (FIGS. 2 and 14).

The present invention is thus directed to the minicircle or double-stranded DNA molecule which comprises an expression cassette containing one or more genes of interest under control of a transcription promoter and a transcription terminator active in a mammalian cell, wherein said molecule is circular and in supercoiled form, lacks an origin of replication, lacks a selection marker gene, and comprises a sequence attR resulting from site-specific recombination between an attB and an attP sequence.

In one aspect, the present invention is directed to the minicircle or double-stranded DNA molecule which comprises an expression cassette containing one or more genes of interest under control of a transcription promoter and a transcription terminator active in a mammalian cell, wherein said molecule is circular and in supercoiled form, lacks an origin of replication, lacks a selection marker gene, and comprises a sequence attL resulting from site-specific recombination between an attB and an attP sequence.

The minicircle may comprise a sequence attL as set forth in SEQ ID NO: 12 (5'-TTCTTTTTTTCTTGAAGCCTGCTTTTT-TATACTAAGTTGGC ATTATAAAAAAGCATTGCTTAT-CAATTTGTTGCMCGAACAGGTCACTATCAGTCA AAATAAAATCATTATTTGATT-3'; FIG. 14). Minicircles carrying these sequences are for example MC3909, MC3948, and MC4009.

According to another embodiment of the present invention, the sequences permitting site-specific recombination, are also derived from a bacteriophage, and are attachment sequences attR and attL of the bacteriophage λ.

One plasmid according to this embodiment comprises:

(a) a bacterial origin of replication and a selection marker gene, (b) the attR and attL sequences of a bacteriophage selected from the phages λ, P22, ɸ80, HP1, and P1 or of plasmid pSAM2 or the 2μ plasmid, or derived sequences; and, (c) placed between said sequences b), one or more genes of interest.

Plasmids carrying these sequences are, for example, the plasmids pXL3955 and pXL4007. When these plasmids are brought in vivo or in vitro, into contact with the integrase and the excisionase of phage λ, the sequences recombine with one another to generate in vivo or in vitro, by excision, a minicircle according to the invention essentially comprising the elements (c), that is to say the therapeutic portion (FIG. 23).

The present invention is thus further directed to the minicircle or double-stranded DNA molecule which comprises an expression cassette containing one or more genes of interest under control of a transcription promoter and a transcription terminator active in a mammalian cell, wherein said molecule is circular and in supercoiled form, lacks an origin of replication, lacks a selection marker gene, and comprises a sequence attB resulting from site-specific recombination between an attR and an attL sequence.

The minicircle may comprise a sequence attB as set forth in SEQ ID NO: 13 (5'-TTCTTTTTTTTCTTGAAGCCTGCTTTTTTATACTAAC TTGAGC-3'; FIG. 23). Minicircles carrying these sequences are for example MC3955 and MC4007.

Still according to one embodiment of the invention, the sequences permitting site-specific recombination are derived from the loxP region of phage P1. This region is composed essentially of two repeat sequences capable of recombining specifically with one another in the presence of a protein, designated Cre (Sternberg et al., J. Mol. Biol. 150: 467, 1971). In a particular variant, the invention hence relates to a plasmid comprising (a) a bacterial origin of replication and a selection marker gene; (b) the repeat sequences of bacteriophage P1 (loxP region); and (c), placed between said sequences (b), one or more genes of interest.

According to another embodiment, in the genetic constructs of the present invention, the sequences permitting site-specific recombination are derived from a transposon. The sequences in question may be recognition sequences of the resolvase of a transposon or derived sequences. By way of example, there may be mentioned, in particular, the recognition sequences of the transposons Tn3, Tn21, and Tn522. By way of an additional example, there may be mentioned the sequence SEQ ID No. 14 (recognition sequence of the resolvase of transposon Tn3; 5'-CGTCGAAATATTATAAATTATCAGACA-3') or a derivative of that sequence (see also Sherrat, P., pp. 163–184, Mobile DNA, eds. D. Berg and M. Howe, American Society for Microbiology, Washington D.C., 1989).

According to another embodiment of the invention, the plasmids of the invention comprise, in addition to the elements described above, a multimer resolution sequence. This may be the mrs (multimer resolution system) sequence of the plasmid RK2. This aspect of the invention relates to a plasmid comprising:

(a) a bacterial origin of replication and a selection marker gene, (b) the attP and attB sequences of a bacteriophage, in the direct orientation, selected from the phages λ, P22, φ80, HP1, and P1 or of plasmid pSAM2 or the 2μ plasmid, or derived sequences; and, (c) placed between said sequences b), one or more genes of interest and the mrs sequence of plasmid RK2.

This aspect of the invention also relates to a plasmid comprising:

(a) a bacterial origin of replication and a selection marker gene, (b) the attR and attL sequences of a bacteriophage, in the direct orientation, selected from the phages λ, P22, φ80, HP1, and P1 or of plasmid pSAM2 or the 2μ plasmid, or derived sequences; and, (c) placed between said sequences b), one or more genes of interest and the mrs sequence of plasmid RK2.

This embodiment has useful properties. For example, when plasmids pXL2649; pXL2650; pXL3909; pXL3948; pXL3955, pXL4007; and pXL4009 are brought into contact with the integrase with or without the excisionase of the bacteriophage in vivo, the sequences recombine to generate the minicircle and the miniplasmid, but also multimeric or topological forms of minicircle or of miniplasmid. It may be useful to decrease the concentration of these forms in order to increase the production and facilitate the purification of minicircle.

A person skilled in the art knows the multimeric forms of plasmids. For example, the cerfragment of ColE1 (Summers et al., Cell 36: 1097, 1984) or the mrs site of the par locus of RK2 (L. Ebert Mol. Microbiol. 2: 131, 1994) permit the resolution of multimers of plasmids and participate in an enhanced stability of the plasmid. However, whereas resolution at the cer site requires four proteins encoded by the *E. coli* genome (Colloms et al., J. Bacteriol. 172: 6973, 1990), resolution at the mrs site requires only the ParA protein for which the parA gene is mapped on the par locus of RK2. As a result, it would appear advantageous to use all or a portion of the par locus containing parA and the mrs sequence. For example, the mrs sequence may be placed between the attB and attP sequences or between the attR and attL sequences of phage λ, and the parA gene be expressed in trans or in cis from its own promoter or from an inducible promoter.

In this connection, a particular plasmid of the invention comprises:

(a) a bacterial origin of replication and a selection marker gene, (b) the attp and attB sequences of a bacteriophage, in the direct orientation, selected from the phages lambda, P22, φ80, HP1, and P1, or of plasmid pSAM2 or the 2μ plasmid, or derived sequences, (c) placed between said sequences b), one or more genes of interest and the mrs sequence of plasmid RK2, and (d) the parA gene of plasmid RK2.

Another plasmid of the invention comprises:

(a) a bacterial origin of replication and a selection marker gene, (b) the attR and attL sequences of a bacteriophage, in the direct orientation, selected from the phages lambda, P22, φ80, HP1, and P1, or of plasmid pSAM2 or the 2μ plasmid, or derived sequences, (c) placed between said sequences b), one or more genes of interest and the mrs sequence of plasmid RK2, and (d) the parA gene of plasmid RK2.

Such plasmids may be plasmids pXL2960; pXL3909; pXL3948; pXL3955; pXL4007 and pXL4009 described in the examples. It may be employed, and can enable a minicircle to be produced exclusively in the monomeric form.

According to another variant, the plasmids of the invention comprise two sets of site-specific recombination sequences from different families. These advantageously comprise a first set of integrase-dependent sequences and a second set of parA-dependent sequences. The use of two sets of sequences enables the production yields of minicircles to be increased when the first site-specific recombination is incomplete. Thus, when plasmids pXL2650, pXL2960, pXL3909 pXL3948 or pXL4009 are brought into contact with the integrase of the bacteriophage in vivo, the sequences recombine to generate the miniplasmid and the minicircle. Also, when plasmids pXL3955 or pXL4007 are brought in contact with the excisionase and the integrase of the bacteriophage in vivo, the sequences recombine to generate the miniplasmid and the minicircle. However, this reaction is not complete (5 to 10% of initial plasmid may be left). The introduction, in proximity to each of the att sequences of phage λ, of an mrs sequence of RK2 enables the production of minicircles to be increased. Thus, after induction of the integrase with or without induction of the excisionase of phage λ and Int-dependent recombination, the unrecombined molecules will be able to come under the control of the ParA protein of RK2 and recombine at the mrs sites. Conversely, after induction of the ParA protein and ParA-dependent recombination, the unrecombined molecules will be able to come under the control of the integrase of phage λ and will be able to recombine at the att sites. Such constructions thus make it possible to produce minicircle with negligible amounts of unrecombined molecules. The att sequences, like the mrs sequences, are in the direct orientation, and the int and parA genes may be induced simultaneously or successively from the same inducible promoter or from two inducible promoters. The sequences in question may be the attB and attP or the attR and attL attachment sequences of phage λ in the direct orientation and two mrs sequences of RK2 in the direct orientation.

As stated above, another aspect of the present invention lies in a method for the production of therapeutic DNA molecules defined above, by excision, from a plasmid or chromosome, by site-specific recombination.

Another subject of the present invention is a method for the production of a DNA molecule (minicircle) as defined above, according to which a culture of host cells containing a recombinant DNA as defined above is brought into contact with the integrase with or without the excisionase, enabling site-specific recombination to be induced. In one embodiment of the invention, the culture and the integrase with or without the excisionase are brought into contact either by transfection or infection with a plasmid or a phage containing the gene for said integrase and when applicable the gene for the excisionase. Alternatively, for example, the expression of genes coding for said integrase and when applicable the excisionase, present in the host cell, are induced. As mentioned below, these genes may be present in the host cell in integrated form in the genome, on a replicative plasmid, or, alternatively, on the plasmid of the invention, in the non-therapeutic portion.

To permit the production of the minicircles according to the invention by site-specific recombination in vivo, the integrase with/without the excisionase used are introduced into, or induced in, cells or the culture medium at a particular instant. For this purpose, different methods may be used. According to a first method, a host cell is used containing, for example, the recombinase gene, i.e., the integrase gene with or without the excisionase gene, in a form permitting its regulated expression. The integrase gene with or without the excisionase gene may, for example, be introduced under the control of a promoter, or of a system of inducible promoters, or, alternatively, in a temperature-sensitive system.

In particular, the integrase gene may be present in a temperature-sensitive phage, latent during the growth phase, and induced at a suitable temperature (for example, lysogenic phage λ Xis⁻ c/857).

Alternatively, the gene may be under the control of a regulated promoter, for example, the placUV5 promoter, the host cell is designated *Escherichia coli* G6191.

The integrase with or without the excisionase gene may be under the control of a regulated promoter, for example the $P_{BAD}$ promoter of the araBAD (arabinose) operon, which is regulated by arabinose (Guzman et al., J. Bacteriol, 1995, 4121–4130; U.S. Pat. No. 5,028,530). Use of $P_{BAD}$ promoter allows sufficient expression of excisionase and integrase in presence of arabinose, as the inducing agent, and thus more than 90% of recombination of the plasmids which are present in high copies number in the bacteria, whereas in absence of arabinose, the promoter is tightly inhibited. The cassette for expression of the integrase with/without excisionase may be carried by a plasmid, a phage, or even by the plasmid of the invention in the non-therapeutic region. It may be integrated in the genome of the host cell or maintained in replicative form. Such host cells are, for example, *Escherichia coli* G6264 and *Escherichia coli* G6289. According to another method, the cassette for expression of the gene(s) is carried by a plasmid or a phage used to transfect or infect the cell culture after the growth phase. In this case, it is not necessary for the gene to be in a form permitting its regulated expression. Any constitutive promoter may be used. The DNA may also be brought into contact with the integrase and when applicable the excisionase in vitro, on a plasmid preparation, by direct incubation with the protein.

In one aspect of the present invention, a host cell capable of expressing the recombinase, i.e., the integrase with/without excisionase in a regulated manner is used. In this embodiment the recombinase is supplied directly by the host cell after induction. In effect, it suffices simply to place the cells in culture at the desired time under the conditions for expression of the recombinase gene (permissive temperature for a temperature-sensitive gene, addition of an inducer for a regulated promoter, and the like) in order to induce the site-specific recombination in vivo and, thus, the excision of the minicircle of the invention. In addition, this excision takes place in especially high yields, since all the cells in the culture express the recombinase, which is not necessarily the case if a transfection or an infection has to be carried out in order to transfer the recombinase gene into the cultured cells.

According to another embodiment, the method of the invention comprises the excision of the molecules of therapeutic DNA by site-specific recombination from a plasmid. This embodiment employs the plasmids described above permitting, in a first stage, replication in a chosen host, and then, in a second stage, the excision of the non-therapeutic portions of said plasmid (such as the origin of replication and the resistance gene) by site-specific recombination, generating the circular DNA molecules of the invention. To carry out the method, different types of plasmid may be used, and especially a vector, a phage or a virus. A replicative vector may be used in one embodiment of the invention.

In another embodiment, the method of the invention comprises a step of transforming host cells with a plasmid as defined above, followed by culturing of the transformed cells, enabling suitable amounts of plasmid to be obtained. Excision by site-specific recombination is then carried out by bringing the plasmid into contact with the recombinase under the conditions described above (FIGS. 2, 14 & 23). As stated above, in this embodiment, the site-specific recombination may be carried out in vivo (that is to say in the host cell) or in vitro (that is to say on a plasmid preparation).

According to one embodiment of the invention, the DNA molecules of the invention are hence obtained from a replicative vector, by excision of the non-therapeutic portion carrying, in particular, the origin of replication and the selection marker gene, by site-specific recombination.

According to another embodiment, the method of the invention comprises the excision of the DNA molecules from the genome of the host cell by site-specific recombination. This embodiment is based more especially on the construction of cell hosts comprising, inserted into their genome, one or more copies of a cassette comprising the gene of interest flanked by the sequences permitting recombination (FIG. 1). Different techniques may be used for insertion of the cassette of the invention into the genome of the host cell. Insertion at several distinct points of the genome may be obtained by using integrative vectors. In this connection, different transposition systems such as, for example, the mu system or defective transposons such as Tn10 derivatives, may be used (Kleckner et al., Meth. Enzymol. 204: 139, 1991; Groisman E., Meth. Enzymol. 204: 180, 1991). The insertion also may be carried out by homologous recombination, enabling a cassette containing two recombination sequences in the direct orientation flanking one or more genes of interest to be integrated in the genome of the bacterium. This process may, in addition, be reproduced as many times as desired so as to have the largest possible number of copies per cell. Another technique consists in using an in vivo amplification system using recombination, as described in Labarre et al., J. Bacteriol. 175: 1001–107, 1993), so as to augment from one copy of the cassette to a much larger copy number.

One such technique comprises the use of miniMu. To this end, miniMu derivatives are constructed comprising a resistance marker, the functions required in cis for their transposition, and a cassette containing two recombination sequences in the direct orientation flanking the gene or genes of interest. These miniMus are advantageously placed at several points of the genome using a selectable marker (e.g., kanamycin resistance) enabling several copies per genome to be selected (Groisman E., supra). As described above, the host cell in question also can express inducibly a site-specific recombinase leading to the excision of the fragment flanked by the recombination sequences in the direct orientation. After excision, the minicircles may be purified by standard techniques.

This embodiment of the method of the invention leads to the generation of a single type of plasmid molecule: the minicircle of the invention. The cells do not contain, in effect, any other episomal plasmid, in contrast to the situation during production of a minicircle from a plasmid (FIGS. 1 and 2).

Another aspect of the invention lies in a modified host cell comprising, inserted into its genome, one or more copies of a recombinant DNA as defined above.

The invention also relates to any recombinant cell containing a plasmid as defined above. These cells are obtained by any technique known to a person skilled in the art enabling a DNA to be introduced into a given cell. Such a technique can be, for example, transformation, electroporation, conjugation, protoplast fusion or any other technique known to a person skilled in the art. As regards transformation, different protocols have been described in the prior art. For example, cell transformation may be carried out by treating whole cells in the presence of lithium acetate and polyethylene glycol according to the technique described by Ito et al. (J. Bacteriol. 153: 163–168, 1983), or in the presence of ethylene glycol and dimethyl sulphoxide according to the technique of Durrens et al. (Curr. Genet. 18: 7, 1990). An alternative protocol has been described in Patent Application EP 361,991. As regards electroporation, this may be carried out according to Becker and Guarentte (Meth. Enzymol. 194: 182, 1991).

The method according to the invention may be carried out in any type of cell host. Such hosts can be, in particular, bacteria or eukaryotic cells (yeasts, animal cells, plant cells), and the like. Among bacteria, *Escherichia coli, Bacillus subtilis,* Streptomyces, Pseudomonas (*P. putida, P. aeruginosa*), *Rhizobium meliloti, Agrobacterium tumefaciens, Staphylococcus aureus, Streptomyces pristinaespirais, Enterococcus faecium* or Clostridium, and the like, may be mentioned. Among bacteria, *E. coli* is commonly used. Among yeasts, Kluyveromyces, Saccharomyces, Pichia, Hansenula, and the like, may be mentioned. Among mammalian animal cells, CHO, COS, NIH3T3, and the like, may be mentioned.

In accordance with the host used, a person skilled in the art will adapt the selection/replication of plasmid described in the invention. In particular, the origin of replication and the selection marker gene are chosen in accordance with the host cell selected.

The selection marker gene may be a resistance gene, for example, conferring resistance to an antibiotic (ampicillin, kanamycin, geneticin, hygromycin, and the like), or any gene endowing the cell with a function, which it no longer possesses (for example, a gene which has been deleted on the chromosome or rendered inactive), the gene on the plasmid reestablishing this function. For example, the selectable tRNA suppressor, supPhe, corrects an amber mutation in the chromosomal argE gene making it possible for the $argE_{am}$ strain to grow on minimal media lacking arginine. This selectable marker gene allows plasmid selection and production in minimal media.

In a particular embodiment, the method of the invention comprises an additional step of purification of the minicircle.

In this connection, the minicircle may be purified by standard techniques of plasmid DNA purification, since it is supercoiled like plasmid DNA. These techniques comprise, inter alia, purification on a cesium chloride density gradient in the presence of ethidium bromide, or alternatively the use of anion exchange columns (Maniatis et al., 2001 supra). In addition, if the plasmid DNA corresponding to the non-therapeutic portions (origin of replication and selectable marker in particular) is considered to be present in an excessively large amount, it also is possible, after or before the purification, to use one or more restriction enzymes which will digest the plasmid and not the minicircle, enabling them to be separated by techniques that separate supercoiled DNA from linear DNA, such as a cesium chloride density gradient in the presence of ethidium bromide (Maniatis et al., 2001 supra).

In addition, the present invention also describes improved methods for the purification of minicircles. These methods enable minicircles of very great purity to be obtained in large yields in a single step. These improved methods are based on the interaction between a double-stranded sequence present in the minicircle and a specific ligand. The ligand can be of various natures, and in particular, protein, chemical or nucleic acid in nature. In one embodiment of the invention, it is a ligand of the nucleic acid type, and in particular, an oligonucleotide, optionally chemically modified, which forms by hybridization a triple helix with the specific sequence present in the DNA molecule of the invention. It was, in effect, shown that some oligonucleotides were capable of specifically forming triple helices with double-stranded DNA sequences (Hélène et al., Biochim. Biophys. Acta 1049 (1990) 99; see also FR 94/15162 incorporated in the present application by reference).

In one variant of the invention, the DNA molecules of the invention hence contain, in addition, a sequence capable of interacting specifically with a ligand (FIGS. 3, 14 & 23).

This may be a sequence capable of forming, by hybridization, a triple helix with a specific oligonucleotide. This sequence may be positioned at any site of the DNA molecule of the invention, provided it does not affect the functionality of the gene of interest. This sequence is also present in the genetic constructions of the invention (plasmids, cassettes), in the portion containing the gene of interest (see, in particular, the plasmid pXL2650, pXL3909, 3948, pXL3955, pXL4007 and pXL4009). In general, the specific sequence present in the DNA molecule of the invention comprises, but is not limited to, between approximately 5 and 30 base pairs (pXL2650 has a 51bp sequence, but the others are in the written range).

The oligonucleotides used for carrying out the method according to the invention can contain the following bases:
- thymidine (T), which can form triplets with A.T doublets of double-stranded DNA (Rajagopal et al., Biochem 28 (1989) 7859);
- adenine (A), which can form triplets with A.T doublets of double-stranded DNA (not as strong as 1 and 4);
- guanine (G), which can form triplets with G.C doublets of double-stranded DNA;
- protonated cytosine (C+), which can form triplets with G.C doublets of double-stranded DNA (Rajagopal et al., supra).

In one embodiment, the oligonucleotide used comprises a homopyrimidine sequence containing cytosines and the specific sequence present in the DNA molecule is a homopurine-homopyrimidine sequence. The presence of cytosines makes it possible to have a triple helix which is stable at acid pH where the cytosines are protonated, and destabilized at alkaline pH where the cytosines are neutralized.

To permit the formation of a triple helix by hybridization, it is important for the oligonucleotide and the specific sequence present in the DNA molecule of the invention to be complementary. In this connection, to obtain the best yields and best selectivity, an oligonucleotide and a specific sequence that are fully complementary are used in the method of the invention. Possible combinations are, in particular, a poly(CTT) oligonucleotide and a poly(GAA) specific sequence. By way of example, there may be mentioned the oligonucleotide of sequence GAGGCTTCTTCT-TCTTCTTCTTCTT (SEQ ID No. 15), other examples are 5'-TCTTTTTTTCCT-3' (SEQ ID No: 47) and 5'-TTCTTTTTTTTCTT-3' (SEQ ID No: 48) in which the bases GAGG do not form a triple helix but enable the oligonucleotide to be spaced apart from the coupling arm.

Other examples of oligonucleotides having sequences 5'-TTCTTCTTGCTTCTCTTCTT-3' (SEQ ID No: 16); 5'-TTCTTCTTGTTTCTCTTCTT-3' (SEQ ID No: 17), and 5'-TTCTTCTTCCTTCTCTTCTT-3' (SEQ ID No: 18) are capable of forming a triple helix with a specific sequence present in the DNA molecule of the invention having a nucleotide sequence 5'-(R)$_n$—(N)$_t$—(R')$_m$-3', wherein R and R' represent nucleotides only composed of purine bases, n and m are integers less than 9, the sum of which is greater than 5, N is a nucleotide sequence comprising both purine bases and pyrimidine bases, and t is an integer less than 8. Such a specific sequence present in the DNA molecule of the invention is for example 5'-AAGAAGCATGCAGAGAAGAA-3' (SEQ ID NO: 19).

In another example, the specific sequence present in the minicircle or DNA molecule according to the present invention is contiguous or comprised within the attL or the attB sequence which result from the site-specific recombination between the attB and attP sequences, or the attR and attL sequences, respectively, or derived sequences thereof. Accordingly, the double-stranded DNA molecule of the present invention comprises a sequence that forms a triple helix contiguous to the attL sequence as set forth in SEQ ID NO: 12. The double-stranded DNA molecule may comprise a sequence that forms a triple helix contiguous to the attB sequence as set forth in SEQ ID NO: 13.

It is understood, however, that some mismatches may be tolerated, provided they do not lead to too great a loss of affinity. The oligonucleotide used may be natural (i.e., composed of unmodified natural bases) or chemically modified. In particular, the oligonucleotide may possess some chemical modifications enabling its resistance or its protection against nucleases, or its affinity for the specific sequence, to be increased.

Thus, the oligonucleotide may be rendered more resistant to nucleases by modification of the skeleton (e.g. methylphosphonates, phosphorothiates, phosphotriester, phosphoramidate, and the like).

Another type of modification has as its objective, more especially, to improve the interaction and/or the affinity between the oligonucleotide and the specific sequence. In particular, the cytosines of the oligonucleotide may be methylated. The oligonucleotide thus methylated displays the property of forming a stable triple helix with the specific sequence at neutral pH. Hence it makes it possible to work at higher pH values than the oligonucleotides of the prior art, that is to say at pH values where the risks of degradation of the plasmid DNA are lower.

The length of the oligonucleotide used in the method of the invention is more than 3 bases. In one embodiment, the oligonucleotide is between about 5 and 50 bases. In another embodiment, an oligonucleotide of length greater than 10 bases is used. The length may be adapted to each individual case by a person skilled in the art in accordance with the desired selectivity and stability of the interaction.

The oligonucleotides according to the invention may be synthesized by any known technique. In particular, they may be prepared by means of nucleic acid synthesizers. Any other method known to a person skilled in the art also may be used.

To carry out the method of the invention, the specific ligand (protein, nucleic acid, and the like) may be grafted onto or otherwise attached to a support. Different types of supports may be used for this purpose, such as, functionalized chromatography supports, in bulk form or prepacked in columns, functionalized plastic surfaces, or functionalized latex beads, functionalized thermoresponsive polymers, such as poly(N-isopropylacrylamide) as described by Mori et al. (Biotechnology and Bioengineering, 72:261–268, 2001) and Freitag et al. (Chimia, 55:196–200, 2001), magnetic, or otherwise. Chromatography supports are optionally used. By way of example, the chromatography supports which may be used include, but are not limited to, agarose, acrylamide or dextran, as well as their derivatives (such as Sephadex, Sepharose, Superose, etc.), polymers such as poly(styrenedivinylbenzene), or grafted or ungrafted silica, for example. The chromatography columns can function in the diffusion mode, the perfusion mode, or in the so-called expanded bed or fluidized bed mode.

To permit its covalent coupling to the support, the oligonucleotide is generally functionalized. Thus, it may be modified by a thiol, amine or carboxyl terminal group at the 5' or 3' position. In particular, the addition of a thiol, amine or carboxyl group makes it possible, for example, to couple the oligonucleotide to a support bearing disulphide, maleimide, amine, carboxyl, ester, epoxide, cyanogen bromide or aldehyde functions. These couplings form by establishment of disulphide, thioether, ester, amide or amine links between the oligonucleotide and the support. Any other method known to a person skilled in the art may be used, such as bifunctional coupling reagents, for example.

It can be advantageous for the oligonucleotide to contain an "arm" and a "spacer" sequence of bases. The use of an arm makes it possible, in effect, to bind the oligonucleotide at a chosen distance from the support, enabling its conditions of interaction with the DNA to be improved. The arm advantageously consists of a linear carbon chain, comprising 1 to 18. In another embodiment, the arm may comprise 6 or 12 ($CH_2$) groups. The arm also comprises an amine which permits binding to the column. The arm is linked to a phosphate of the oligonucleotide or of a "spacer" composed of bases which do not interfere with the hybridization. Thus, the "spacer" can comprise purine bases. As an example, the "spacer" can comprise the sequence glycine-alanine-glycine-glycine. The arm is advantageously composed of a linear carbon chain comprising 6 or 12 carbon atoms.

Different types of support may be used. These can be functionalized chromatographic supports, in bulk or prepacked in a column, functionalized plastic surfaces or functionalized latex beads, magnetic or otherwise. Chromatographic supports may be used. For example, chromatographic supports which may be used are agarose, acrylamide or dextran as well as their derivatives (such as Sephadex, Sepharose, Superose, etc.), polymers such as poly(styrene/divinylbenzene), or grafted or ungrafted silica, for example. The chromatography columns can operate in the diffusion or perfusion mode.

In another embodiment of the invention, minicircles of high purity are obtained through purification over two columns comprising triple helix-forming oligonucleotides. This two-column method takes advantage of the observation that smaller DNA molecules, for example, a minicircle according to the invention, are more strongly retained on an affinity column by triple helix formation than are larger DNA molecules, for examples plasmids, that also form triple helices with the column ligand. This method involves, for example, a first affinity column comprising a ligand that forms a triple helix with sequences present in a plasmid and miniplasmid of the invention, but not with the corresponding minicircle. The flow through from this column, which is enriched for the minicircle, is applied to a second column comprising a ligand that forms a triple helix with a sequence present in the minicircle and the plasmid, but not in the miniplasmid. Under conditions that eliminate the miniplasmid, the minicircle can be retained by the second column and then eluted under other conditions; it allows minicircles of pharmaceutical purity to be obtained by this method.

In still another embodiment, the first affinity column comprises a ligand that forms a triple helix with sequences present in the minicircle of the invention, but not within the miniplasmid. The minicircle is thus retained on the first column, and may then be eluted by changing the buffer. The eluate which is enriched for the minicircle, is further applied to a second column comprising a ligand that forms a triple helix with a sequence present in the miniplasmid and the plasmid, but not in the minicircle. The flow through from this second column contains the minicircle of pharmaceutical purity according to the present invention.

The DNA molecules according to the invention may be used in any application of vaccination or of gene and cell therapy, for the transfer of a gene to a body, a tissue or a given cell. In particular, they may be used for a direct administration in vivo, or for the modification of cells in vitro or ex vivo with a view to their implantation in a patient. In this connection, the molecules according to the invention may be used as they are (in the form of naked DNA), or in combination with different synthetic or natural, chemical and/or biochemical vectors. The latter can be, in particular, cations (calcium phosphate, DEAE-dextran, etc.) which act by forming precipitates with DNA, that can be "phagocytosed" by the cells. They also can be liposomes in which the DNA molecule is incorporated and which fuse with the plasma membrane. Synthetic gene transfer vectors are generally lipids or cationic polymers that complex DNA and form a particle therewith carrying positive surface charges. These particles can interact with the negative charges of the cell membrane and then cross the latter. DOGS (Transfectam™) or DOTMA (Lipofectin™) may be mentioned as examples of such vectors. Chimeric proteins also have been developed: they comprise a polycationic portion, which condenses DNA, linked to a ligand, which binds to a membrane receptor and carries the complex into the cells by endocytosis. The DNA molecules according to the invention also may be used for gene transfer into cells by physical transfection techniques such as bombardment, electroporation, and the like. In addition, prior to their therapeutic use, the molecules of the invention may optionally be linearized, for example by enzymatic cleavage.

In this connection, another subject of the present invention relates to any pharmaceutical composition comprising at least one DNA molecule as defined above. This molecule may be naked or combined with a chemical and/or biochemical transfection vector. The pharmaceutical compositions according to the invention may be formulated with a view to topical, oral, parenteral, intranasal, intravenous, intramuscular, subcutaneous, intra-ocular, transdermal, and the like, administration. The DNA molecule may be used in an injectable form or by application. It may be mixed with any pharmaceutically acceptable vehicle for an injectable formulation, for example, for a direct injection at the site to be treated. The compositions may be in the form of isotonic sterile solutions, or of dry, in particular lyophilized compositions which, on addition of sterilized water or physiological saline as appropriate, enable injectable solutions to be prepated. Diluted Tris or PBS buffers in glucose or sodium chloride also may be used. In one embodiment, the nucleic acid of the invention is directly injected into the affected region of the patient, thereby allowing the therapeutic effect to be concentrated in the tissues affected. The doses of nucleic acid used may be adapted in accordance with different parameters, and in particular in accordance with the gene, the vector, the mode of administration used, the pathology in question, or, alternatively, the treatment period desired.

The DNA molecules of the invention may contain one or more genes of interest, that is to say one or more nucleic acids (cDNA, gDNA, synthetic or semi-synthetic DNA, and the like) whose transcription and, where appropriate, translation in the target cell generate products of therapeutic, vaccinal, agricultural or veterinary value.

Among the genes of therapeutic value, there may be mentioned, for example, genes coding for enzymes, blood derivatives, hormones, lymphokines, including interleukins, interferons, TNF, and the like (FR 92/03120), growth factors, neurotransmitters, their precursors, or synthetic enzymes, trophic factors, including BDNF, CNTF, NGF, IGF, GMF, aFGF, bFGF, NT3, NT5, VEGF and the like; apolipoproteins, namely ApoAl, ApoAlV, ApoE, and the like (FR 93/05125), dystrophin or a minidystrophin (FR 91/11947), tumour suppressive genes, including p53, Rb, Rap1A, DCC, k-rev, and the like (FR 93/04745), genes coding for factors involved in coagulation, including factors VII, VIII, IX, and the like, suicide genes, including thymidine kinase, cytosine deaminase, and the like; or alternatively all or part of a natural or artificial immunoglobulin (Fab, ScFv, and the like), a ligand RNA (WO 91/19813), and the like. The therapeutic gene also can be an antisense gene or sequence whose expression in the target cell enables gene expression or the transcription of cellular mRNAs to be controlled. Such sequences can, for example, be transcribed in the target cell into RNAs complementary to cellular mRNAs, and can thus block their translation into protein, according to the technique described in Patent EP 140,308.

The gene of interest can also be a vaccinating gene, that is to say a gene coding for an antigenic peptide, which can generate an immune response in man or animals for the purpose of vaccine production. Such antigenic peptides can be, for example, those specific to the Epstein-Barr virus, the HIV virus, the hepatitis B virus (EP 185,573) or the pseudorabies virus, or alternatively tumour-specific peptides (EP 259,212).

Generally, in the plasmids and molecules of the invention, the gene of therapeutic, vaccinal, agricultural, or veterinary value also contains a transcription promoter region which is functional in the target cell or body (e.g., mammals), as well as a region located at the 3' end that comprises a transcription termination signal and a polyadenylation site (expression cassette). As regards the promoter region, this can be a promoter region naturally responsible for the expression of the gene in question when the latter is capable of functioning in the cell or body in question. The promoter region also may be of different origin (i.e., responsible for the expression of other proteins) or even a synthetic promoter. The promoter sequence may be from eukaryotic or viral origin. For example, the promoter sequence may originate from the genome of the target cell. Among eukaryotic promoters, it is possible to use any promoter or derived sequence that stimulates or represses the transcription of a gene, specifically or otherwise, inducibly or otherwise, strongly or weakly. The promoter may be, for example, a ubiquitous promoter (e.g., promoter of the HPRT, PGK, α-actin, tubulin, and the like, genes), a promoter of intermediate filaments (e.g., promoter of the GFAP, desmin, vimentin, neurofilament, keratin, and the like, genes), a promoter of therapeutic genes (e.g., the promoter of the MDR, CFTR, factor VIII, ApoAI, and the like, genes), a tissue-specific promoter (e.g., promoter of the pyruvate kinase gene, villin gene, gene for intestinal fatty acid binding protein, gene for α-actin of smooth muscle, the promoter of the CARP protein, the muscle creatine kinase (MCK) promoter, the myosin light chain 3F (MLC3F) promoter and the like) or, alternatively, a promoter that responds to a stimulus (e.g., steroid hormone receptor, retinoic acid receptor, and the like). Similarly, the promoter sequences may be those originating from the genome of a virus, such as, for example, the promoters of the adenovirus E1A and MLP genes, the cytomegalovirus (CMV) early promoter, or alternatively the Rous sarcoma virus (RSV) LTR promoter, and the like. In addition, these promoter regions may be modified by the addition of activator or regulator sequences or sequences permitting a tissue-specific or -preponderant expression.

Moreover, the gene of interest may also contain a signal sequence directing the synthesized product into the pathways of secretion of the target cell. This signal sequence can be the natural signal sequence of the product synthesized, but it may also be any other functional signal sequence, or an artificial signal sequence.

Depending on the gene of interest, the DNA molecules of the invention may be used for the treatment or prevention of a large number of pathologies, including genetic disorders (e.g., dystrophy, cystic fibrosis, and the like), neurodegenerative diseases (e.g., Alzheimer's, Parkinson's, amyotrophic lateral sclerosis (ALS), and the like), cancers, pathologies associated with disorders of coagulation or with dyslipoproteinaemias, pathologies associated with viral infections (e.g., hepatitis, AIDS, and the like), or in the agricultural and veterinary fields, and the like.

The present invention will be described more completely by means of the examples which follow, which are to be regarded as illustrative and non-limiting.

BRIEF DESCRIPTION OF THE DRAWINGS

FIG. 24: Construction of *E. coli* strain G6289.

FIG. 26 displays schematic representations of plasmids pXL3001 and pXL3032, and of minicircle 3677.

GENERAL TECHNIQUES OF CLONING AND MOLECULAR BIOLOGY

Figure 1:
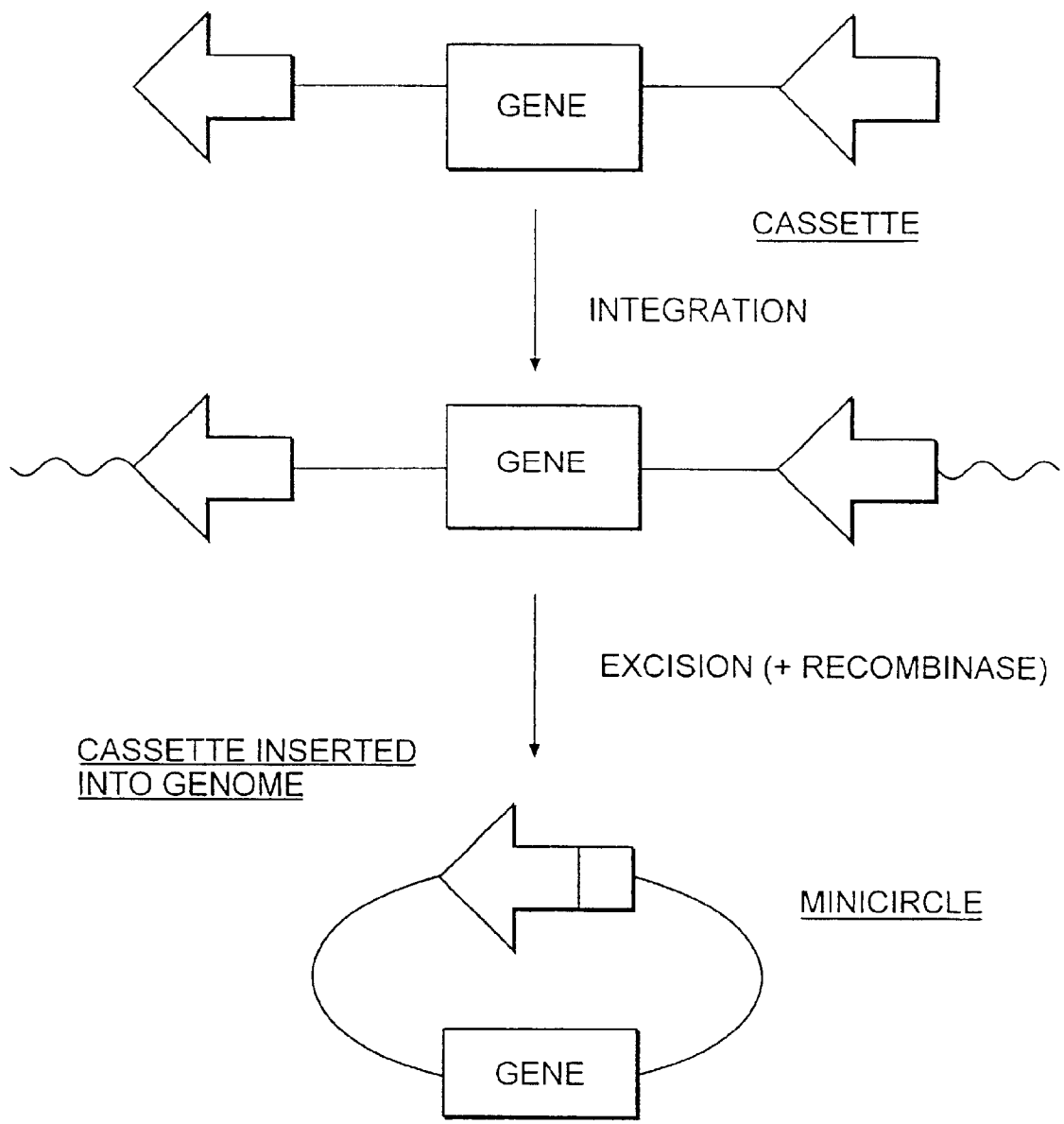
FIG. 1: Production of a minicircle from a cassette integrated in the genome.
Figure 2:
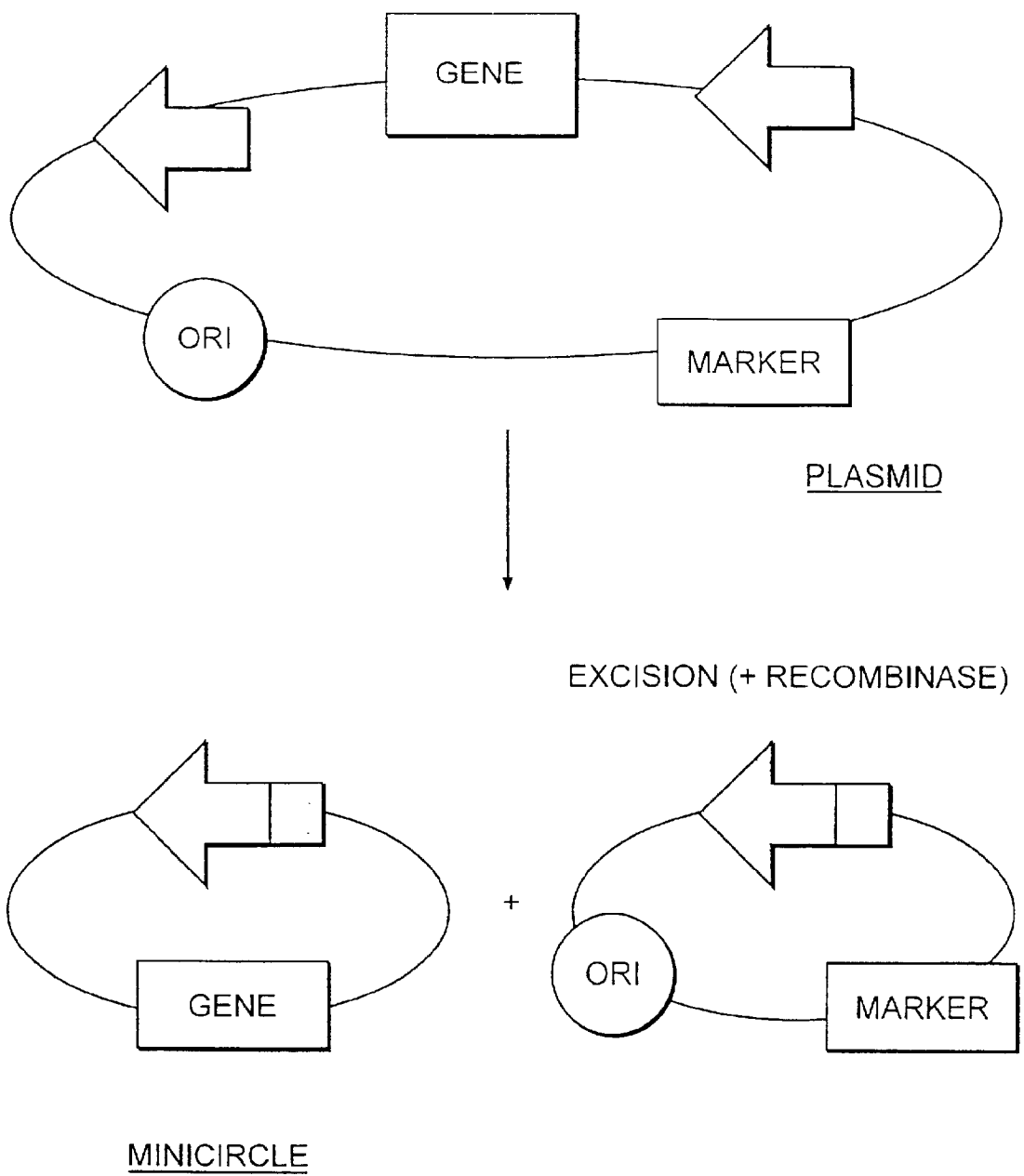
FIG. 2: Production of a minicircle from a plasmid.
Figure 3:
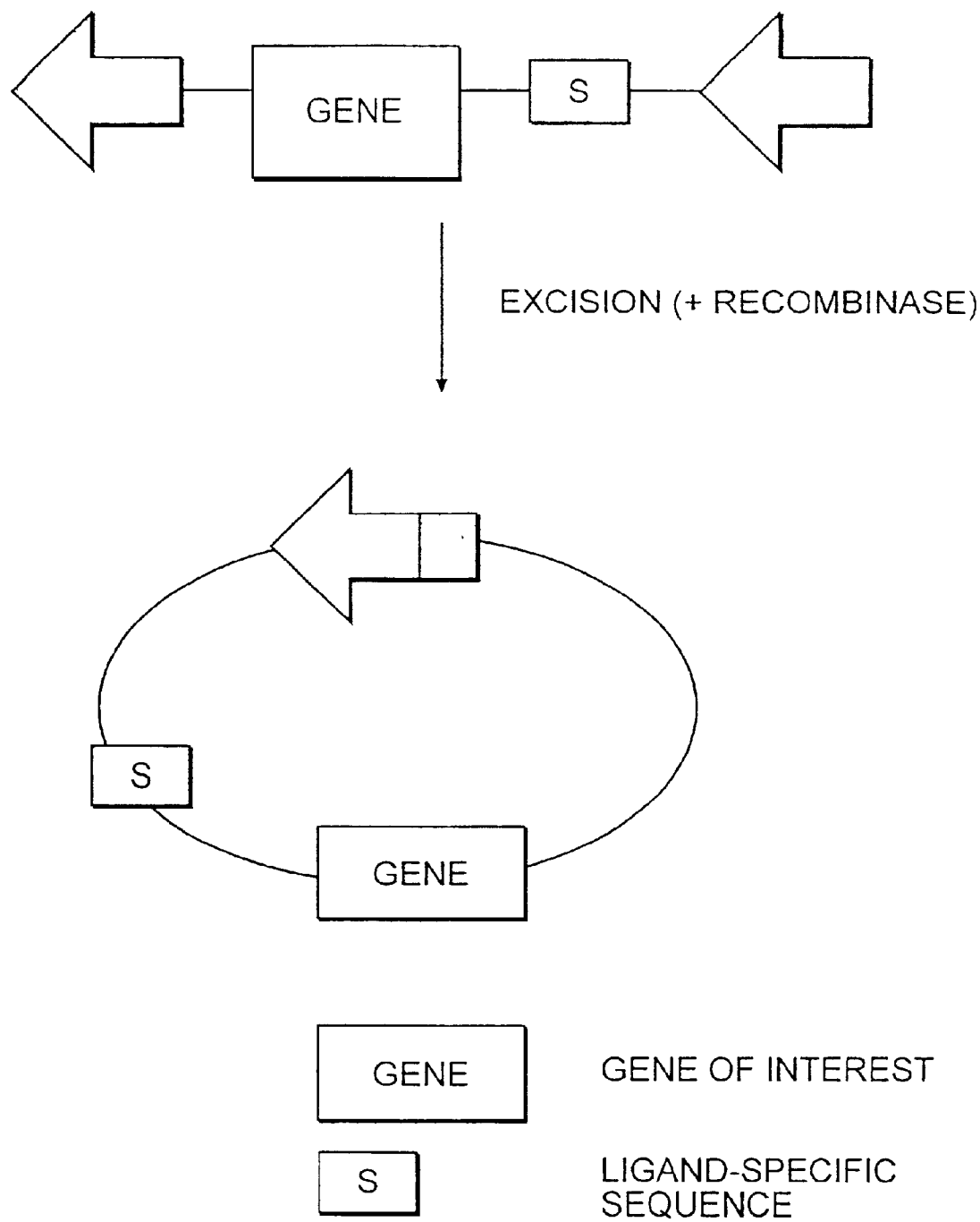
FIG. 3: Production of a minicircle containing a sequence specific to a ligand.

The standard methods of molecular biology, such as centrifugation of plasmid DNA in a cesium chloride-ethidium bromide gradient, digestion with restriction enzymes, gel electrophoresis, electroelution of DNA fragments from agarose gels, transformation in *E. coli*, precipitation of nucleic acids, and the like, are described in the literature (Maniatis et al., Molecular Cloning: A Laboratory Manual, 3$^{rd}$ Edition. Cold Spring Harbor Laboratory, Cold Spring Harbor Laboratory Press, New York, 2000; Ausubel et al., Current Protocols in Molecular Biology. John Wiley and Sons, New York, 2001). Nucleotide sequences were determined by the chain termination method according to the protocol already put forward (Ausubel et al., 2001, supra).

Restriction enzymes were supplied by New-England Biolabs (Biolabs), Bethesda Research Laboratories (BRL) or Amersham Ltd. (Amersham).

To carry out ligations, DNA fragments were separated according to their size on 0.7% agarose or 8% acrylamide gels, purified by electrophoresis, and, then, electroeluted, extracted with phenol, precipitated with ethanol, and incubated in a buffer comprising 50 mM Tris-HCl, pH 7.4, 10 mM MgCl$_2$, 10 mM DTT, 2 mM ATP in the presence of phage T4 DNA ligase (Biolabs). Oligonucleotides were synthesized using phosphoramidite chemistry with the latter derivatives protected at the b position by a cyanoethyl group (Sinha et al., Acids Res. 12: 4539–4557, 1984; Giles J. W., Am. Biotechnol. November/December, 1985), with the Biosearch 8600 automatic DNA synthesizer, using the manufacturer's recommendations.

The ligated DNAs were used to transform the following strains rendered competent: *E. coli* MC1060 [(LacIOPZYA) X74, galU, galK, strA', hsdR] (Casadaban et al., Meth. Enzymol. 100: 293–308, 1983); HB101 [hsdS20, supE44, recA13, ara-14, proA2, lacY1, galK2, rpsL20, xyl-5, mtl-1, λ-, F-] (Maniatis et al., 1989); and DH5α [endA1 hsdR17 supE44 thi-1 recA1 gyrA96 relA1 λ-φ80 lacZΔM15] for the plasmids.

LB and 2XYT culture media were used for the bacteriological part (Maniatis et al., 2001, supra).

Plasmid DNAs were purified according to the alkaline lysis technique (Maniatis et al., 2001, supra.

Definition of the Terms Employed and Abbreviations

Recombinant DNA: set of techniques which make it possible either to combine, within the same microorganism, DNA sequences which are not naturally combined or to mutagenize a DNA fragment specifically, or the nucleic acids resulting from the use of these techniques.

ATP: adenosine 5'-triphosphate

BSA: bovine serum albumin

PBS: 10 mM phosphate buffer, 150 mM NaCl, pH 7.4 dNTP: 2'-deoxyribonucleoside 5'-triphosphates

DTT: dithiothreitol kb: kilobases pairs bp: base pairs mSeAP: murine secreted alkaline phosphate

EXAMPLES

Example 1

Construction of a Plasmid Carrying the attP and attB Sequences of the Bacteriophage in Repeated Direct Orientations The plasmid pNH16a was used as starting material, since it already contains a fragment of bacteriophage λ carrying the attP sequence (Hasan et al., Gene, 56:145–151, 1987). This plasmid was digested with EcoRI. Oligonucleotides that contain the attB sequence (Landy, Ann. Rev. Biochem. 58: 913–949, 1989) were synthesized. They have the following sequence:

Oligonucleotide 5476 (SEQ ID No. 1):
5'-AATTGTGAAGCCTGCTTTTTTATACTAACTTGAGCGG-3'

Oligonucleotide 5477 (SEQ ID No. 2):
5'-AATTCCGCTCAAGTTAGTATAAAAAAGCAGGCTTCAC-3'

They were hybridized to re-form the attB sequence and then ligated at the EcoRI site of the 4.2-kb EcoRI fragment of pNH16a (Hasan et al., 1987, supra). After transformation of DH5α, a recombinant clone was isolated. The plasmid thereby constructed was designated pXL2648 (see FIG. 4). This plasmid contains the attP and attB sequences of the bacteriophage in the direct orientation. Under the action of the integrase of the bacteriophage (Int protein), there should be excision of the sequences lying between the two att sites. This results in separation of the material inserted between the two att sequences from the origin of replication and from the resistance marker of the plasmid, which are positioned on the outside.

Example 2

Obtaining a Minicircle in vivo in *Escherichia coli*

Figure 4:
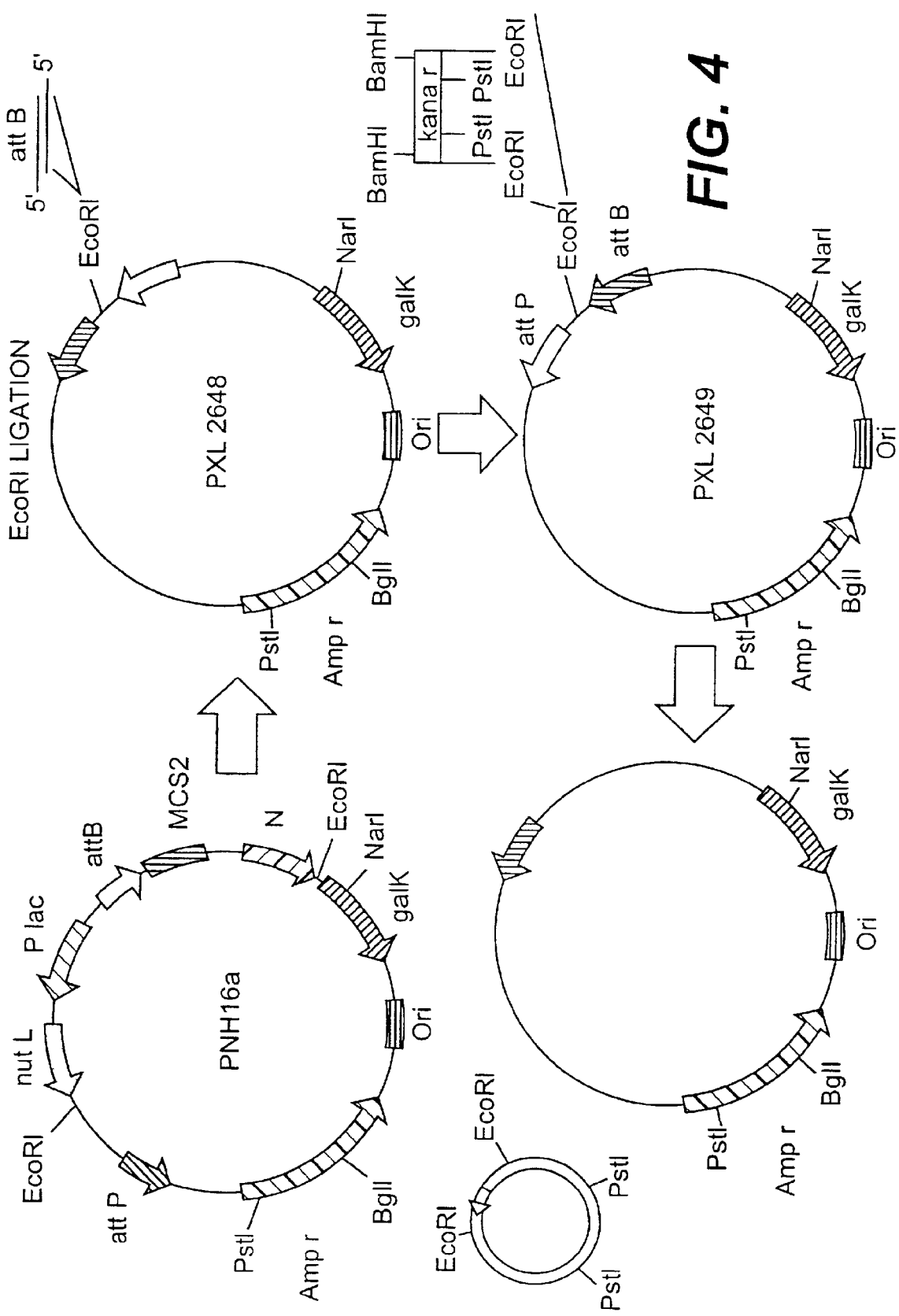
FIG. 4: Construction of pXL2649. Ori: Origin of replication; Kana$^r$: Marker gene conferring resistance to kanamycin; Amp$^r$: Marker gene conferring resistance to ampicillin; galK: Galactosidase gene of *E. coli;* Plac: Promoter of the lactose operon.

A cassette for resistance to kanamycin was cloned at the EcoRI site of plasmid pXL2648 (FIG. 4). This cassette originates from the plasmid pUC4KIXX (Pharmacia Biotech.). For this purpose, 10 μg of plasmid pUC4KIXX were digested with EcoRI and then separated by agarose gel electrophoresis; the 1.6-kb fragment containing the kanamycin resistance marker was purified by electroelution and ligated to plasmid pXL2648 linearized with EcoRI. The recombinant clones were selected after transformation into *E. coli* DH5α and selection for resistance to kanamycin. The expected restriction profile was observed on one clone; this plasmid clone was designated pXL2649 (FIG. 4). This plasmid was introduced by transformation into two *E. Coli* strains:

D1210 [hsdS20, supE44, recA13, ara-14, proA2, lacY1, galK2, rpsL20, xyl-5, mtl-1, λ⁻, F-, lacIq] (Sadler et al., Gene, 8:279–300,1980); and D1210HP, which corresponds to DH1210 lysogenized with the phage xis⁻ (Xis⁻Kil⁻) cI857 (Podjaska et al, 1985). The strain D1210HP[supE44 ara-14 galK2 Δ(gpt-proA)62 rpsL20 xyl5 mtl1 recA13 Δ(mcrC-mrr) hsdS lacI$^q$] (λ[cI857 xis⁻kil⁻]), accession number I-2314, was deposited on Sep. 15, 1999, with the Collection National de Cultures de Microorganisms (CNCM), Institut Pasteur, 25 rue du Docteur Roux, F-75724 Paris Cédex 15, FRANCE.

The transformants were selected at 30° C. on 2× YT medium with kanamycin (50 mg/l). After re-isolation on selective medium, the strains were inoculated into 5 ml of LB medium supplemented with kanamycin (50 mg/l). After 16 h of incubation at 30° C. with agitation (5 cm of rotational amplitude), the cultures were diluted ¹⁄₁₀₀ into 100 ml of the same medium. These cultures were incubated under the same conditions until an $OD_{610}$ of 0.3 was reached. At this point, half of the culture was removed and incubated for 10 min at 42° C. to induce the lytic cycle of the phage and the expression of the integrase. After this incubation, the cultures were transferred again to 30° C. and incubated for 1 h under these conditions. Next, culturing was stopped and minipreparations of plasmid DNA were produced. Regardless of the conditions, in the strain D1210, the agarose gel electrophoresis profile of the undigested plasmid DNA of plasmid pXL2649 was unchanged, as also was the case in the strain D1210HP which has not been thermally induced. On the contrary, in D1210HP which has been incubated for 10 min at 42° C. and then cultured for 1 hour at 30° C., it was found that there was no longer a plasmid, but instead two circular DNA molecules: one of low molecular weight, migrating faster and containing an EcoRI site; and one of higher molecular weight, containing a unique BglI site, as expected. Hence, there has indeed been excision of the sequences present between the two att sequences, and generation of a minicircle bereft of any origin of replication. This supercoiled circular DNA not carrying an origin of replication is termed a minicircle. This name takes, in effect, better account of the circular nature of the molecule. The starting plasmid pXL2649 is present, but represents approximately 10% of the plasmid which has excised the sequences flanked by att.

The minicircle may then be purified by standard techniques of plasmid DNA purification, since it is supercoiled like plasmid DNA. These techniques comprise, inter alia, purification on a cesium chloride density gradient in the presence of ethidium bromide, or, alternatively, the use of anion exchange columns (Maniatis et al., 2001, supra). In addition, if the plasmid DNA corresponding to the origin of replication and to the selectable marker is considered to be present in an excessively large amount, it is always possible, after purification, to use one or more restriction enzymes that will digest the plasmid and not the minicircle, enabling them to be separated by techniques that separate supercoiled DNA from linear DNA, such as in a cesium chloride density gradient in the presence of ethidium bromide (Maniatis et al., 2001, supra).

Example 3

Obtaining a Minicircle Containing a Cassette for the Expression of Luciferase

In order to test the use of these minicircles in vivo, a reporter gene with the sequences required for its expression was cloned into plasmid pXL2649 (see Example 2). This was done using a 3150-bp BglII-BamHI cassette originating from pGL2-Control (Promega Biotech), which contains the SV40 early promoter, the enhancer of the SV40 early promoter, the luciferase gene of *Photinus pyralis* and a polyadenylation site derived from SV40. The 3150-bp BglII-BamHI fragment was cloned at the BamHI site of pXL2649 digested with BamHI so as to replace the cassette for resistance to kanamycin by the cassette for the expression of luciferase from pGL2-Control. The plasmid thus constructed was called pXL2650. In this plasmid, the attP and attB sites flank the cassette for the expression of luciferase. Site-specific recombination enables only the sequences required for the expression of luciferase together with the luciferase gene to be excised. This recombination may be carried out exactly as described in Example 2. A minicircle such as plasmid pXL2650 may be used thereafter in in vivo or in vitro transfection experiments.

A 1-liter culture of the strain D1210HP pXL2650 in 2×YT medium supplemented with ampicillin (50 mg/ml) was set up at 30° C. At an $OD_{610}$ equal to 0.3, the culture was transferred to 42° C. for 20 min, then replaced for 20 min at 30° C. The episomal DNA was prepared by the alkaline lysate technique (Maniatis et al., 1989), followed by a cesium chloride density gradient supplemented with ethidium bromide (Maniatis et al., 2001, supra), then by an extraction of the ethidium bromide with isopropanol and by dialysis. This DNA was shown to contain the minicircle. One hundred micrograms of this preparation were digested with PstI, and the reaction was subjected to a cesium chloride density gradient supplemented with ethidium bromide (Maniatis et al., 1989). An identical result is obtained when the preparation is digested jointly with AlwNI and XmnI. The supercoiled form was recovered and, after removal of the ethidium bromide (Maniatis et al., 2001 supra), was found to correspond only to the minicircle, lacking an origin of replication and any marker gene. This minicircle preparation may be used for in vitro and in vivo transfection experiments.

Example 4

In vitro Transfection of Mammalian Cells, and more Especially of Human Cells, With a Minicircle The minicircle DNA containing the luciferase gene of *Photinus pyralis* as described in Example 3, that is to say corresponding to the minicircle generated from plasmid pXL2650, is diluted in 150 mM NaCl and mixed with a transfectant. It is possible to use various commercial transfectants, such as dioctadecylamidoglycylspermine (DOGS, Transfectam™, Promega), Lipofectin™ (Gibco-BRL), and the like, in different positive/negative charge ratios. By way of illustration, the transfecting agent was used in charge ratios greater than or equal to 3. The mixture is vortexed, left for 10 minutes at room temperature, diluted in culture medium without fetal calf serum, and then added to the cells in the proportion of 2 µg of DNA per culture well. The cells used are Caco-2, derived from a human colon adenocarcinoma, cultured according to a protocol described (Wils et al., et al., Biochem. Pharmacol. 48: 1528–153, 1994) and inoculated on the day before the experiment into 48-well culture plates in the proportion of 50,000 cells/well. After two hours at 37° C., 10% v/v of fetal calf serum is added and the cells are incubated for 24 hours at 37° C. in the presence of 5% $CO_2$. The cells are washed twice with PBS and the luciferase activity is measured according to the protocol described (such as the Promega kit). It is possible to use other lines (fibroblasts, lymphocytes, etc.) originating from different species, or alternatively cells taken from an individual (fibroblasts, keratinocytes, lymphocytes, etc.) and which will be reinjected into him or her after transfection.

Example 5

In vitro Transfection of NIH 3T3 Cells

Figure 5:
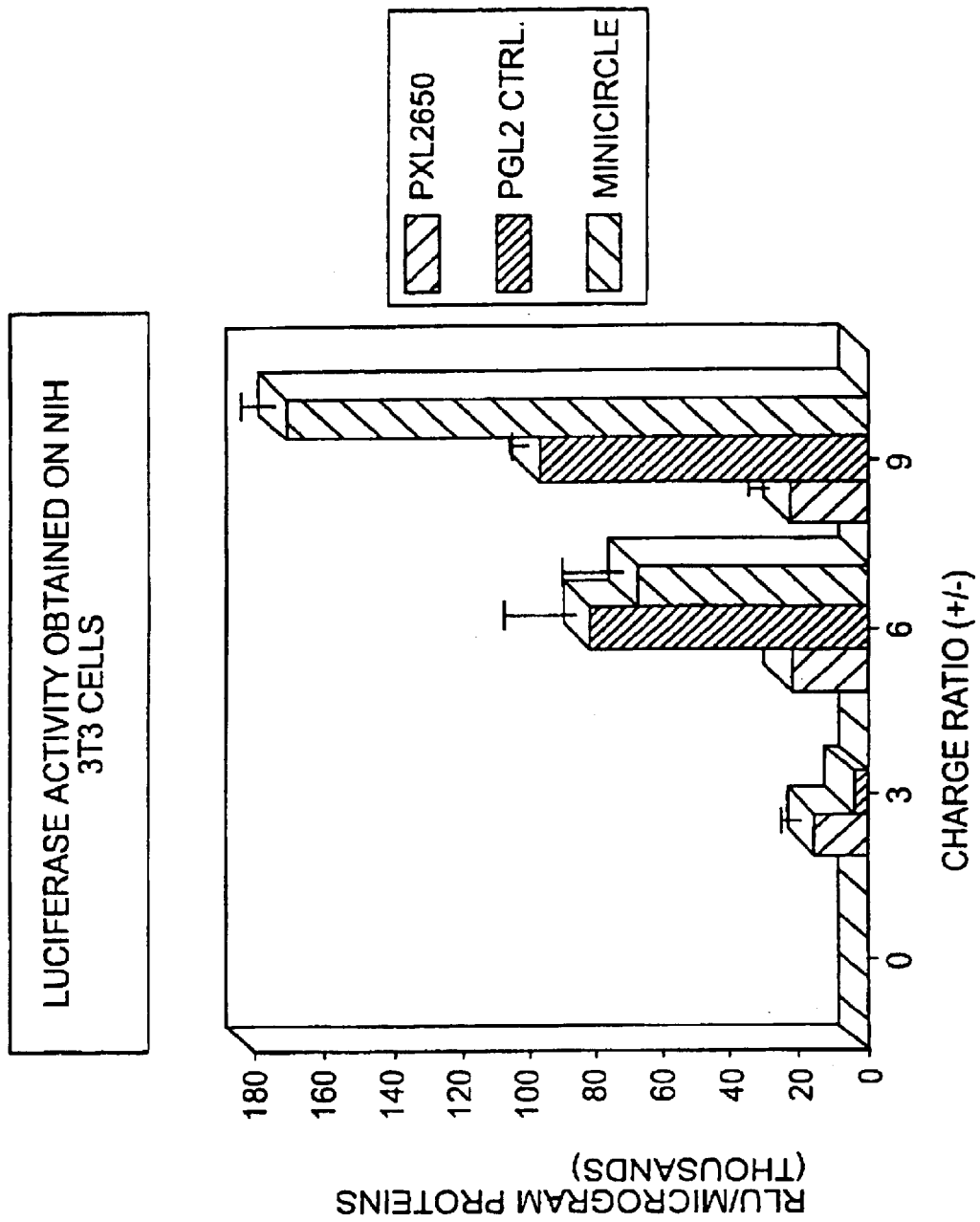
FIG. 5: Luciferase activity obtained after transfection of NIH3T3 mouse fibroblasts with plasmid pXL2650, the minicircle generated from plasmid pXL2650 and PGL2-Control (Promega Biotech). The transfection was carried out under the following conditions: 0.5 mg of DNA per well, 50,000 cells per well. The lipofectant used is RPR 115335. The result is recorded in RLU per microgram of proteins as a function of the lipofectant/DNA charge ratio.
Figure 6:
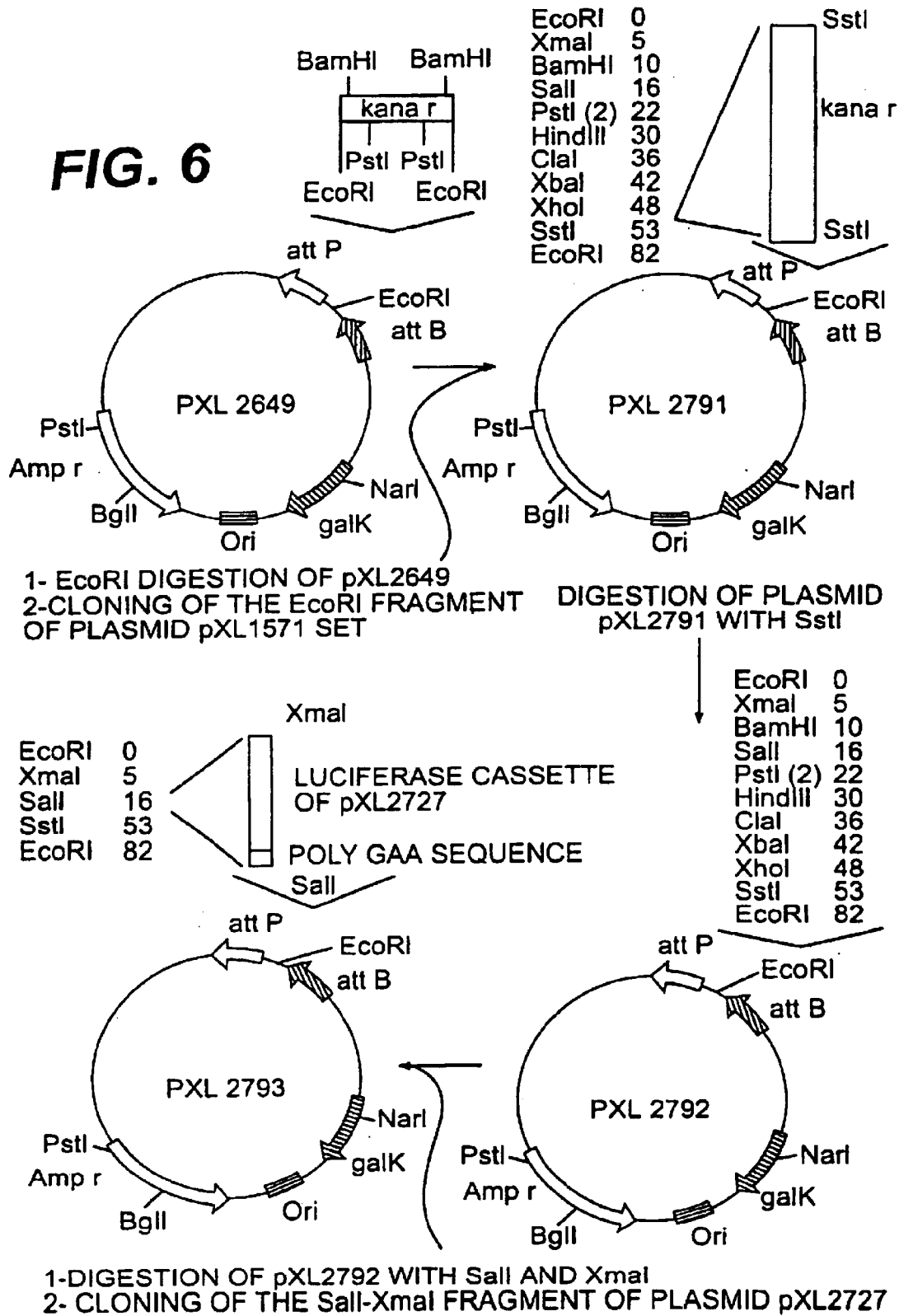
FIG. 6: Construction of the plasmid pXL2793. This plasmid generates, after recombination, a minicircle containing a synthetic homopurine-homopyrimidine sequence and the luciferase cassette of pXL2727.

The minicircle DNA containing the luciferase gene of *Photinus pyralis*, as described in Example 3, that is to say corresponding to the minicircle generated from plasmid pXL2650, was transfected in vitro into mammalian cells; pXL2650 and PGL2-Control (Promega Biotech.), which contain the same expression cassette, were used as control. The cells used were NIH 3T3 mouse fibroblasts, inoculated on the day before the experiment into 24-well culture plates in the proportion of 50,000 cells per well. The plasmid was diluted in 150 mM NaCl and mixed with the lipofectant RPR115335. However, it is possible to use various other commercial agents such as dioctadecylaminoglycylspermine (DOGS, Transfectam™, Promega) (Demeneix et al., Int. J. Dev. Biol. 35: 481, (1991), Lipofectin™ (Gibco-BRL) (Fegner et al., Proc. Natl. Acad. Sci. USA 84: 7413, 1987) and the like. A positive charge of the lipofectant/negative charge of the DNA ratio equal to or greater than 3 is used. The mixture was vortexed, left for ten minutes at room temperature, diluted in medium without fetal calf serum, and then added to the cells in the proportion of 0.5 mg of DNA per culture well. After two hours at 37° C., 10% by volume of fetal calf serum was added and the cells were incubated for 48 hours at 37° C. in the presence of 5% $CO_2$. The cells were washed twice with PBS and the luciferase activity was measured according to the protocol described (Promega kit, Promega Corp., Madison, Wis.), on a Lumat LB9501 luminometer (EG and G Berthold, Evry). The transfection results corresponding to the conditions which have just been stated are presented in FIG. 5. They show unambiguously that the minicircle has the same transfection properties as plasmids possessing an origin of replication. Thus, these minicircles can be used in the same way as standard plasmids in gene therapy applications.

Example 6

Affinity Purification of a Minicircle Using a Triple-Helix Interaction

This example describes a method for purifying a minicircle according to the invention from a mixture containing the plasmid form that has excised it, by triple-helix type interactions with a synthetic DNA sequence carried by the minicircle to be purified. This example demonstrates how the technology of purification by triple-helix formation may be used to separate a minicircle from a plasmid form which has excised it.

6-1. Obtaining a Minicircle Containing a Synthetic Homopurine-homopyrimidine Sequence 6-1.1. Insertion of a Homopurine-homopyrimidine Sequence into Plasmid pXL2650

Plasmid pXL2650 has a unique BamHI site immediately after the cassette containing the luciferase gene of *Photinus pyralis*. This unique site was used to insert the following two oligonucleotides:

4957 (SEQ ID No. 20): 5'-GATCCGAAGAAGAAGAAGAAGAAGAAGAAGAAGAAGAAGAAGAAGAAGAAGAAGAAC-3'

4958 (SEQ ID No. 21): 5'-GATCGTTCTTCTTCTTCTTCTTCTTCTTCTTCTTCTTCTTCTTCTTCTTCTTCTTCG-3'

These oligonucleotides, when hybridized and cloned into plasmid pXL2650, introduce a homopurine-homopyrimidine sequence $(GAA)_{17}$, as described above.

To carry out this cloning, the oligonucleotides were first hybridized in the following manner. One microgram of each of these two oligonucleotides was combined in 40 µl of a final buffer comprising 50 mM Tris-HCl, pH 7.4, 10 mM $MgCl_2$. This mixture was heated to 95° C. and then placed at room temperature so that the temperature would fall slowly. Ten nanograms of the mixture of hybridized oligonucleotides were ligated to 200 ng of plasmid pXL2650, which had been linearized with BamHI, in a final volume of 30 µl. After ligation, an aliquot was used to transform *E. coli* DH5. The transformation mixtures were plated out on LB medium supplemented with ampicillin (50 mg/l). Twenty-four clones were selected and digested with PflMI and BamHI. One clone was found which had the size of the 950-bp PflMI-BamHI fragment increased by 50 bp. This clone was selected and designated pXL2651.

Plasmid pXL2651 was purified using the Wizard Megaprep kit (Promega Corp., Madison, Wis.) according to the supplier's recommendations.

6-1.2. Insertion of a Homopurine-homopyrimidine Sequence into Plasmid pXL2649 a) Insertion of New Restriction Sites on Each Side of the Kanamycin Cassette of pXL2649.

Plasmid pXL2649, as described in Example 2, was digested with EcoRI so as to take out the kanamycin cassette originating from plasmid pUC4KIXX (PharmaciaBiotech, Uppsala, Sweden). For this purpose, 5 μg of plasmid pXL2649 were digested with EcoRI. The 4.2 kb fragment was separated by agarose gel electrophoresis and purified by electroelution.

In addition, the plasmid pXL1571 was used. The latter was constructed from the plasmid pFR10 (Gene 25: 71–88, 1983), into which the 1.6 kb fragment originating from pUC4KIXX, comprising the kanamycin gene, was inserted at the SstI site. This procedure inserted 12 new restriction sites on each side of the kanamycin gene.

Five micrograms of pXL1571 were digested with EcoRI. The 1.6 kb fragment corresponding to the kanamycin gene was separated by agarose gel electrophoresis, purified by electroelution, and ligated to the 4.2 kb EcoRI fragment of pXL2649. The recombinant clones were selected after transformation into E. coli DH5a and selection for resistance to kanamycin and to ampicillin. The expected restriction profile was observed on one clone; this plasmid clone was designated pXL2791.

b) Extraction of the Kanamycin Cassette from Plasmid pXL2791

Plasmid pXL2791 was digested with SstI to excise the kanamycin cassette. The 4.2 kb fragment was separated by agarose gel electrophoresis and purified with the Jetsorb extraction gel kit (Genomed). It was then ligated. The recombinant clones were selected for resistance to ampicillin after transformation into E. coli DH5a. The expected restriction profile was observed on one clone. This plasmid clone was designated pXL2792. This clone comprises, inter alia, SalI and XmaI restriction sites between the attP and attB sites.

c) Cloning of a Homopurine-homopyrimidine Sequence as Well as of a Cassette Permitting the Expression of Luciferase Between the Two attP and attB Sites of Plasmid pXL2792

Plasmid pXL2727 was used. This plasmid, digested with XmaI and SalI, releases a fragment comprising the following: the CMV promoter, the luciferase gene of Photinus pyralis, a polyadenylation site derived from SV40, and a homopurine-homopyrimidine sequence. The latter was obtained after hybridization and cloning of the following two oligonucleotides:

6006 (SEQ ID No. 22): 5'-GATCTGAAGAAGAAGAAGAAGAAGAAGAAGAAGAAGAAGAAGAAGAAGAAGAAGAACTGCAGATCT-3'

6008 (SEQ ID No. 23): 5'-GATCAGATCTGCAGTTCTTCTTCTTCTTCTTCTTCTTCTTCTTCTTCTTCTTCTTCTTCTTCTTCTTCTTCTTCTTCTTCTTCTTCTTCTTCTTCTTCTTCTTCTTCTTCTTA-3'

The homopurine-homopyrimidine sequence present in pXL2727 was sequenced by the Sequenase Version 2.0 method (United States Biochemical Corporation). The result obtained showed that the homopurine-homopyrimidine sequence actually present in plasmid pXL2727 contains 10 repeats (GAA-CTT), and not 17 as the sequence of the oligonucleotides 6006 and 6008 suggested would be the case. The sequence actually present in plasmid pXL2727, read after sequencing on the strand corresponding to the oligonucleotide 6008, is as follows:

5'-GATCAGATCTGCAGTCTCTTCTTCTTCTTCTTCTTCTTCTTCTTCTTCTCTTCTCA-3' (SEQ ID No. 24)

One microgram of pXL2727 was digested with XmaI and SalI. The 3.7 kb fragment was separated by agarose gel electrophoresis and purified with the Jetsorb extraction gel kit (Genomed). In addition, 1.7 μg of pXL2792 were digested with XmaI and SalI. The 4.2 kb fragment was separated on agarose gel, purified with the Jetsorb extraction gel kit (Genomed), and ligated with the 3.7 kb XmaI-SalI fragment of pXL2727. The recombinant clones were selected after transformation into E. coli DH5a and selection for resistance to ampicillin. The expected restriction profile was observed on one clone; this clone was designated pXL2793. Plasmid pXL2793 was purified using a cesium chloride density gradient according to a method already described (Maniatis et al., 2001 supra).

6-2. Preparation of the Column Enabling Triple-helix Type Interactions with a Homopurine-Homopyrimidine Sequence Present in the Minicircle to be Effected The column was prepared in the following manner:

The column used was a 1-ml HiTrap column activated with NHS (N-hydroxysuccinimide, Pharmacia), connected to a peristaltic pump (flow rate<1 ml/min). The specific oligonucleotide used has an $NH_2$ group at the 5' end.

For plasmid pXL2651, the oligonucleotide sequence was as follows:

5'-GAGGCTTCTTCTTCTTCTTCTTCTT-3' (SEQ ID No.15)

For plasmid pXL2793, the oligonucleotide sequence was as follows:

5'-CTTCTTCTTCTTCTTCTTCTT-3' (SEQ ID No. 25)

The buffers used were the following:

Coupling buffer: 0.2 M $NaHCO_3$, 0.5 M NaCl, pH 8.3.

Washing Buffer:
  Buffer A: 0.5 M ethanolamine, 0.5 M NaCl, pH 8.3.
  Buffer B: 0.1 M acetate, 0.5 M NaCl, pH 4.

Fixing and Eluting Buffer:
  Buffer F: 2 M NaCl, 0.2 M acetate, pH 4.5.
  Buffer E: 1 M Tris-HCl, pH 9, 0.5 mM EDTA.

The column was prepared in the following manner:

The column was washed with 6 ml of 1 mM HCl, and the oligonucleotide diluted in the coupling buffer (50 nmol in 1 ml) was then applied to the column and left for 30 minutes at room temperature. The column was washed with 3 ml of coupling buffer, then with 6 ml of buffer A, followed by 6 ml of buffer B. The latter two buffers were applied three times in succession to the column. In this way, the oligonucleotide was linked covalently to the column via a CONH link. The column was stored at 4° C. in PBS, 0.1% $NaN_3$.

6-3. Purification of a Minicircle Containing a Synthetic Homopurine-homopyrimidine Sequence by a Triple-helix Type Interaction 6-3.1. Purification of Plasmid pXL2651

Plasmid pXL2651 was introduced into the strain D1210HP. This recombinant strain [D1210HP (pXL2651)] was cultured as described in Example 3 to generate the minicircle containing the luciferase gene of *Photinus pyralis*. Twenty milliliters of culture were removed and centrifuged. The cell pellet was taken up in 1.5 ml of 50 mM glucose, 25 mM Tris-HCl, pH 8,10 mM EDTA. Lysis was carried out with 2 ml of 0.2 M NaOH, 1% SDS, and neutralization with 1.5 ml of 3 M potassium acetate, pH 5. The DNA was then precipitated with 3 ml of 2-propanol, and the pellet was dissolved in 0.5 ml of 0.2 M sodium acetate, pH 5, 0.1 M NaCl and loaded onto an oligonucleotide column that can form triple-helix type interactions with the poly(GAA) sequences contained in the minicircle, as described above. After the column has been washed beforehand with 6 ml of buffer F, the solution containing the minicircle to be purified was incubated, after being applied to the column, for two hours at room temperature. The column was washed with 10 ml of buffer F and elution was then performed with buffer E.

Purified DNA corresponding to the minicircle was thereby obtained. The minicircle obtained, analyzed by agarose gel electrophoresis and ethidium bromide staining, takes the form of a single band of supercoiled circular DNA. Less than 5% of starting plasmid pXL2651 was left in the preparation.

6-3.2. Purification of Plasmid pXL2793

The 7.9-kb plasmid pXL2793 was introduced into the strain D1210HP. This recombinant strain was cultured as described in Example 3, to generate the 4-kb minicircle containing the luciferase gene of *Photinus pyralis* and a 3.9-kb plasmid. Two hundred milliliters of culture were removed and centrifuged. The cell pellet was treated with the Wizard Megaprep kit (Promega Corp., Madison, Wis.) according to the supplier's recommendations. The DNA was taken up in a final volume of 2 ml of 1 mM Tris, 1 mM EDTA, pH 8. Two hundred and fifty microliters of this plasmid sample were diluted with buffer F in a final volume of 2.5 ml. The column was washed beforehand with 6 ml of buffer F. The whole of the diluted sample was loaded onto an oligonucleotide column capable of forming triple-helix type interactions with the poly(GAA) sequences contained in the minicircle, prepared as described above. After washing with 10 ml of buffer F, elution is performed with buffer E. The eluted sample was recovered in 1 ml fractions.

Figure 7:
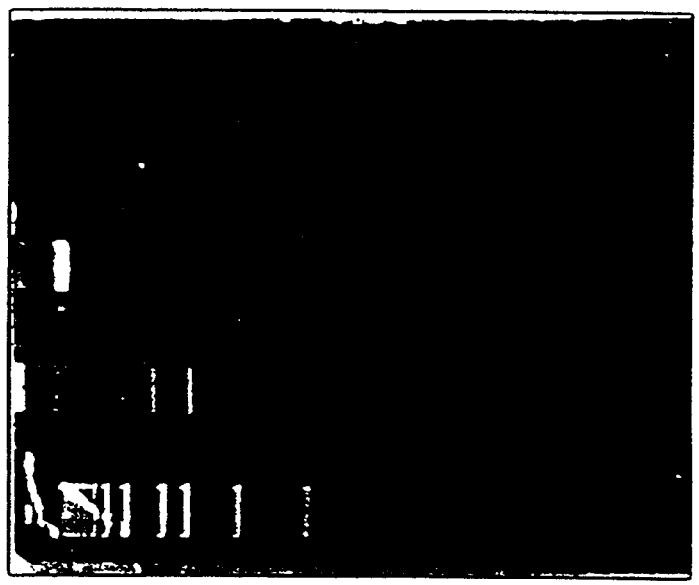
FIG. 7: Well 1 corresponds to the SalI digestion of the fraction eluted after purification with a triple-helix column. Well 2 corresponds to the XmnI digestion of the fraction eluted after purification with a triple-helix column. Well 3 corresponds to the undigested fraction eluted after purification with a triple-helix column. Well 4 corresponds to uninduced, undigested plasmid pXL2793. Wells 5 and 6 correspond, respectively, to the linear DNA and supercoiled DNA size markers.

By this method, purified DNA corresponding to the minicircle generated from pXL2793 was obtained. The DNA sample eluted from the column was analysed by agarose gel electrophoresis and ethidium bromide staining, and by enzyme restriction. For this purpose, the eluted fractions which were shown to contain DNA by assay at $OD_{260}$ nm were dialysed for 24 hours against 1 mM Tris, 1 mM EDTA, then precipitated with isopropanol and taken up in 200 µl of $H_2O$. Fifteen microliters of the sample thereby obtained were digested with SalI, this restriction site being present in the minicircle and not in the 3.9 kb plasmid generated by the recombination, or with XmnI, this restriction site being present in the 3.9 kb plasmid generated by the recombination and not in the minicircle. The result obtained is presented in FIG. 7, showing that the minicircle has been purified of the recombinant plasmid.

Example 7

In vivo Transfection of Mammalian Cells with a Minicircle

This example describes the transfer of a minicircle coding for the luciferase gene into the brain of newborn mice. The minicircle (30 µg) is diluted in sterile 150 mM NaCl to a concentration of 1 µg/µl. A synthetic transfectant such as dioctadecylamidoglycylspermine (DOGS) is then added in a positive/negative charge ratio less than or equal to 2. The mixture is vortexed, and 2 µg of DNA are injected into the cerebral cortex of anesthetized newborn mice using a micromanipulator and a microsyringe. The brains are removed 48 hours later, homogenized and centrifuged and the supernatant is used for the assay of luciferase by the protocols described (such as the Promega kit).

Example 8

Use of the par locus of RK2 to Reduce the Presence of Minicircle or Miniplasmid Topoisomers This example demonstrates the presence of topological forms derived i) from the plasmid possessing the attP and attB sequences in the direct orientation, ii) from the minicircle or iii) from the miniplasmid, after the action of the integrase of bacteriophage λ in *E. coli*. This example also shows that these topological or oligomeric forms may be resolved by using the par locus of RK2 (Gerlitz et al., *J. Bacteriol.* 172: 6194, 1990). In effect, this locus contains, in particular, the parA gene coding for a resolvase acting at the mrs (multimer resolution system) site (Eberl et al., Mol. Microbiol. 12: 131, 1994).

8-1. Construction of Plasmids pXL2777 and pXL2960

Plasmids pXL2777 and pXL2960 are derived from the vector pXL2776, and possess in common the minimal replicon of ColE1, the gene of the transposon Tn5 coding for resistance to kanamycin and the attP and attB sequences of bacteriophage λ in the direct orientation. These plasmids differ with respect to the genes inserted between the attP and attB sequences, in particular pXL2777 contains the omegoncassette (coding for the gene for resistance to spectinomycin) whereas plasmid pXL2960 carries the par locus of RK2.

8-1.1. Minimal Vector pXL2658

The vector pXL2658 (2.513 kb) possesses the minimal replicon of ColE1 originating from pBluescript (ori) and the gene of the transposon Tn5 coding for resistance to kanamycin (KmR) as a selectable marker. After the BsaI end has been blunted using the Klenow enzyme, the 1.15 kb BsaI-PvuII fragment of pBKS+ (obtained from Stratagene) was ligated to the 1.2 kb SmaI fragment of pUC4KIXX (obtained from Pharmacia) to generate the plasmid pXL2647. The oligonucleotides 5542 5'(AGC TTC TCG AGC TGC AGG ATA TCG AAT TCG GAT CCT CTA GAG CGG CCG CGA GCT CC)3' (SEQ ID No. 26) and 5543 5'(AGC TGG AGC TCG CGG CCG CTC TAG AGG ATC CGA ATT CGA TAT CCT GCA GCT CGA GA)3' (SEQ ID No. 27) were hybridized with one another and then cloned into the HindIII site of pXL2647; in this way pXL2658 is constructed. In this plasmid, the multiple cloning site is SstI, NotI, XbaI, BamHI, EcoRI, EcoRV, PstI, XhoI, and HindIII between the origin of replication and the gene coding for resistance to kanamycin. Plasmid pXL2675 differs from pXL2658 by the orientation of the multicloning site.

8-1.2. Vector pXL2776 Containing the attP and attB Sequences of Phase λ

Figure 8:
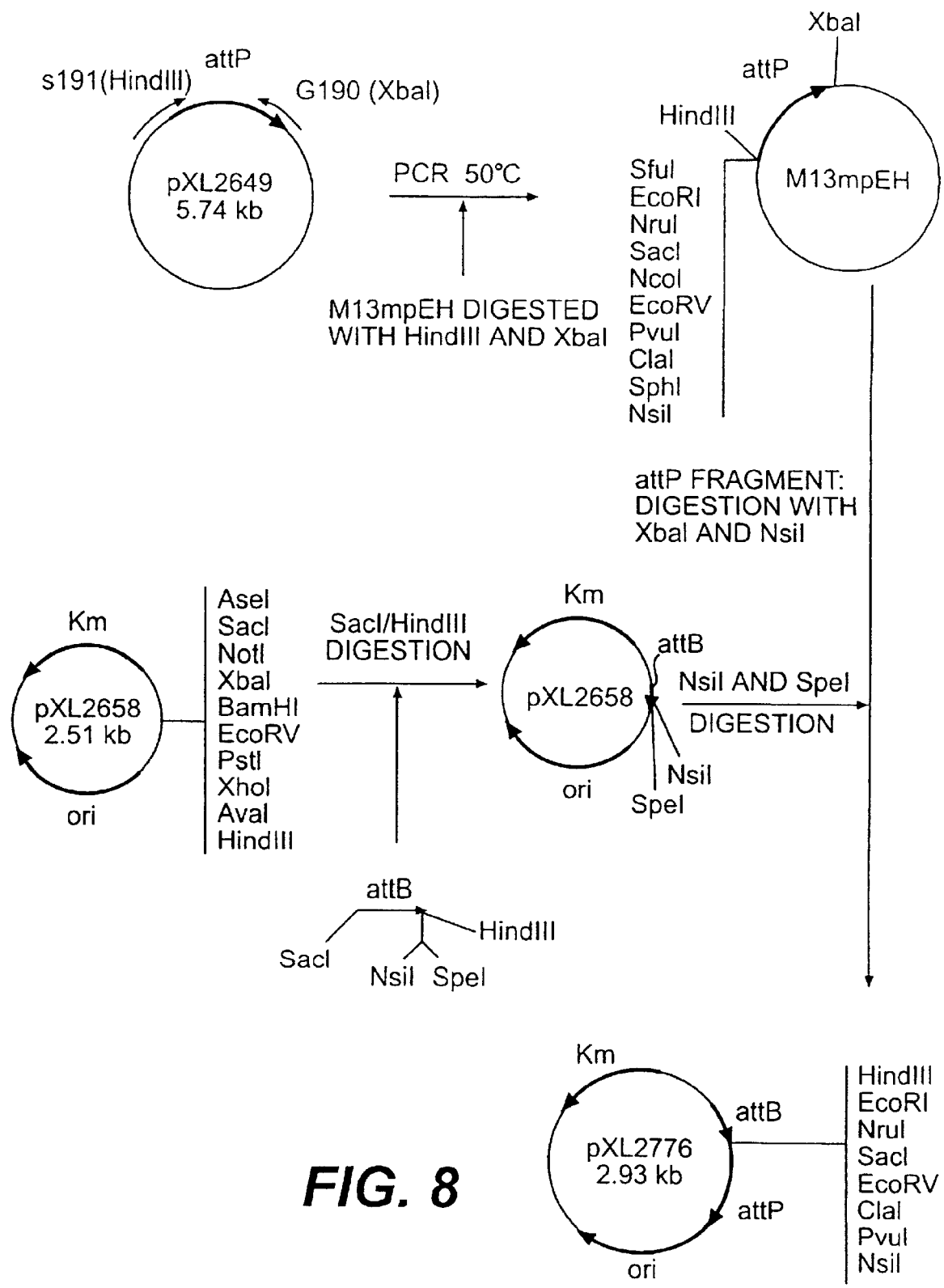
FIG. 8: Diagrammatic description of the construction of the plasmid pXL2776.

The vector pXL2776 (2.93 kb) comprises the minimal replicon of ColE1 originating from pBluescript, the gene coding for resistance to kanamycin and the attP and attB sequences of bacteriophage λ in the direct orientation as shown in FIG. 8. The 29 bp attB sequence (Mizuuchi et al., 1980 Proc. Natl. Acad. Sci. USA 77 p. 3220) was introduced between the SacI and HindIII restriction sites of pXL2658 after the sense oligonucleotide 6194: 5'-ACT AGT GGC CAT GCA TCC GCT CAA GTT AGT ATA AAA AAG CAG GCT TCA G-3' (SEQ ID No.28) has been hybridized with the antisense oligonucleotide 6195: 5'-AGC TCT GAA GCC TGC TTT TTT ATA CTA ACT TGA GCG GAT GCA TGG CCA CTA GTA GCT-3' (SEQ ID No.29) in such a way that the SacI and HindIII sites are no longer re-formed after cloning. This plasmid, the sequence of which was verified with respect to attB, is then digested with SpeI and NsiI in order to introduce the attP sequence flanked by the NsiI and XbaI restriction sites and thus to generate plasmid pXL2776. The attP sequence was obtained by PCR amplification using plasmid pXL2649 (described in Example 2) as template, the sense oligonucleotide 6190: 5'-GCG TCT AGA ACA GTA TCG TGA TGA CAG AG-3' (SEQ ID No.30) and the antisense oligonucleotide 6191: 5'-GCC AAG CTT AGC TTT GCA CTG GAT TGC GA-3' (SEQ ID No.31), and performing 30 cycles during which the hybridization temperature is 50° C. The PCR product digested at the XbaI and HindIII sites was cloned into the phage M13mpEH between the XbaI and HindIII sites. The amplified sequence is identical to the attP sequence described in Lambda II (edited by R. W. Hendrix, J. W. Roberts, F. W. Stahl, R. A. Weisberg; Cold Spring Harbor Laboratory, 1983) between positions 27480 and 27863.

8-1.3. Plasmid pXL2777

Plasmid pXL2777 (6.9 kb) comprises the minimal replicon of ColE1 originating from pBluescript, the gene coding for resistance to kanamycin, the attP and attB sequences of bacteriophage λ in the direct orientation and separated by the sacB gene coding for levansucrase of *B. subtilis* (P. Gay et al., J. Bacteriol. 153: 1424, 1983), and the Sp omegon coding for the gene for resistance to spectinomycin Sp and streptomycin Sm (P. Prentki et al., Gene 29: 303, 1984). The sacB-Sp cassette having EcoRV and NsiI cloning ends comes from the plasmid pXL2757 (FR95/01632) and was cloned between the EcoRV and NsiI sites of pXL2776 to form pXL2777.

8-1.4. Plasmid pXL2960

Plasmid pXL2960 (7.3 kb) comprises the minimal replicon of ColE1 originating from pBluescript, the gene coding for resistance to kanamycin and the attP and attB sequences of bacteriophage λ in the direct orientation and separated by i) the sacB gene coding for levansucrase of *B. subtilis* (P. Gay et al., J. Bacteriol. 153: 1424, 1983) and ii) the par locus of RK2 (Gerlitz et al., J. Bacteriol. 172: 6194, 1990). The par cassette having BamHI ends comes from the plasmid pXL2433 (PCT/FR95/01178) and was introduced between the BamHI sites of pXL2777 to generate pXL2960.

8-2. Resolution of Minicircle or Miniplasmid Topoisomers

Figure 9:
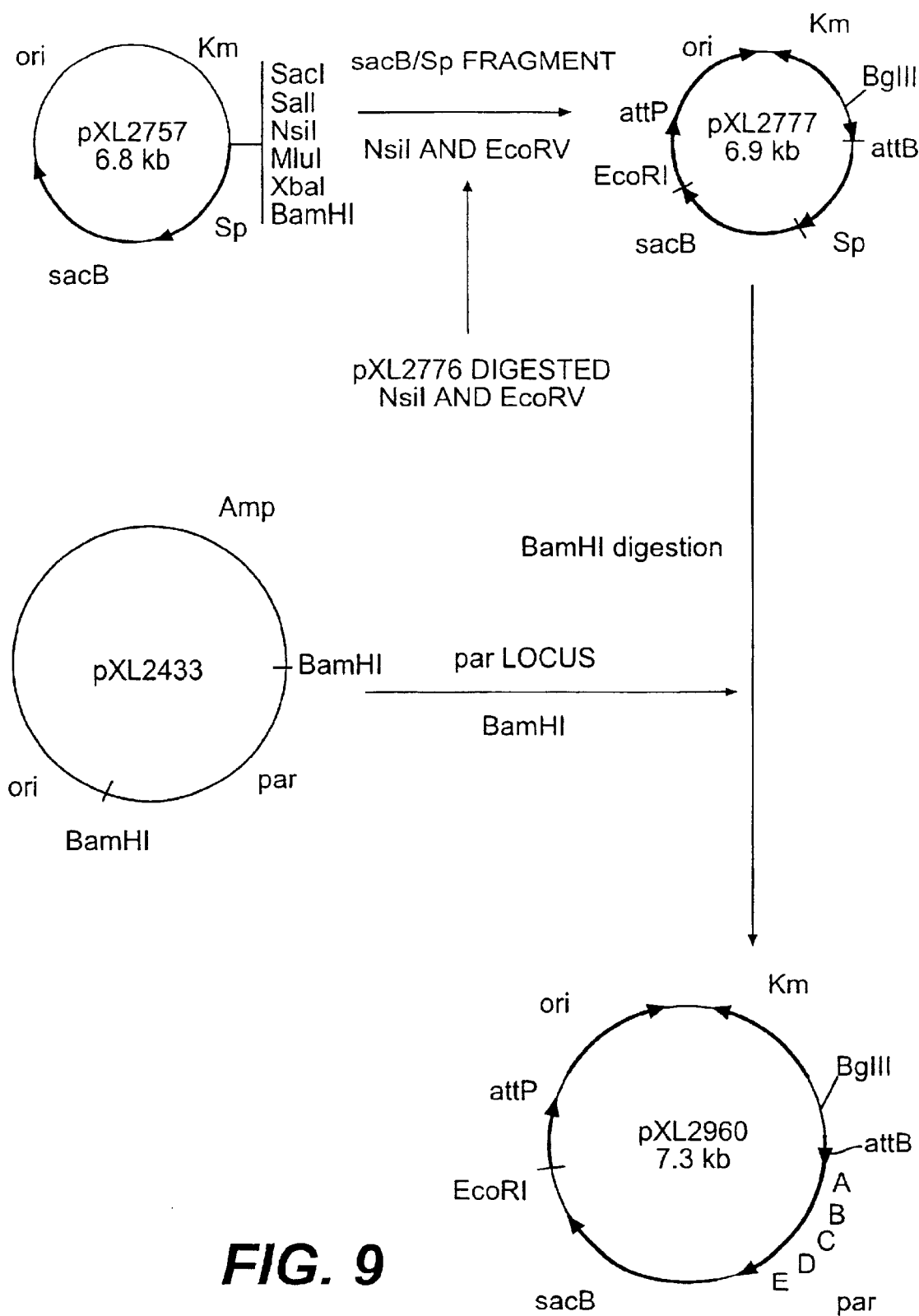
FIG. 9: Diagrammatic description of the constructions of the plasmids pXL2777 and pXL2960.
Figure 10:
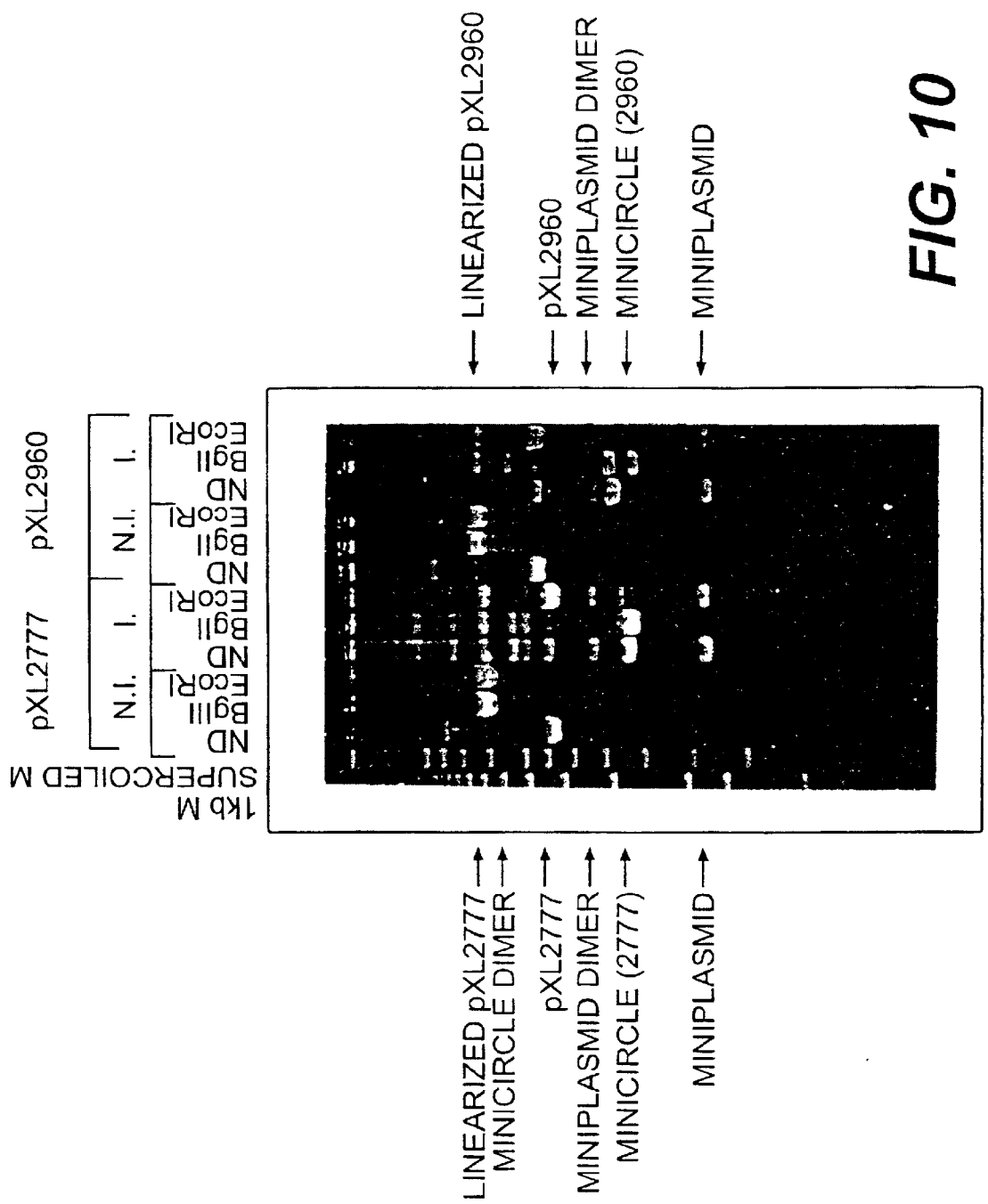
FIG. 10: Action of the integrase of bacteriophage λ in *E. coli* on plasmids pXL2777 and pXL2960. M: linear DNA or supercoiled DNA 1 kb molecular weight marker. N.I.: not induced. I: induced. N.D.: not digested.
Figure 11:
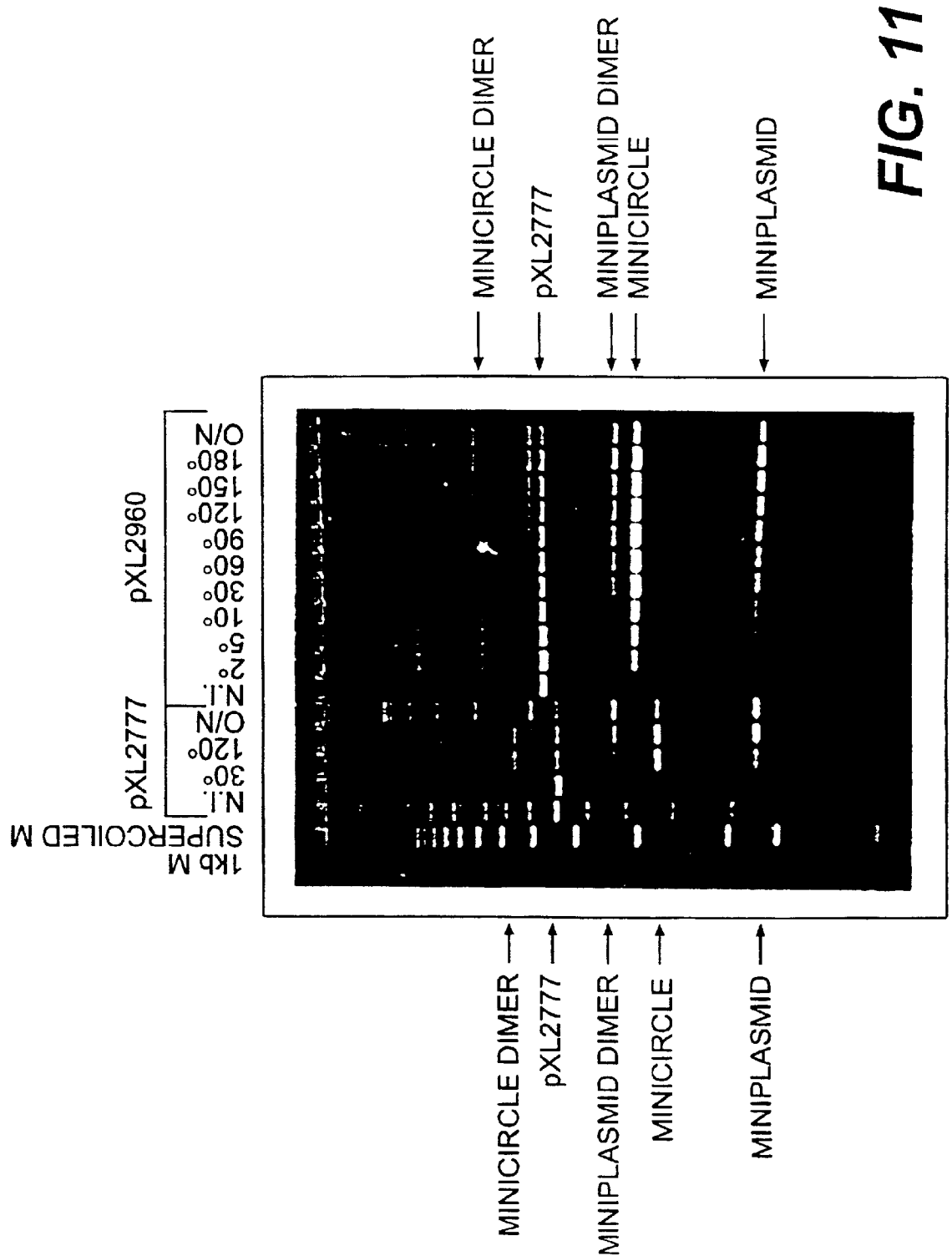
FIG. 11: Kinetics of recombination of the integrase of bacteriophage λ in *E. coli* on plasmids pXL2777 and pXL2960. 2': 2 minutes. O/N: 14 hours. M: linear DNA or supercoiled DNA 1 kg molecular weight marker. N.I.: not induced. I: induced. N.D.: not digested.

Plasmids pXL2777 and pXL2960 were introduced by transformation into *E. coli* strain D1210HP. The transformants were selected and analysed as described in Example 2, with the following modifications: the expression of the integrase was induced at 42° C. for 15 min when the optical density of the cells at 610 nm was 1.8, and the cells were then incubated at 30° C. for 30 min, see FIG. 9, or for a period varying from 2 minutes to 14 hours (O/N), see FIG. 10. The plasmid DNA originating from uninduced and induced cultures was then analysed on agarose gel before or after digestion with a restriction enzyme exclusive to the minicircle portion (EcoRI) or miniplasmid portion (BglII), see FIG. 11, or after the action of DNA topoisomerase A or the gyrase of *E. coli*. The supercoiled dimer forms of minicircle or miniplasmid are clearly revealed by i) their molecular weight, ii) their linearization by the restriction enzyme, iii) their change in topology through the action of topoisomerase A (relaxed dimer) or of the gyrase (supersupercoiled dimer), iv) specific hybridization with an internal fragment peculiar to the minicircle or the miniplasmid. Other topological forms of higher molecular weights than that of the initial plasmid originate from the initial plasmid or the minicircle or the miniplasmid, since they disappear after digestion with the restriction enzyme exclusive to the minicircle portion (EcoRI) or miniplasmid portion (BglII). These forms are much less abundant when the intial plasmid is pXL2960 than when it is pXL2777, see FIG. 10. In particular, the dimer form of minicircle is present to a not insignificant extent with plasmid pXL2777, whereas it is invisible with plasmid pXL2960 when the cells are incubated for at least 30 min at 30° C., see FIGS. 9 and 10. It should be noted that minicircle dimers are observed at the beginning of the kinetic experiment with pXL2960 (2 to 10 min), and are thereafter resolved (after 30 min), see FIG. 10. Consequently, the par locus leads to a significant reduction in the oligomeric/topological forms resulting from the action of the integrase of bacteriophage λ in *E. coli* on plasmids containing the attP and attB sequences in the direct orientation.

Example 9

Construction of a Plasmid Carrying attB and attP Sequences of the Bacteriophage in Direct Orientation 9.1 Construction of pXL3909

The preparation of DNA minicircles in the Examples above requires the rapid elevation of the bacterial culture temperature from 30° to 42° C. Although such a temperature change is readily achieved in a small scale culture, it is problematic on a larger scale because of the time required to change the temperature of a large liquid volume. The following examples use the pBAD promoter, which is rapidly induced by adding arabinose to the culture medium, in place of a temperature-sensitive promoter for regulating the expression of the λ integrase (int) with or without excisionase (xis) genes. One example is also given with plac promoter.

Plasmid pXL3909 is derived from pBKS and contains a kanamycin resistance gene (KmR), the attP sites which are present at positions 27501 to 27823 in the bacteriophage λ genome and attB sites, placed in the direct orientation. A triple helix forming sequence (5'-AAGAAAAAAAAGAA-3'; SEQ ID No. 32) is inserted between the attP and attB sites. In addition, the coding sequence of mSeAP under the control of the CMV promoter (CMV E/P −522/+74, a sequence comprising nucleotide −522 to nucleotide +74 with reference to the transcription start site, +1, of the CMV promoter) is inserted between the attP and attB sites.

Figure 12:
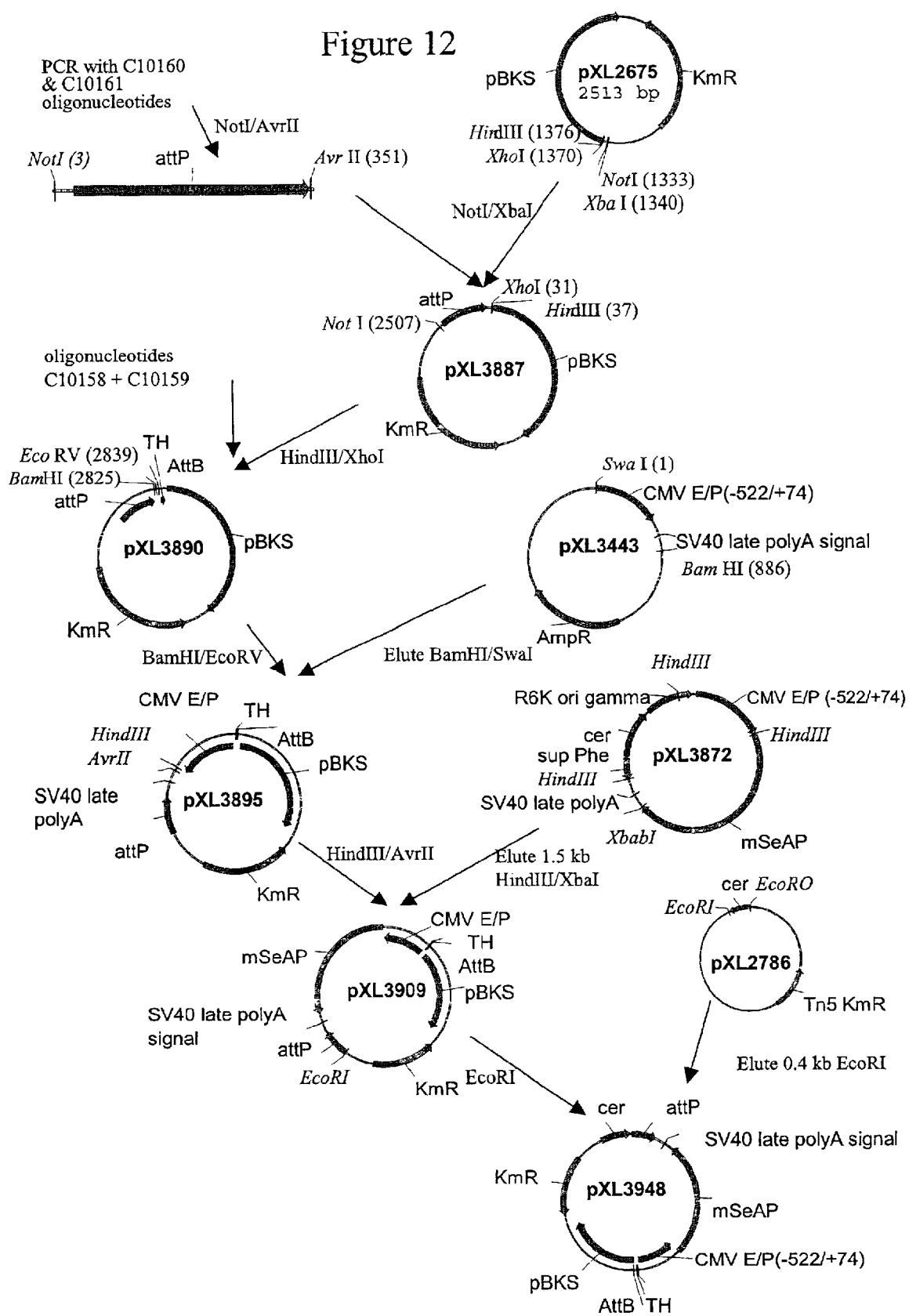
FIG. 12: Construction of pXL3909 and pXL3948.

The preparation of pXL3909 is diagrammed in FIG. 12. Briefly, the attP site present in pXL2776 was amplified by PCR using the following oligonucleotides C10160 and C10161:

5'-AAAGATCCGCGTCGACTTTGTGCTTCTCTGGAGTGC-3' (SEQ ID No. 33)

5'-AAACCTAGGAAATCAAATAATGA-3' (SEQ ID No. 34)

The resulting fragment was cloned into the plasmid pXL2675, which had been digested with NotI and XbaI to form pXL3887. The plasmids pXL2776 and pXL2675 are described in Appl. Microbiol.Biotechnol. 49: 560, 1998 and in example 8-1.2 and 8-1.1. An attB site and a triple helix-forming (TH) sequence was formed by annealing the following oligonucleotides C10158 and C10159:

5'-TCGAGTTCTTTTTTTTCTTGAAGCCTGCTTTTTTACTAACTTGAGCG-3' (SEQ ID No. 35)

5'-AGCTCGCTCAAGTTAGTATAAAAAAGCAGGCTTCAAGAAAAAAAGAAG-3' (SEQ ID No. 36)

and inserting the double-stranded product into pXL3887, which had been digested with HindIII and XhoI to form pXL3890. The CMV promoter was excised from pXL3443 using BamHI and SwaI, purified by agarose gel electrophoresis as described above, and inserted into BamHI/EcoRV-digested pXL3890 to form pXL3895. A HindIII/XbaI fragment, containing the coding sequence of the gene mSeAP (murine Secreted Phosphatase alkaline) was isolated from pXL3872 and cloned into pXL3895, which had been digested with HindIII and AvrII, to form pXL3909.

9.2. Construction of pXL3948

In order to limit multimerization or dimerization of the plasmid during production of the plasmid in *E. coli.*, pXL3909 was digested by EcoRI, and a cer fragment, which had been isolated from pXL2786 by digestion with EcoRI, was inserted to result in plasmid pXL3948. The presence of the cer fragment permits recombination events that eliminate multimers formed during replication (ColE1 resolution) as described inter alia by Soubrier et al., (Gene Ther., 6: 1482–1488, 1999). The construction of pXL3948 is diagrammed in FIG. 12.

Minicircles that are obtained by using pXL3948 or pXL3909 (Example 9.1) have the same sequence.

Figure 13:
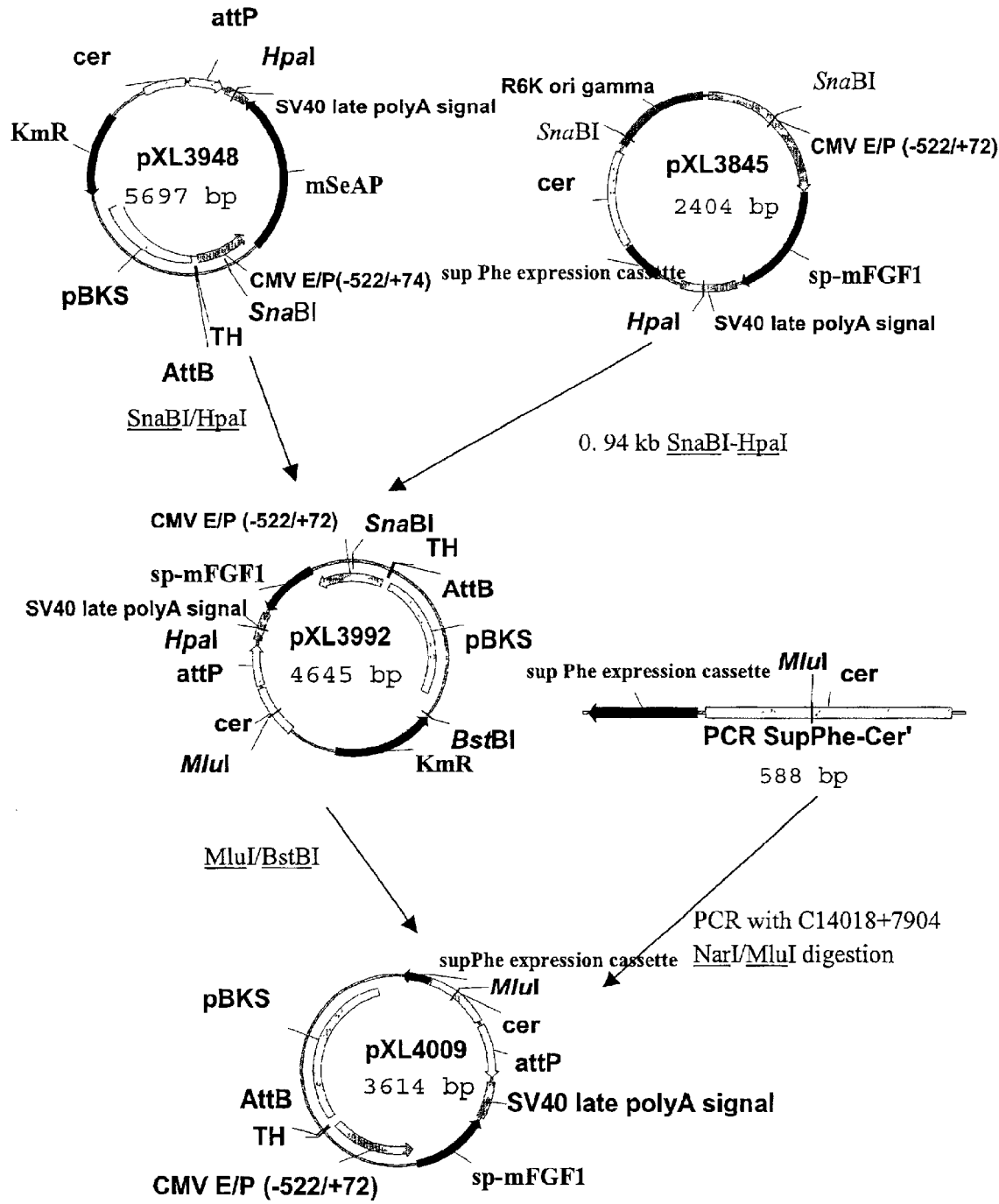
FIG. 13: Construction of pXL4009.

9.3 Construction of Plasmid pXL4009 (FIG. 13)

Plasmid pXL4009 is derived from the plasmid pXL3948 (Example 9.2) in which the kanamycin resistance gene (KmR) has been replaced by the selection marker supPhe (Soubrier et al., Gene Ther. 6: 1482–1488 (1999)). The preparation of pXL4009 from pXL3948 is diagrammed in FIG. 13. The minicircle obtained from pXL4009 has a murine FGF1 expression cassette. Minicircles that are obtained by using pXL3948, pXL3909, and pXL4009 have the same attL and TH sequence (Example 10, SEQ ID No. 12).

Example 10

Figure 14:
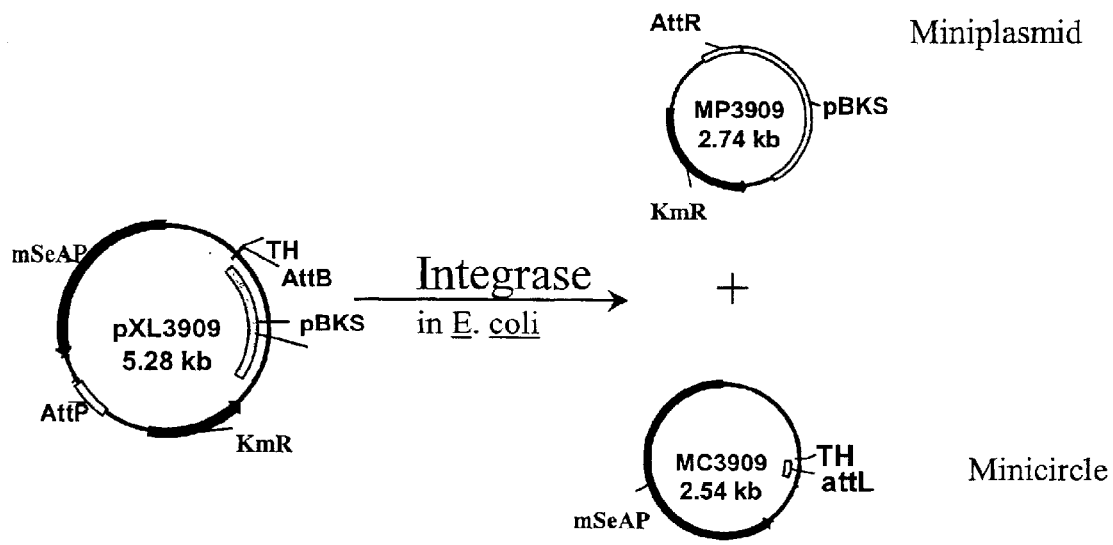
FIG. 14: λ Integrase-dependent recombination generates a miniplasmid and a minicircle.

Formation of a Minicircle Comprising an attL Site and a Triple Helix (TH) Forming Sequence Reaction of the bacteriophage λ integrase between sites attP and attB of pXL3909 allows formation of i) a 2.54 kb minicircle (MC3909) containing site attL, a TH forming sequence SEQ ID NO: 12, and a sequence encoding mSeAP; and ii) a 2.74 kb miniplasmid (MP3909) containing the replication origin of pBKS, a kanamycin resistance gene (KmR) and an attR site. This reaction is diagrammed in FIG. 14.

Example 11

Use of Strain in Which λ Integrase is Under the Control of the Plac Promoter 11.1 Construction of Phase pXL3870

Phage pXL3870 comprises a gene for kanamycin resistance and the gene encoding λ integrase under control of the placUV5 promoter. Located both 5' and 3' of the λ integrase expression cassette is a truncated copy of the uidA gene. The construction of pXL3870 is diagrammed in FIGS. 15 and 16. Briefly, the bacteriophage λ integrase sequence from strain D1210HP (Hasan et al., Gene 56: 145–151, 1987) was cloned by PCR using oligonucleotides C6597 and C6592, respectively, with the following sequences:

5'-ATCCTAGGTCATTATTTGATTTCAATTTTG-3' (SEQ ID No. 37)

5'-CAATCTAGATTTCTCGAGGCCCGGGCTCATTAGGCACCCC-3' (SEQ ID No. 38)

The resulting sequence was inserted between the lacUV5 promoter and the fd terminator (i.e., the transcription terminator from bacteriophage fd) of pXL3789 so that expression of λ integrase expression was controlled by the lacUV5 promoter. The region comprising the lacUV5 promoter, and the λ integrase gene, was excised from pXL3789 by digestion with XbaI and MluI, purified as above, and cloned into XbaI/MluI-digested pXL2981 (Appl. Microbiol. Biotechnol. 1998, 49: 560–567) to form pXL3791. In order to clone the fd terminator, the following oligonucleotides C7536 and C7537:

5'-CTAGGATAAACCGATACAATTAAAGGCTCCTTTTGGAGCCTTTTTTTTGGAGAACTAGTA-3' (SEQ ID No. 39)

5'-CGCGTACTAGTTCTCCAAAAAAAAAGGCTCCAAAAGGAGCCTTTAATTGTATCGGTTTATC-3' (SEQ ID No. 40)

were annealed and cloned into pXL3791 to form pXL3817. The integrase expression cassette flanked by uidA sequences from pXL3817 was then introduced into a M13mp9 phage within the uidA gene, to produce phage pXL3870.

Figure 15:
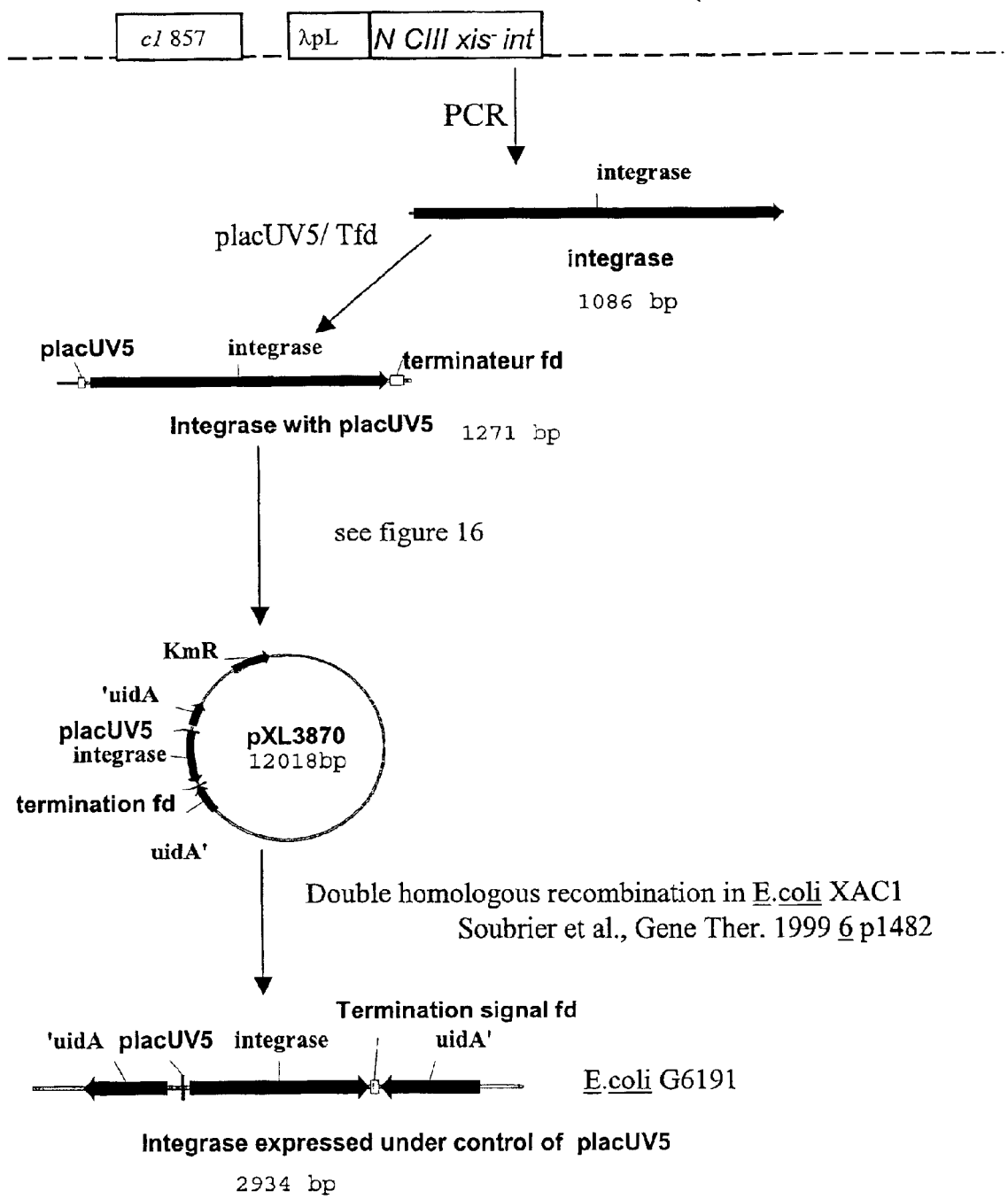
FIG. 15: Construction of *E. coli* strain G6191.
Figure 16:
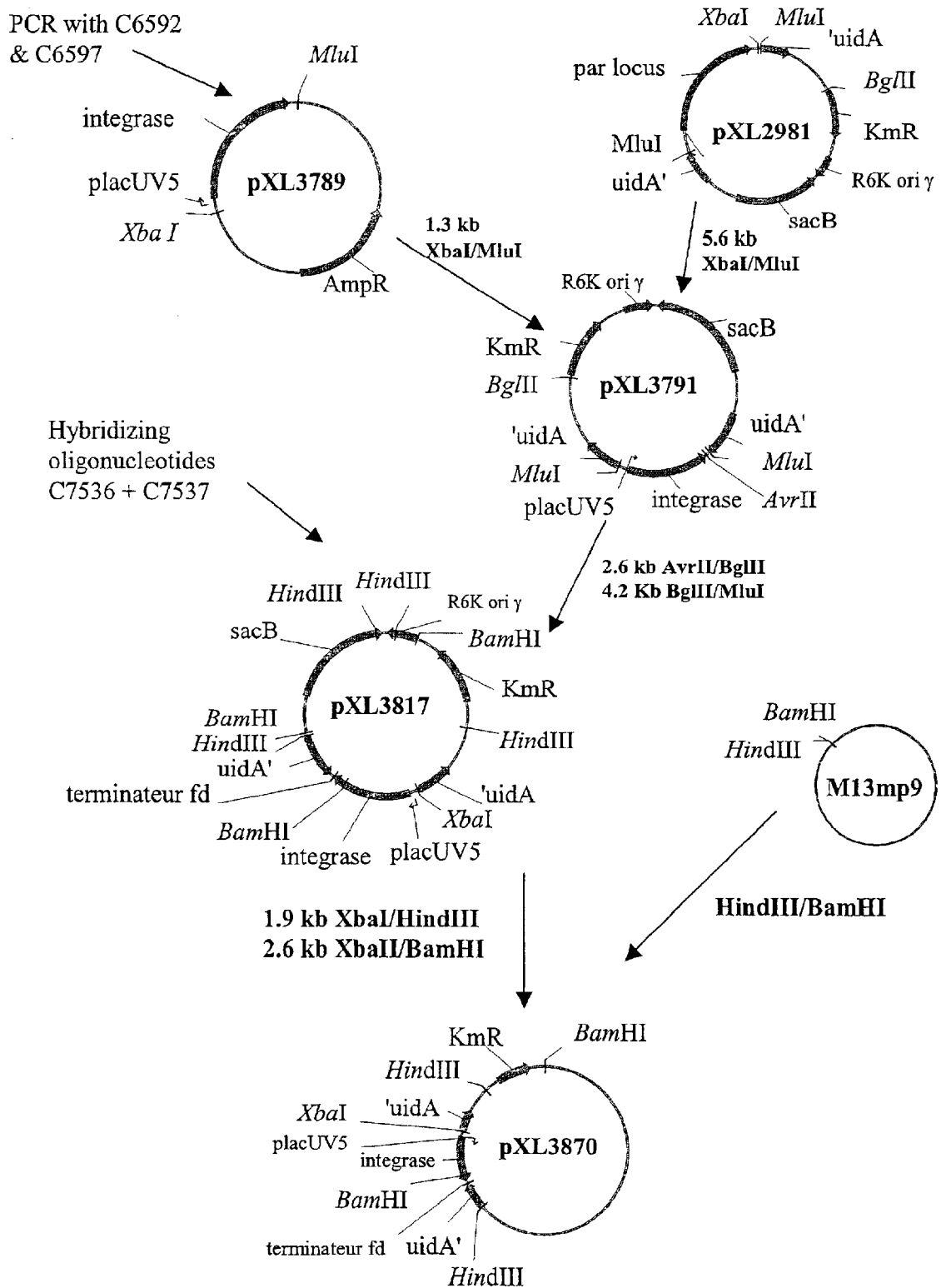
FIG. 16: Construction of the suicide phage pXL3870.

11.2 Construction of the Bacterial Strain G6191 Comprising λ Integrase Under the Control of placUV5 (FIG. 15)

Using suicide phage pXL3870, λ integrase was inserted in the genome of *E. coli* XAC-1, via homologous recombination at the 5' and 3' ends of the uidA gene, as described by Soubrier et al., Gene Ther. 6: 1482–1488, 1999. Correct insertion of λ integrase on the genome of G6191 was verified by PCR. The expression of the λ integrase gene in strain G6191 is regulated by the placUV5 promoter.

Figure 17:
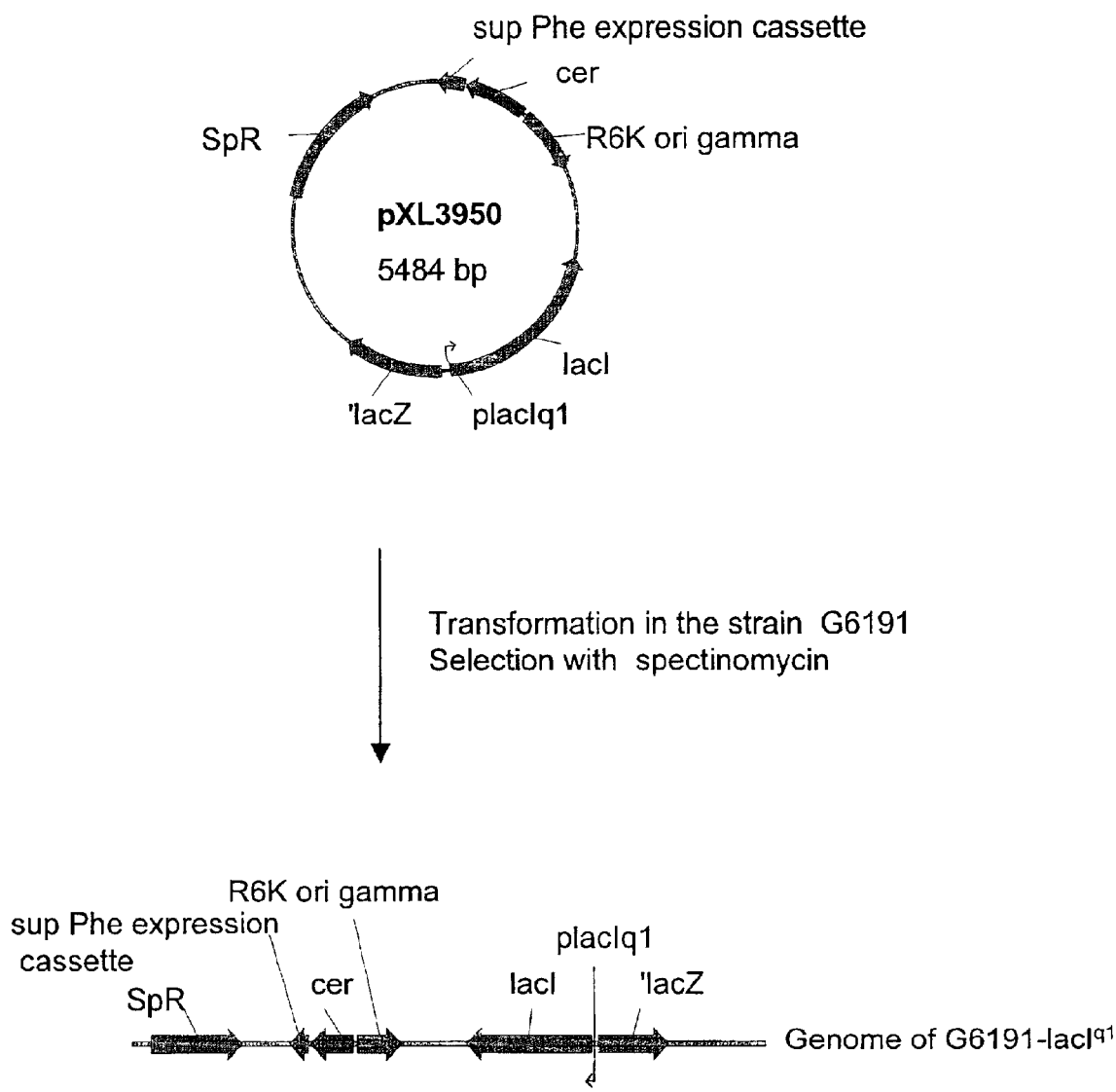
FIG. 17: Construction of *E. coli* strain G6191-lacI$^{q1}$.

11.3 Construction of Plasmid pXL3950 (FIG. 17)

The suicide plasmid pXL3950 containing a lacI gene, a placI$^{q1}$ promoter, adjacent regions thereof, a gene for spectinomycin resistance, and the conditional origin of replication R6Kγ (oriγ) is shown in FIG. 17. The promoter placI$^{q1}$ (Gene 228: 221–231, 1988) is known to drive high level expression of the repressor and is used to regulate the activity of the placUV5 promoter and, in this example, to reduce the expression of λ integrase under the control of placUV5 in the absence of the inducer, isopropylthio-β-D-galactoside (IPTG).

11.4 Construction of the Bacterial Strain G6191-lacI$^{q1}$ (FIG. 17)

The suicide plasmid pXL3950 containing a lacI gene under the control of a placI$^{q1}$ promoter was introduced into the bacterial strain G6191 by recombination as shown in FIG. 17. Recombinants were selected by their resistance to spectinomycin. The strain G6191-lacI$^{q1}$ so obtained was analyzed by PCR to verify the presence of oriγ in the genome.

Figure 18:
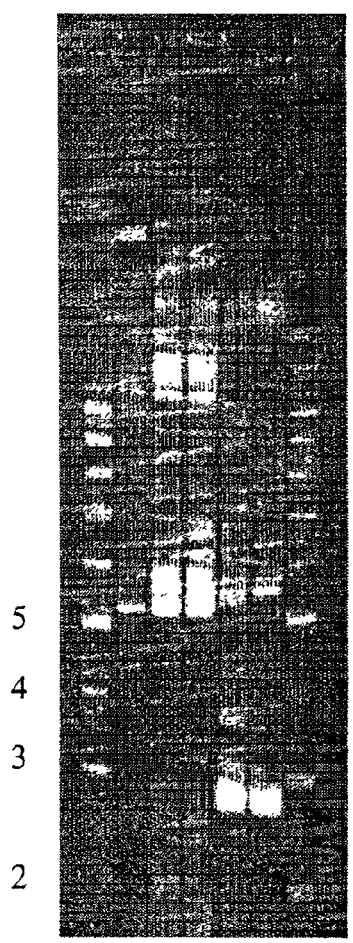
FIG. 18: Integrase activity in the strains G6191 and G6191-lacI$^{q1}$. Lanes 1 and 7: supercoiled plasmid ladder (kb); lane 2: plasmid pXL3909; lanes 3 and 4: DNA extracted from G6191-lacI$^{q1}$ containing pXL3909 in the absence of IPTG (2 clones); lanes 5 and 6: DNA extracted from G6191 containing pXL3909 in the absence of IPTG (2 clones).

11.5 Expression of the λ Integrase Gene in Strains G6191 and G6191-lacI$^{q1}$ (FIG. 18)

The expression of λ integrase in G6191 and G6191-lacI$^{q1}$ strains comprising plasmid pXL3909 was assessed in absence of IPTG. Strains G6191 with pXL3909 and G6191-lacI$^{q1}$ with pXL3909 were grown in the absence of IPTG for 16 hours. Plasmid DNA was then extracted from each culture and analyzed by agarose gel electrophoresis.

The results are shown in FIG. 18. Plasmid DNA extracted from strain G6191 containing pXL3909 was loaded in lanes 5–6 of the gel. These lanes show a major band of DNA at 2.74 kb, which corresponds to the size of the miniplasmid (MP3909) obtained by site-specific recombination of the plasmid pXL3909, and a less abundant species at 5.28 kb, which corresponds to intact pXL3909.

Plasmid DNA extracted from strain G6191-lacI$^{q1}$/pXL3909 was loaded in lanes 3–4 of FIG. 18. These lanes show a major band corresponding to the plasmid pXL3909 (5.28 kb) and a less abundant species corresponding to the miniplasmid MP3909 (2.74 kb).

The presence of the miniplasmid indicates that there is residual expression of λ integrase, when the λ integrase gene is placed under control of placUV5, thereby allowing integrase-dependent recombination to occur, even in the absence of the inducer and high level of LacI repressor. This clearly indicates that placUV5 does not permit sufficiently tight regulation of λ integrase expression.

Example 12

Figure 20:
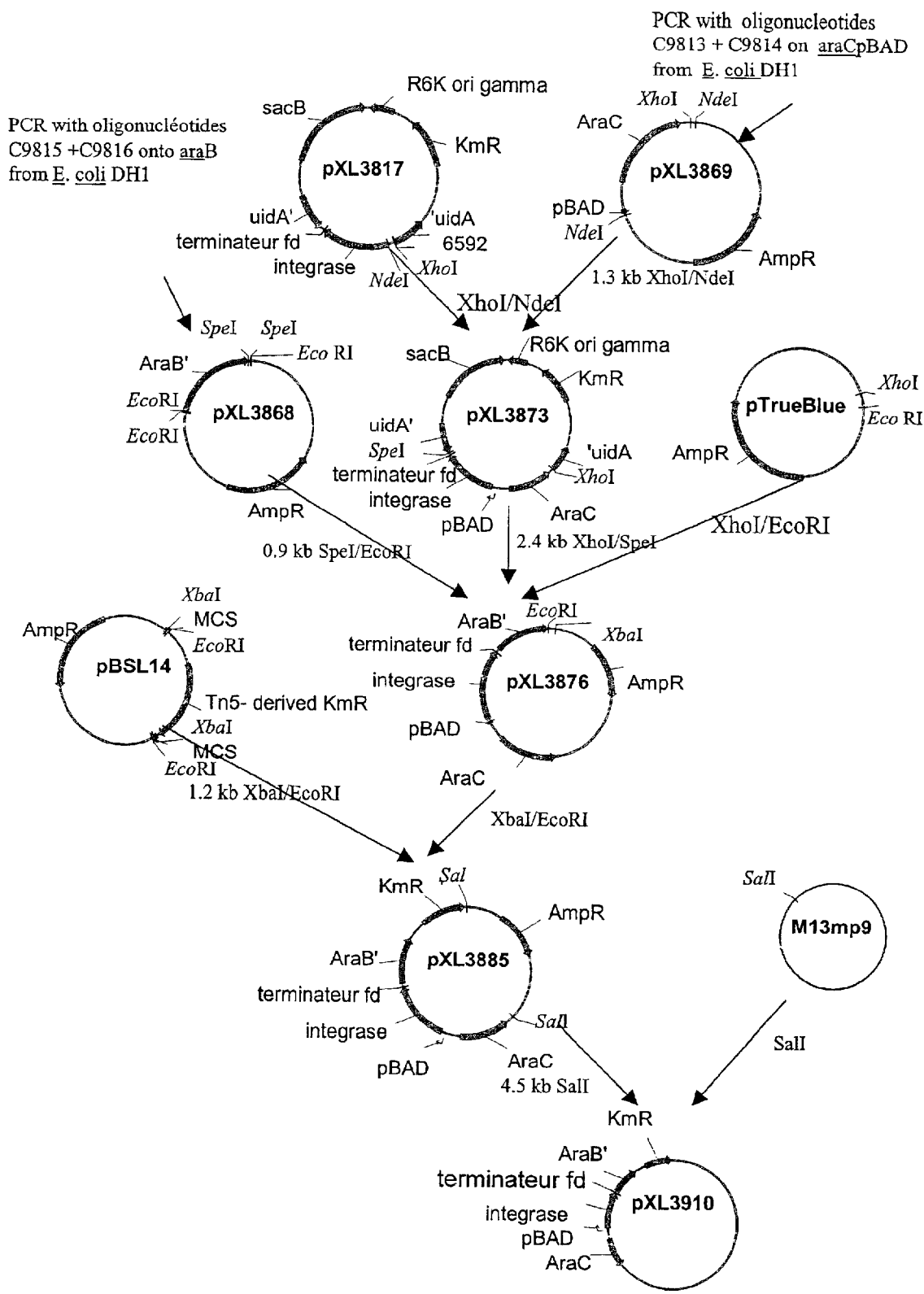
FIG. 20: Construction of the suicide phage pXL3910.

Use of a Strain wherein the λ Integrase is Under the Control of a pBAD Promoter 12.1 Construction of Phase pXL3910 (FIG. 20)

Phage pXL3910 comprises the λ integrase encoding sequence under the control of the promoter pBAD and termination signals from phage fd.

As described in Example 11.1, pXL3817 comprises a sequence encoding λ integrase cloned from *E. coli* strain D1210HP by PCR. That plasmid was linearized by digestion with XhoI and NdeI. A fragment comprising the pBAD promoter and the araC gene, which were cloned by PCR from *E coli* DH1 to form pXL3869 using the following oligonucleotides C9813 and C9814:

5'-AAACTCGAGCAATGCTTGCATAA-3'   (SEQ ID No. 41)

5'-AAACATATGTTCACTCCATCCAA-3'   (SEQ ID No. 42), was ligated to the linear pXL3817 DNA to produce pXL3873.

To produce pXL3868, the araB gene was cloned by PCR from *E. coli* DH1 using the following oligonucleotides C9815 and C9816:

5'-AAAACTAGTATGGCGATTGCAA-3'   (SEQ ID No. 43)

5'-AAAGAATTCGCAGTCAAACGCG-3'   (SEQ ID No. 44).

A 0.9 kb fragment isolated from pXL3868 by digestion with SpeI and EcoRI, which comprises the araB gene and a 2.4 kb fragment isolated from pXL3873 by digestion with XhoI and SpeI, which comprises the araC gene as well as the λ integrase gene under control of the pBAD promoter and the fd terminator, were ligated with pTrueBlue® (Genomics One Corp., Laval Canada), which had been linearized by digestion with XhoI and EcoRI. The resulting plasmid is pXL3876.

A 1.2 kb fragment comprising a gene for kanamycin resistance was isolated by digestion of pBSL14 (ATCC Accession No. 87127) with XbaI and EcoRI and ligated with XbaI/EcoRI digested pXL3876 to form pXL3885. A 4.5 kb SalI fragment from pXL3885, which comprises the araC and araB genes, the kanamycin resistance gene as well as the λ integrase gene under control of the pBAD promoter and the fd terminator was cloned into M13mp9, which had been linearized with SalI, to form pXL3910. This procedure is diagrammed in FIG. 20.

Figure 19:
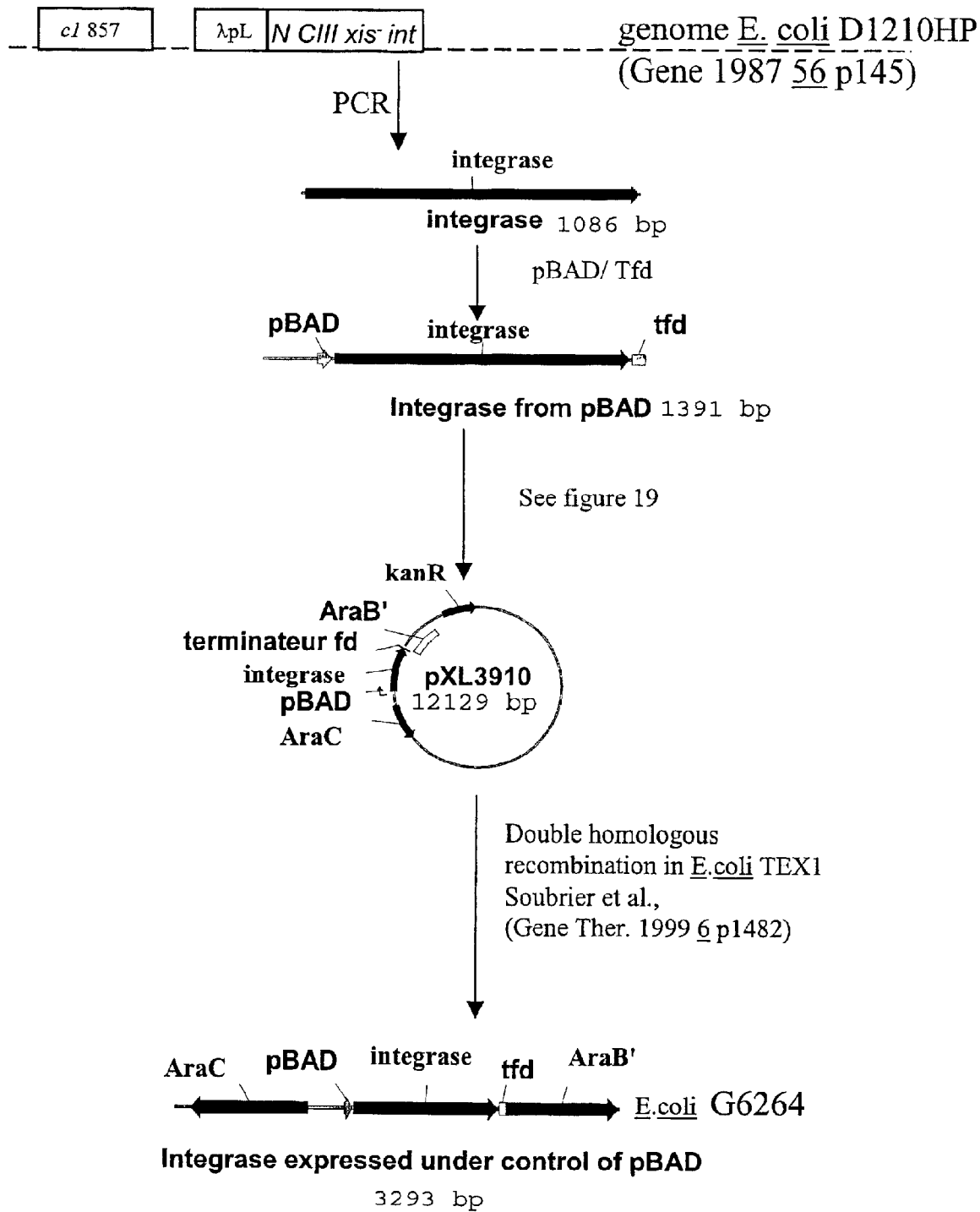
FIG. 19: Construction of *E. coli* strain G6264.

12.2 Construction of *E. coli* Strain G6264 Comprising a λ Integrase Gene Under the Control of the pBAD Promoter (FIG. 19)

Using the suicide plasmid pXL3910, the expression cassette was introduced in the genome of the *E. coli* strain TEX1 by double homologous recombination in 5' of the araC gene and 5' of the araB gene, as diagrammed in FIG. 19, according to Soubrier et al. (Gene Ther. 6: 1482–1488, 1999). The strain G6264 so obtained was analyzed by PCR to confirm the integration of the expression cassette. The strain G6264 was constructed to allow arabinose induction λ integrase expression through the promoter pBAD.

Figure 21:
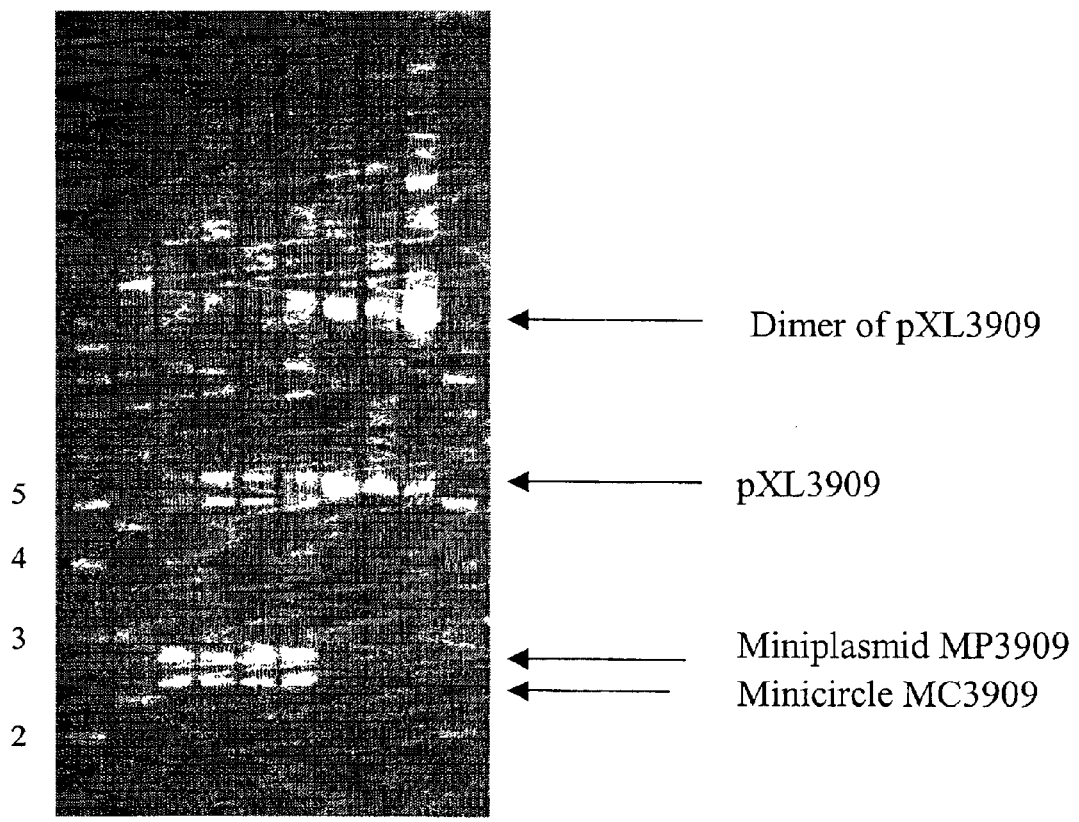
FIG. 21: Integrase activity of strain G6264 with or without induction. Lanes 1 and 10: supercoiled marker; lane 2: 1 kb linear ladder; lane 3: DNA extracted from strain G6264 containing pXL3909 after induction with 0.5% arabinose; lane 4: DNA extracted from strain G6264 containing pXL3909 after induction with 0.2% arabinose; lane 5: DNA extracted from strain G6264 containing pXL3909 after induction with 0.05% arabinose; lane 6: DNA extracted from strain G6264 containing pXL3909 after induction with 0.005% arabinose; lane 7: DNA extracted from strain G6264 containing pXL3909 with no induction; lane 8: DNA extracted from strain G6264 containing pXL3909 before induction with arabinose; lane 9: DNA extracted from strain G6264 containing pXL3909 grown overnight without induction.

12.3 Expression of λ Integrase by *E. coli* Strain G6264 Comprising pXL3909 (FIG. 21)

The expression of λ integrase in the strain G6264 comprising plasmid pXL3909 was assessed in the absence and in the presence of arabinose. The results are shown in FIG. 21. Strain G6264 with pXL3909 was cultured at 30° C. in the absence of arabinose for 16 hours (lane 9) and for 1 hour in presence of various concentrations of arabinose (lanes 3–6) or in the absence of arabinose (lanes 7–8). Plasmid DNA was then extracted from each culture and analyzed by electrophoresis through an agarose gel. In FIG. 20, the DNA band at 2.74 kb corresponds to the miniplasmid (MP3909), at 2.54 kb corresponds to the minicircle (MC3909), while the initial plasmid pXL3909 migrates as a 5.28 kb band.

The results shown in FIG. 21 clearly demonstrate that λ integrase-dependent recombination only occurs in the presence of the inducer arabinose, where 90% of the initial plasmid pXL3909 is recombined. While the concentration of arabinose (i.e., 0.005%; 0.05%; 0.2%; or 0.5%) does not appear in FIG. 21 to affect the efficiency of the λ integrase-dependent recombination, the optimum concentration of arabinose was 0.05%. The maximum induction of λ integrase expression in the presence of 0.05% arabinose was observed after 30 minutes.

Figure 25:
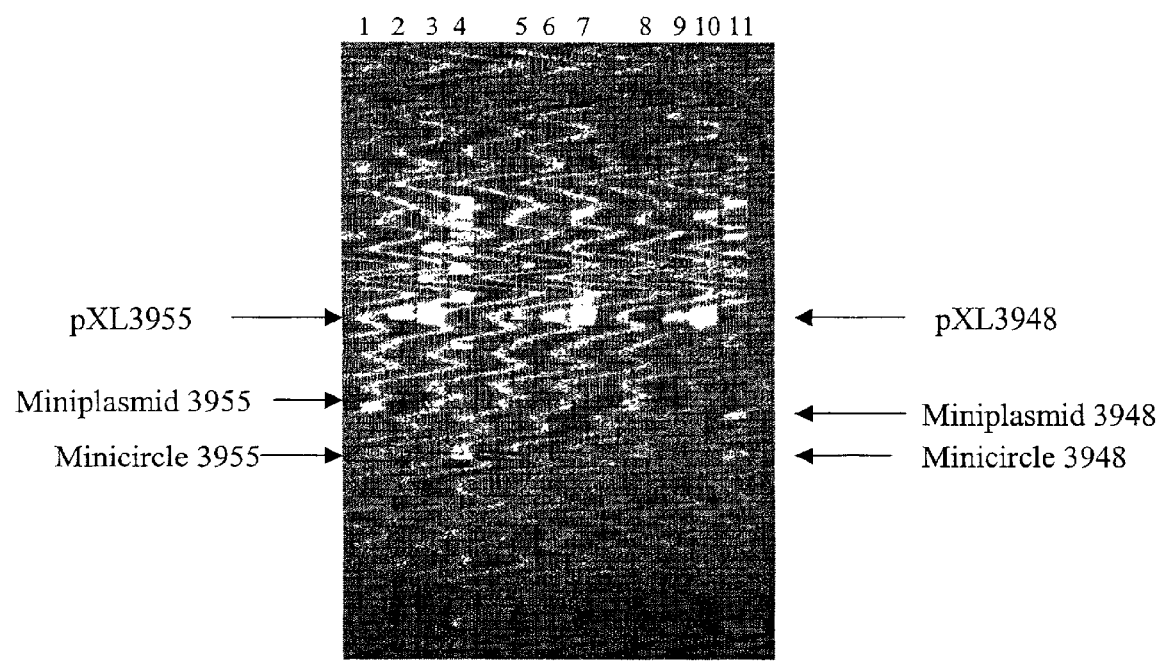
FIG. 25: Integrase activity in strains G6264 and 6289 with or without induction. Lane 1: DNA extracted from strain G6289 containing pXL3955 after induction with 0.05% arabinose; lanes 2 and 3: DNA extracted from strain G6289 containing pXL3955 and grown in the absence of arabinose; lane 5: DNA extracted from strain G6264 containing pXL3955 after induction with 0.05% arabinose; lanes 6 and 7: DNA extracted from strain G6264 containing pXL3955 and grown in the absence of arabinose; lane 8: DNA extracted from strain G6264 containing pXL3948 after induction with 0.05% arabinose; lanes 9 and 10: DNA extracted from strain G6264 containing pXL3948 and grown in the absence of arabinose; lane 11 & 4: 1 kb linear ladder.

12.4. Expression of the λ Integrase Gene in the Strain G6264 Comprising pXL3948 (FIG. 25)

The expression of λ integrase in the strain G6264 comprising plasmid pXL3948 (Example 10, FIG. 12) was assessed in the absence and presence of arabinose, as described in Example 13.3. The results are shown in FIG. 25. A comparison of lanes 9–10 (no arabinose) with lane 8

(0.05% arabinose) demonstrates that efficient site-specific recombination to produce the miniplasmid (MP3948) and minicircle (MC 3948) occurs only in the presence of the inducing agent arabinose (lane 8). The attL sequence in MC3909 and MC3948 was sequenced and found to be correct (FIG. 13, SEQ ID NO:12).

Similar results were obtained with strain G6264 containing pXL4009.

Example 13

Figure 22:
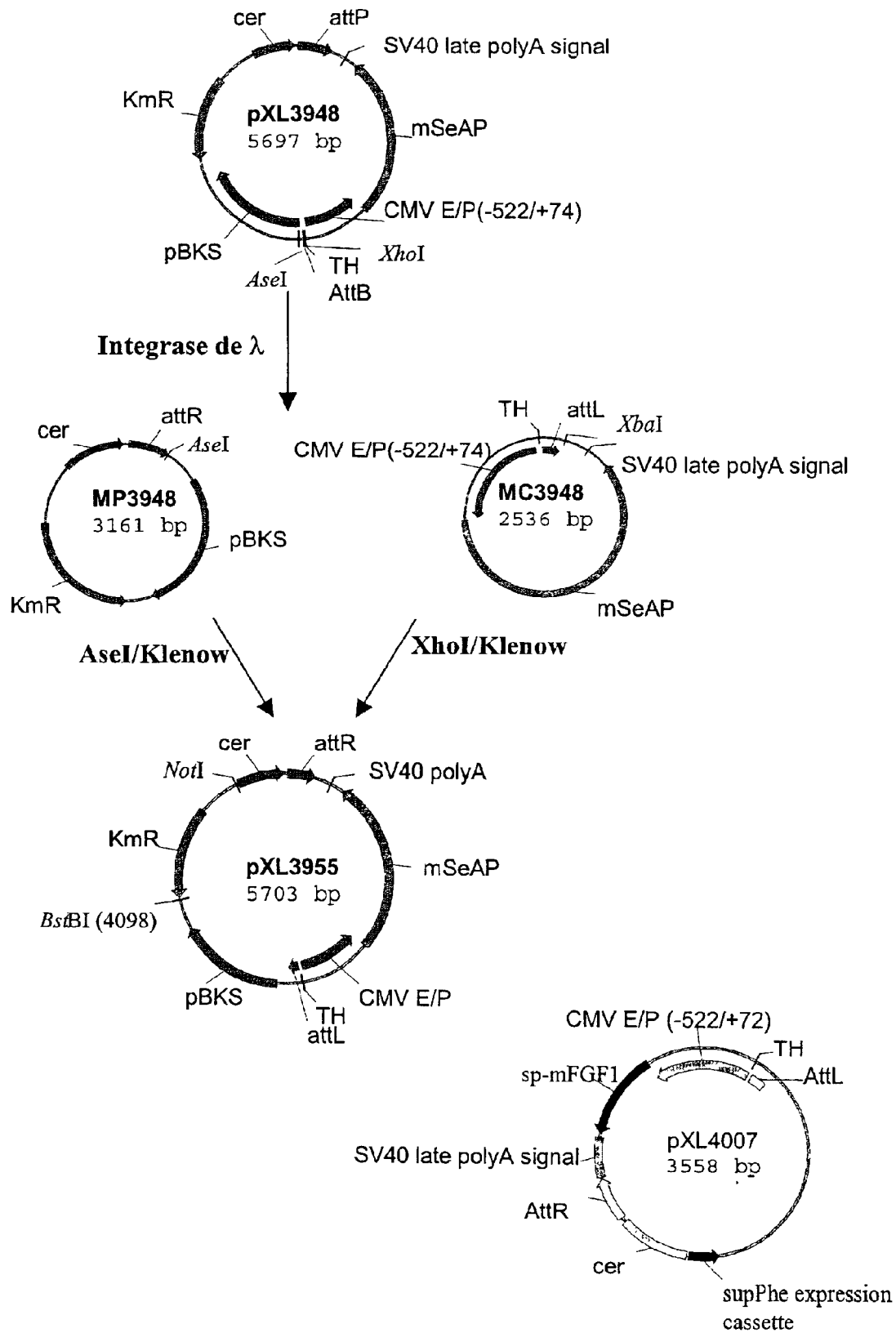
FIG. 22: Construction of pXL3955 and schematic representation of pXL4007.
Figure 23:
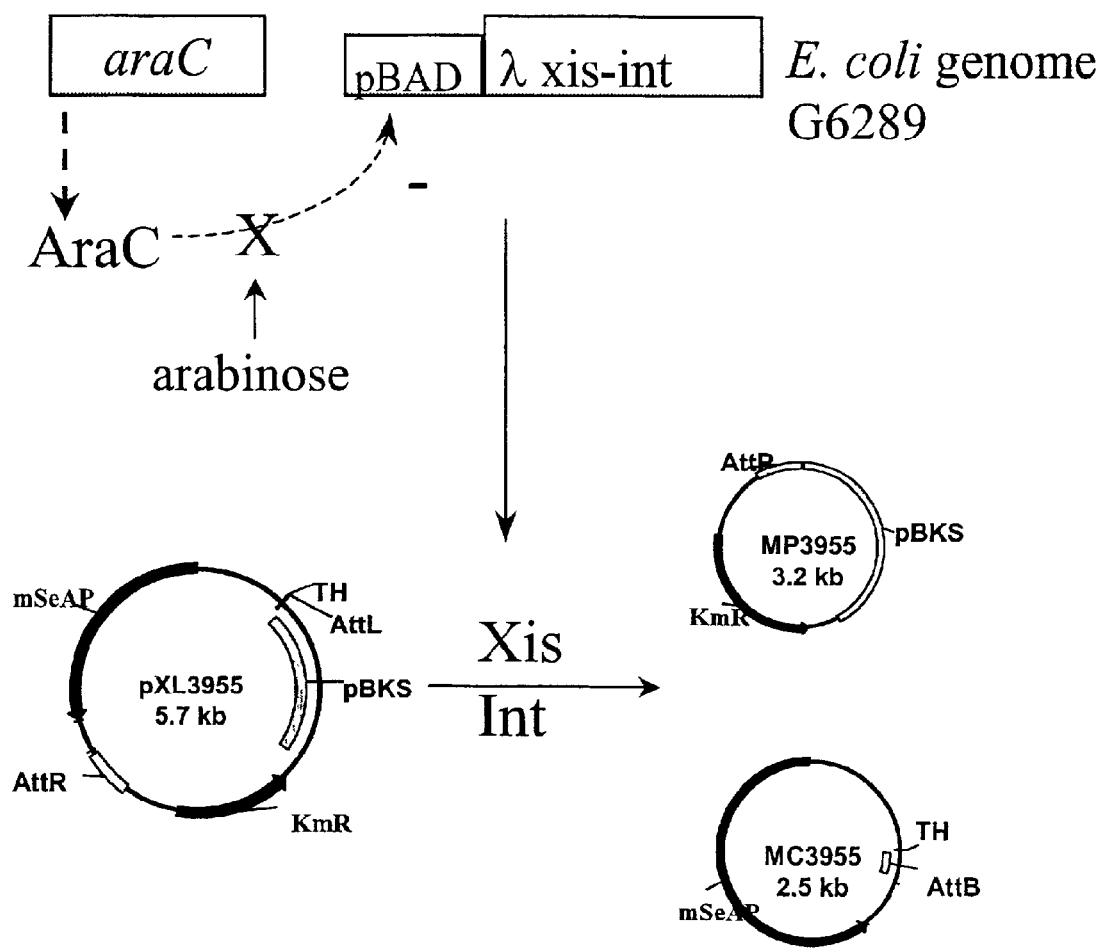
FIG. 23: λ Integrase and excisionase dependent recombination.

Preparation of a Minicircle Comprising a Eukaryotic Expression Cassette, a Bacteriophage λ attB Site, and a Triple Helix (TH) Forming Sequence (FIGS. 22–23)

13.1 Construction of Plasmid pXL3955 pXL3955 was derived from pXL3948 (see Example 9.2), but contains attR and attL sites in the direct orientation. A triple helix forming sequence (5'-AAGAAAAAAAAGAA-3', SEQ ID NO.32) and the expression cassette of the mSeAP (murine) were inserted between the attR and attL sites.

As diagrammed in FIG. 22, pXL3955 was prepared by first incubating pXL3948 in vivo with λ integrase to produce MP3948 and MC3948. The miniplasmid MP3948 was linearized by digestion with AseI and then the ends were filled-in using the Klenow enzyme. The minicircle MC3948 was similarly linearized and rendered blunt ended by digestion with XhoI and treatment with the Klenow enzyme. The linearized minicircle and miniplasmid were ligated together to form pXL3955. A clone with the correct orientation of the attL and attR sites was verified by DNA sequencing.

Recombination between the attR and attL sites of pXL3955 allows formation of i) a minicircle containing an attB site, a TH forming sequence, and a sequence encoding mSeAP (murine SeAP); and ii) a miniplasmid containing the replication origin of pBKS, a kanamycin resistance gene (KmR) and an attP site (FIG. 23).

13.2 Construction of Plasmid pXL4007 (FIG. 22)

Plasmid pXL4007 differs from pXL4009 (Example 9.2.3 by the substitution of the attB and attP sequences by the attL and attR sequences, see FIG. 22. It differs from plasmid pXL3955 by the selection marker(the kanamycin resistance gene (KmR) has been replaced by the selection marker supPhe) and the expression cassette (the sequence encoding mSeAp has been replaced by the murine FGF1 sequence). A minicircle MC4007 obtained from pXL4007 contains an attB site, a TH forming sequence, and a sequence encoding Murine FGF1.

13.3 Construction of pXL3954 (FIG. 24)

Phage pXL3954 comprises the λ integrase and excisionase genes under the control of the pBAD promoter and the fd terminator, as well as the araB and araC genes. The construction of pXL3954 is diagrammed in FIG. 24.

Bacteriophage λ integrase (int) and excisionase (xis) were cloned by PCR from λgt10 (Clontech) using the following oligonucleotides C12541 and C6597:

```
5'-AAAACATATGTACTTGACACTTCAGGA-3'    (SEQ ID No. 45)

(SEQ ID No. 46).
5'-ATCCTAGGTCATTATTTGATTTCAATTTTG-3'
```

The resulting plasmid is pXL3951. A 4.7 kb SalI fragment of pXL3951, comprising the araC and araB genes, the λ excisionase gene, the λ integrase gene, the fd terminator, the pBAD promter, and the kanamycin resistance gene, was isolated and ligated to SalI-digested M13mp9 to form pXL3954.

13.4 Construction of a E. coli Strain G6289 Allowing Expression of Bacteriophage λ Integrase and Excisionase Under the Control of Promoter pBAD (FIG. 24)

Using the suicide plasmid pXL3954, the expression cassette was inserted in the E. coli G6264 strain by double homologous recombination with the 5'-end of the araC gene and with the 5'-end of the araB gene as shown in FIG. 24 and as described by Soubrier et al. (Gene Ther. 6: 1482–1488, 1999). Integration by homologous recombination was verified by PCR and sequencing of xis and int genes.

13.5 Coexpression of the λ Excisionase and Integrase After Induction by Arabinose (FIG. 25)

Coexpression of λ integrase and excisionase in the strain G6289 comprising plasmid pXL3955 or expression of λ integrase in the strain G6264 comprising either pXL3955 or pXL3948 was assessed in the presence of arabinose.

Strains G6289 with pXL3955 and G6264 with pXL3955 or pXL3948 were grown in the absence of arabinose for 16 hours and then 0.05% arabinose was added for 1 hour at 30° C. Plasmid DNA was extracted from each culture and analyzed by agarose gel electrophoresis.

The results are shown in FIG. 25. The 3.2 kb DNA band corresponds to the miniplasmid, the 2.5 kb DNA band corresponds to the minicircle, while the non-recombined plasmids pXL3955 and pXL 3988 migrate as 5.7 kb bands.

The results in FIG. 25 clearly demonstrate that, while there was efficient recombination and minicircle formation in the strain G6289/pXL3955 in the presence of 0.05% arabinose (lane 1), such a recombination did not occur in strain G6264/pXL3955 (lane 5). Because G6289 differs from G6264 only by the presence of the λ xis gene, this indicates that presence of the xis and int genes is necessary for recombination at the attR and attL sites. The results shown in FIG. 25 further demonstrate that while recombination is tightly controlled, i.e., there was no production of minicircle DNA in the absence of arabinose (lanes 2–3), 80% of the plasmid was recombined in the presence of arabinose (lane 1).

Reaction of the bacteriophage λ integrase and excisionase between attL and attR of pXL3955 allows formation of i) a 2.5 kb minicircle (MC3955) containing attB and a triple helix (TH) forming sequence of SEQ ID NO: 13 (5'-TTCTTTTTTTTCTTGAAGCCTGCTTTTTTATACTAAC TTGAGC-3') and a sequence encoding mSeAP; and ii) a 3.2 kb miniplasmid (MP3955) containing the replication origin of pBKS, a kanamycin resistance gene (Km$^R$) and an attP site. This reaction is diagrammed in FIG. 23.

The minicircle MC3955 obtained was sequenced and the correct attB and triple helix forming sequences were found (FIG. 23).

Similar results were obtained with strain G6289 containing pXL4007.

Example 14

Purification of the Minicircle

Plasmid pXL3909 was introduced into the strain E. coli strain G6264 (Example 13) to generate recombinant strain B646, which was cultured as described in Example 13 to generate minicircle DNA.

After centrifugation of the culture broth, nucleic acids were extracted from 25 g of cell pellet (dry cell weight)

using the standard alkaline lysis procedure (Birnboim and Doly, Nucleic Acids Research, 7:1513). The nucleic acids were pre-purified by anion-exchange chromatography on a 26-ml column of Fractogel TMAE HiCap (M), which was eluted with a gradient of sodium chloride in 25 mM Tris-HCl (pH 8.0). The fraction containing plasmid species (eluted with 800 mM sodium chloride) was adjusted to pH 4.5 with sodium acetate and 2 M sodium chloride and loaded onto a 10-ml triplex affinity column containing the covalently-bound homopyrimidine oligonucleotide FRB14 (5'-TCTTTTTTTCCT-3'; SEQ ID No. 47).

The flow through, which contained the minicircle was collected and loaded onto a 10-ml affinity column containing the covalently-bound homopyrimidine oligonucleotide FRB10 (5'-TTCTTTTTTTTCTT-3'; SEQ ID No. 48). After washing the column with 100 mM sodium acetate, 1 M NaCl (pH 4.5), the minicircle (3.1 mg) was eluted with 12 ml of 100 mM Tris-HCl, 0.5 mM EDTA (pH 9.0) and quantified by UV spectroscopy (260 nm) and anion-exchange HPLC on a GenPak-Fax column. The miniplasmid was undetectable (<1%) by agarose gel electrophoresis in the purified preparation.

Triplex affinity gels were synthesized from Sephacryl S-1000 SF (Pharmacia) matrix and oligonucleotides FRB10 and FRB14 by using a two-step procedure involving matrix activation with sodium m-periodate (pH 4.7) followed by oligonucleotide coupling by reductive animation as described in the international application No: PCT/FR95/01468.

Example 15

Long-term Kinetic of Intramuscular Expression After Electrotransfer in Mouse Muscle Tibialis cranialis muscles (n=10) were injected with 1.5×$10^{11}$ (0.5 μg minicircle) copy number of either minicircle 3677, pCOR Luc+ (pXL3032) or pBluescript Luc+ (pXL 3001) as represented in FIG. 26.

Twenty seconds after DNA injection, muscles were covered with conductive gel and placed between two flat parallel stainless electrodes 0.5 cm apart. The muscles were then subjected to 8 electric pulses of 20 ms duration at a voltage to distance ratio of 200 V/cm and at a 1 Hertz frequency, using the electropulsator-PET. At different times after plasmid injection, muscles were harvested in 1 ml lysis buffer. The muscles were homogenized. Luciferase activity was determined in the Victor luminometer in 10 μL supernatant and expressed in CPS/total muscles. Results are given as geometric mean and error bar represents the confident interval at 95%. The logarithmic data were statistically analyzed by ANOVA one way test.

Figure 27:
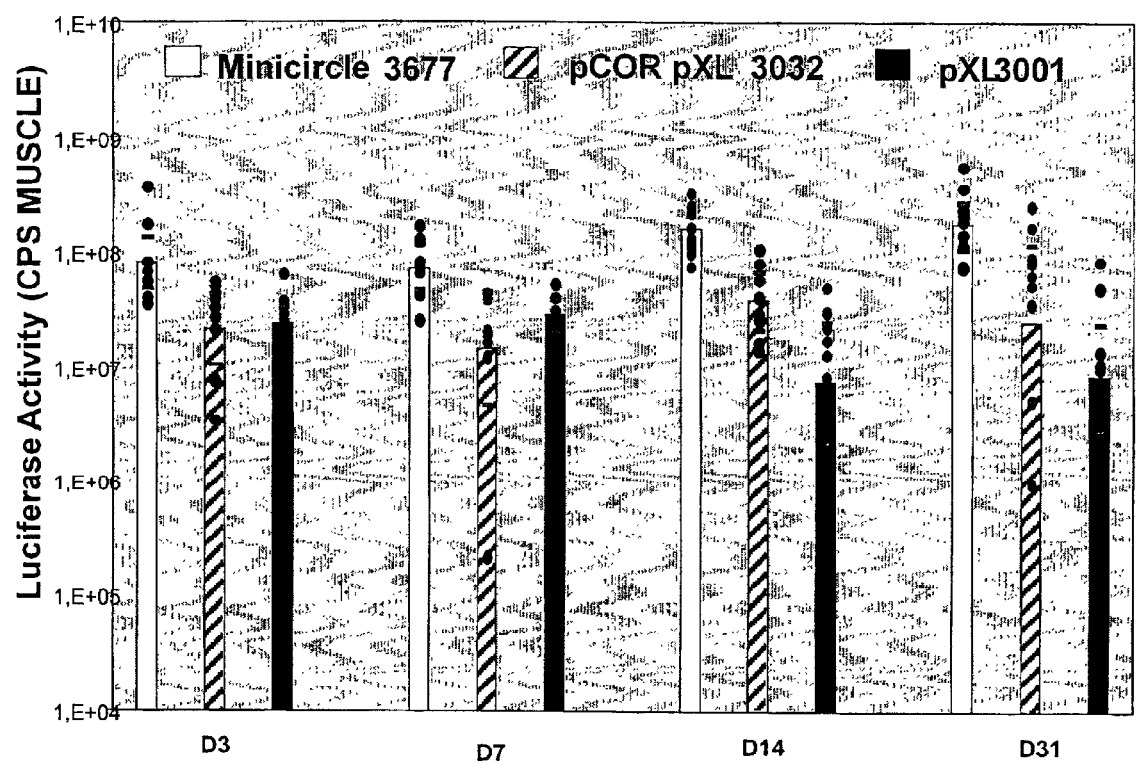
FIG. 27 illustrates the luciferase activity measured 3, 7, 14, and 31 days after electrotransfection of 1.5×10$^{11}$ copy number of minicircle 3677 (0.5 µg/30 µl minicircle), pCOR pXL3032, and pXL Amp 3001 plasmids.

After identical copy number (1.5×$10^{11}$ copy) injection of the 3 different plasmids, the intramuscular electrotransfection using minicircle was slightly increased with time in contrast to the pCOR or pBluescript plasmids, as demonstrated in FIG. 27.

The intramuscular transfection induced by minicircle was statistically higher in comparison with pBluescript plasmid pXL3001. This increase was a 3 to 21 fold increase from day 3 to day 31, as shown in Table 1 as follows.

TABLE 1

| Transfection ratio | D3 | D7 | D14 | D31 |
|---|---|---|---|---|
| Minicircle/pXL3001 (%) | 332 | 259 | 2056 | 2116 |
| Minicircle/pCOR pXL3032 (%) | 376 | 502 | 410 | 706 |
| pCOR pXL3032/pXL3001 (%) | 88 | 51 | 501 | 300 |

When the minicircle was compared to the pCOR plasmid, the better transfection potential of the minicircle was again clearly demonstrated (3 to 7 fold increase). This could be due to a better persistence of the smaller size vector in the muscle cells.

At identical copy number, the superiority of the transfection of the smallest size minicircle was demonstrated at short and long term in comparison with pCOR and the market competitor pBluescript (also known as ColE1 Amp) plasmids.

Example 16

Production of Minicircles by Fermentation Process

This example describes a method for producing the minicircle MC3948 using High Cellular Density Process (HCDC). The strain G6264 comprising plasmid pXL3948 was grown on defined medium with glucose as source of carbon.

Main fermentation conditions were:

pH was controlled at 6.9–7 with a 20% aqueous solution of $NH_3$ and a 30% solution of orthophosphoric acid;

minimal partial oxygen tension ($pO_2$) was set at 30% of saturation with air;

fermentation was operated at 30° C.; and aeration rate was set at 1.5 vvm.

The HCDC started as a batch process that was inoculated in a 10% volumetric ratio with thawed stocks grown overnight on defined medium (5 g/L glucose). After total consumption of the initial glucose (2 g/L), as indicated by a fast increase of dissolved oxygen concentration, 50% (w/v) glucose solution supplemented with $MgSO_4\text{-}7H_2O$ (0.7%) and thiamine (0.02%) was fed into the reactor. Feeding was carried out in order to increase cell-mass exponentially and to grow cells in glucose-limited conditions.

The optimal growth rate ($\mu$set) was determined in order to recombine plasmid pXL3948 with maximal efficiency, and to prevent any accumulation of toxic levels of acetic acid ($\mu_{set} < \mu_{crit}$) When cell density reached values up to 30 g/L DCW, the culture was induced with an injection of arabinose (0.4% (w/vol. of culture) over a period of 30 to 90 minutes. Then, glucose feeding was stopped and cells were washed and were recovered by centrifugation. Cells were finally stored at −80° C.

Analysis of extracted pDNA by electrophoresis showed that good recombination efficiency results were obtained (more than 90%). This result was obtained despite the fact that glucose was used as the source of carbon throughout the fermentation (i.e., no effect of catabolic repression was observed on recombination efficiency under glucose limited conditions).

Other embodiments of the invention will be apparent to those skilled in the art from consideration of the specification and practice of the invention disclosed herein. It is intended that the specification and examples be considered as exemplary only, with the true scope and spirit of the invention being indicated by the claims.

We claim:

1. A double-stranded DNA molecule, comprising an expression cassette containing a gene of interest under control of a transcription promoter and a transcription terminator active in a mammalian cell, wherein said molecule:
   is in circular and supercoiled form,
   lacks an origin of replication,
   lacks a selection marker gene, and
   comprises a sequence attB resulting from site-specific recombination between an attL and an attR sequence or between and an attL derived sequence and an attR derived sequence, said sequence attB being located outside the expression cassette.

2. The molecule according to claim 1, further comprising a sequence that interacts specifically with an oligonucleotide to form a triple helix by hybridization.

3. The molecule according to claim 2, wherein the sequence that forms a triple helix comprises from 5 to 30 base pairs.

4. The molecule according to claim 2, wherein said molecule is MC3955 or MC4007.

5. The molecule according to claim 2, wherein the sequence that forms a triple helix and the sequence attB are contiguous and are set forth in SEQ ID NO: 13.

6. The molecule according to claim 1, further comprising an mrs sequence originating from a par locus of RK2.

7. The molecule according to claim 1, wherein the gene of interest is a nucleic acid coding for a therapeutic, vaccine, agricultural, or veterinary product.

8. The molecule according to claim 1, wherein said molecule is obtained by excision from a plasmid or chromosome by site-specific recombination.

9. A plasmid which is pXL3909, pXL3948 or pXL4009.

10. A plasmid comprising an expression cassette positioned between attL and attR sequences of a bacteriophage lambda, wherein said expression cassette lacks a gene for a selectable marker and comprises a gene of interest under control of a transcription promoter and a transcription terminator active in a mammalian cell.

11. The plasmid according to claim 10, further comprising an origin of replication and a selection marker gene, wherein the origin of replication and selection marker gene are located outside said expression cassette.

12. The plasmid according to claim 11, wherein said plasmid is pXL3955 or pXL4007.

13. The plasmid according to claim 11, wherein the selection marker gene is a gene for kanamycin resistance or the tRNA suppressor supPhe.

14. The plasmid according to claim 10, further comprising a sequence that interacts specifically with an oligonucleotide to form a triple helix by hybridization.

15. A plasmid comprising:
   (a) a bacterial origin of replication and a selection marker gene; and
   (b) a polynucleotide comprising an expression cassette positioned between attL and attR sequences of a bacteriophage lambda, p22, φ80, P1 or HP1, or of a plasmid pSAM2 or between an attL derived sequence and an attR derived sequence, positioned in direct orientation, which recombine by site-specific recombination in the presence of an integrase and an excisionase, wherein said expression cassette comprises a gene of interest under control of a transcription promoter and a transcription terminator active in a mammalian cell, and wherein said polynucleotide lacks an origin of replication and a selection marker gene.

16. A cultured recombinant cell comprising within its genome a gene coding for an integrase under the control of a plac UV5 promoter, wherein said cell is *Escherichia coli* strain G6191.

17. A cultured recombinant cell comprising within its genome a gene coding for an integrase under the control of a pBAD promoter, wherein said cell *Escherichia coli* strain G6264.

18. A cultured recombinant cell comprising within its genome an integrase gene and an excisionase gene under the control of a pBAD promoter, wherein said cell is *Escherichia coli* strain G6289.

19. A method for preparation of the DNA molecule according to claim 1, comprising culturing 1) a host cell comprising a recombinant DNA comprising a nucleic acid consisting of an expression cassette positioned between an attR and an attL sequence or between an attR derived sequence and an attL derived sequence positioned in direct orientation, which recombine by site-specific recombination in the presence of an integrase and an excisionase to form an attB sequence, and wherein the expression cassette comprises a gene of interest under control of a transcription promoter and a transcription terminator active in a mammalian cell with 2) an integrase and an excisionase, whereby site-specific recombination occurs between the two sequences positioned in direct orientation.

20. The method according to claim 19, wherein the cultured host cell is brought into contact with the integrase and the excisionase by transforming or infecting the cultured host cell with a plasmid or a phage containing a gene for at least one of the recombinase or the excisionase.

21. The method according to claim 20, wherein the cultured host cell is brought into contact with the integrase and the excisionase by inducing expression of a gene coding for the integrase and a gene coding for the excisionase, wherein both genes are present in the host cell.

22. The method according to claim 21, wherein the host cell comprises within its genome an integrase gene and an excisionase gene, wherein expression of said genes is regulated by a chemically-inducible promoter, and further wherein the cultured host cell is brought into contact with the integrase and the excisionase by culturing the host cell in the presence of a chemical inducer of the promoter, whereby expression of the recombinase gene and of the excisionase gene is induced.

23. The method according to claim 22, wherein the chemically-inducible promoter is pBAD.

24. The method according to claim 23, wherein the host cell is *Escherichia coli* strain G6289.

25. The method according to claim 22, wherein the host cell comprises a lysogenic phage integrated in its genome and wherein the lysogenic phage comprises at least one of the gene for the integrase and the gene for the excisionase.

26. The method according to claim 19, further comprising purifying a minicircle formed by the site-specific recombination.

27. The method according to claim 26, wherein the minicircle is purified by first contacting the minicircle with a first specific oligonucleotide that is grafted onto a first support, whereby a triple helix is formed by hybridization of said first specific oligonucleotide with a first specific sequence present in the recombinant DNA, but not in the minicircle and by second contacting the minicircle with a second specific oligonucleotide that is grafted onto a second support, whereby a triple helix is formed by hybridization of said second specific oligonucleotide with a second specific sequence present in the minicircle.

28. The method according to claim 26, wherein the minicircle is purified by first contacting the minicircle with a first specific oligonucleotide that is grafted onto a first support, whereby a triple helix is formed by hybridization of said first specific oligonucleotide with a first specific sequence present in the minicircle, eluting the minicircle, and by second contacting the eluted minicircle with a second specific oligonucleotide that is grafted onto a second support, whereby a triple helix is formed by hybridization of said second specific oligonucleotide with a second specific sequence present in the recombinant DNA, but not in the minicircle.

29. A double-stranded DNA molecule, comprising an expression cassette containing a gene of interest under control of a transcription promoter and a transcription terminator active in a mammalian cell, wherein said molecule:

is in circular and supercoiled form, lacks an origin of replication, lacks a marker gene, and comprises a sequence attL resulting from site-specific recombination between an attB sequence and an attP sequence or between an attB derived sequence and an attP derived sequence, said sequence attL being located outside the expression cassette;

wherein said molecule further comprises a sequence that interacts specifically with an oligonucleotide to form a triple helix by hybridization; and wherein the sequence that forms a triple helix and the sequence attL are contiguous and are as set forth in SEQ ID NO: 12.

30. The molecule according to claim 29, wherein said molecule is MC3909, MC3948, or MC4009.

* * * * *

UNITED STATES PATENT AND TRADEMARK OFFICE
CERTIFICATE OF CORRECTION

PATENT NO. : 6,825,012 B2
APPLICATION NO. : 09/981803
DATED : November 30, 2004
INVENTOR(S) : Blanche et al.

It is certified that error appears in the above-identified patent and that said Letters Patent is hereby corrected as shown below:

In claim 1, column 55, line 41, "between and an" should read --between an--.

In claim 4, column 55, line 50, "claim 2," should read --claim 5,--.

In claim 17, column 56, line 66, "cell *Escherichia*" should read --cell is *Escherichia*--.

Signed and Sealed this

Eleventh Day of July, 2006

JON W. DUDAS
*Director of the United States Patent and Trademark Office*

SEQUENCE LISTING

<160> NUMBER OF SEQ ID NOS: 50

<210> SEQ ID NO 1
<211> LENGTH: 37
<212> TYPE: DNA
<213> ORGANISM: Artificial Sequence
<220> FEATURE:
<223> OTHER INFORMATION: Description of the artificial sequence:
      oligonucleotide

<400> SEQUENCE: 1
aattgtgaag cctgctttttt tatactaact tgagcgg                              37

<210> SEQ ID NO 2
<211> LENGTH: 37
<212> TYPE: DNA
<213> ORGANISM: Artificial sequence
<220> FEATURE:
<223> OTHER INFORMATION: Description of the artificial sequence:
      oligonucleotide

<400> SEQUENCE: 2
aattccgctc aagttagtat aaaaaagcag gcttcac                              37

<210> SEQ ID NO 3
<211> LENGTH: 21
<212> TYPE: DNA
<213> ORGANISM: Artificial sequence
<220> FEATURE:
<223> OTHER INFORMATION: Description of the artificial sequence:
      oligonucleotide

<400> SEQUENCE: 3
ctgctttttt atactaactt g                                               21

<210> SEQ ID NO 4
<211> LENGTH: 21
<212> TYPE: DNA
<213> ORGANISM: Artificial sequence
<220> FEATURE:
<223> OTHER INFORMATION: Description of the artificial sequence:
      oligonucleotide

<400> SEQUENCE: 4
cagctttttt atactaagtt g                                               21

<210> SEQ ID NO 5
<211> LENGTH: 21
<212> TYPE: DNA
<213> ORGANISM: Artificial sequence
<220> FEATURE:
<223> OTHER INFORMATION: Description of the artificial sequence:
      oligonucleotide

<400> SEQUENCE: 5
cagcgcattc gtaatgcgaa g                                               21

<210> SEQ ID NO 6
<211> LENGTH: 21
<212> TYPE: DNA
<213> ORGANISM: Artificial sequence
<220> FEATURE:
<223> OTHER INFORMATION: Description of the artificial sequence:
      oligonucleotide

<400> SEQUENCE: 6

```
cttataattc gtaatgcgaa g                                              21

<210> SEQ ID NO 7
<211> LENGTH: 19
<212> TYPE: DNA
<213> ORGANISM: Artificial sequence
<220> FEATURE:
<223> OTHER INFORMATION: Description of the artificial sequence:
      oligonucleotide

<400> SEQUENCE: 7
aacactttct taaatggtt                                                 19

<210> SEQ ID NO 8
<211> LENGTH: 19
<212> TYPE: DNA
<213> ORGANISM: Artificial sequence
<220> FEATURE:
<223> OTHER INFORMATION: Description of the artificial sequence:
      oligonucleotide

<400> SEQUENCE: 8
aacactttct taaattgtc                                                 19

<210> SEQ ID NO 9
<211> LENGTH: 19
<212> TYPE: DNA
<213> ORGANISM: Artificial sequence
<220> FEATURE:
<223> OTHER INFORMATION: Description of the artificial sequence:
      oligonucleotide

<400> SEQUENCE: 9
aagggattta aaatccctc                                                 19

<210> SEQ ID NO 10
<211> LENGTH: 19
<212> TYPE: DNA
<213> ORGANISM: Artificial sequence
<220> FEATURE:
<223> OTHER INFORMATION: Description of the artificial sequence:
      oligonucleotide

<400> SEQUENCE: 10
atggtattta aaatccctc                                                 19

<210> SEQ ID NO 11
<211> LENGTH: 49
<212> TYPE: DNA
<213> ORGANISM: Artificial sequence
<220> FEATURE:
<223> OTHER INFORMATION: Description of the artificial sequence:
      oligonucleotide

<400> SEQUENCE: 11
ttctctgtcg gggtggcggg atttgaaccc acgacctctt cgtcccgaa                49

<210> SEQ ID NO 12
<211> LENGTH: 119
<212> TYPE: DNA
<213> ORGANISM: Artificial sequence
<220> FEATURE:
<223> OTHER INFORMATION: Description of the artificial sequence:
      oligonucleotide

<400> SEQUENCE: 12
```

-continued ttcttttttt tcttgaagcc tgcttttta tactaagttg gcattataaa aaagcattgc    60
ttatcaattt gttgcaacga acaggtcact atcagtcaaa ataaaatcat tatttgatt   119

<210> SEQ ID NO 13
<211> LENGTH: 43
<212> TYPE: DNA
<213> ORGANISM: Artificial sequence
<220> FEATURE:
<223> OTHER INFORMATION: Description of the artificial sequence:
      oligonucleotide

<400> SEQUENCE: 13
ttcttttttt tcttgaagcc tgcttttta tactaacttg agc                       43

<210> SEQ ID NO 14
<211> LENGTH: 27
<212> TYPE: DNA
<213> ORGANISM: Artificial sequence
<220> FEATURE:
<223> OTHER INFORMATION: Description of the artificial sequence:
      oligonucleotide

<400> SEQUENCE: 14
cgtcgaaata ttataaatta tcagaca                                        27

<210> SEQ ID NO 15
<211> LENGTH: 25
<212> TYPE: DNA
<213> ORGANISM: Artificial sequence
<220> FEATURE:
<223> OTHER INFORMATION: Description of the artificial sequence:
      oligonucleotide

<400> SEQUENCE: 15
gaggcttctt cttcttcttc ttctt                                          25

<210> SEQ ID NO 16
<211> LENGTH: 20
<212> TYPE: DNA
<213> ORGANISM: Artificial sequence
<220> FEATURE:
<223> OTHER INFORMATION: Description of the artificial sequence:
      oligonucleotide

<400> SEQUENCE: 16
ttcttcttgc ttctcttctt                                                20

<210> SEQ ID NO 17
<211> LENGTH: 20
<212> TYPE: DNA
<213> ORGANISM: Artificial sequence
<220> FEATURE:
<223> OTHER INFORMATION: Description of the artificial sequence:
      oligonucleotide

<400> SEQUENCE: 17
ttcttcttgt ttctcttctt                                                20

<210> SEQ ID NO 18
<211> LENGTH: 20
<212> TYPE: DNA
<213> ORGANISM: Artificial sequence
<220> FEATURE:
<223> OTHER INFORMATION: Description of the artificial sequence:
      oligonucleotide

<400> SEQUENCE: 18
ttcttcttcc ttctcttctt                                              20

<210> SEQ ID NO 19
<211> LENGTH: 20
<212> TYPE: DNA
<213> ORGANISM: Artificial sequence
<220> FEATURE:
<223> OTHER INFORMATION: Description of the artificial sequence:
      oligonucleotide

<400> SEQUENCE: 19
aagaagcatg cagagaagaa                                              20

<210> SEQ ID NO 20
<211> LENGTH: 57
<212> TYPE: DNA
<213> ORGANISM: Artificial sequence
<220> FEATURE:
<223> OTHER INFORMATION: Description of the artificial sequence:
      oligonucleotide

<400> SEQUENCE: 20
gatccgaaga agaagaagaa gaagaagaag aagaagaaga agaagaagaa gaagaac     57

<210> SEQ ID NO 21
<211> LENGTH: 57
<212> TYPE: DNA
<213> ORGANISM: Artificial sequence
<220> FEATURE:
<223> OTHER INFORMATION: Description of the artificial sequence:
      oligonucleotide

<400> SEQUENCE: 21
gatcgttctt cttcttcttc ttcttcttct tcttcttctt cttcttcttc ttcttcg     57

<210> SEQ ID NO 22
<211> LENGTH: 66
<212> TYPE: DNA
<213> ORGANISM: Artificial sequence
<220> FEATURE:
<223> OTHER INFORMATION: Description of the artificial sequence:
      oligonucleotide

<400> SEQUENCE: 22
gatctgaaga agaagaagaa gaagaagaag aagaagaaga agaagaagaa gaagaactgc  60
agatct                                                             66

<210> SEQ ID NO 23
<211> LENGTH: 66
<212> TYPE: DNA
<213> ORGANISM: Artificial sequence
<220> FEATURE:
<223> OTHER INFORMATION: Description of the artificial sequence:
      oligonucleotide

<400> SEQUENCE: 23
gatcagatct gcagttcttc ttcttcttct tcttcttctt cttcttcttc ttcttcttct  60
tcttca                                                             66

<210> SEQ ID NO 24
<211> LENGTH: 56
<212> TYPE: DNA
<213> ORGANISM: Artificial sequence
<220> FEATURE:
<223> OTHER INFORMATION: Description of the artificial sequence:

oligonucleotide

<400> SEQUENCE: 24
gatcagatct gcagtctctt cttcttcttc ttcttcttct tcttcttctc ttctca    56

<210> SEQ ID NO 25
<211> LENGTH: 21
<212> TYPE: DNA
<213> ORGANISM: Artificial sequence
<220> FEATURE:
<223> OTHER INFORMATION: Description of the artificial sequence:
      oligonucleotide

<400> SEQUENCE: 25
cttcttcttc ttcttcttct t    21

<210> SEQ ID NO 26
<211> LENGTH: 56
<212> TYPE: DNA
<213> ORGANISM: Artificial sequence
<220> FEATURE:
<223> OTHER INFORMATION: Description of the artificial sequence:
      oligonucleotide

<400> SEQUENCE: 26
agcttctcga gctgcaggat atcgaattcg gatcctctag agcggccgcg agctcc    56

<210> SEQ ID NO 27
<211> LENGTH: 56
<212> TYPE: DNA
<213> ORGANISM: Artificial sequence
<220> FEATURE:
<223> OTHER INFORMATION: Description of the artificial sequence:
      oligonucleotide

<400> SEQUENCE: 27
agctggagct cgcggccgct ctagaggatc cgaattcgat atcctgcagc tcgaga    56

<210> SEQ ID NO 28
<211> LENGTH: 49
<212> TYPE: DNA
<213> ORGANISM: Artificial sequence
<220> FEATURE:
<223> OTHER INFORMATION: Description of the artificial sequence:
      oligonucleotide

<400> SEQUENCE: 28
actagtggcc atgcatccgc tcaagttagt ataaaaaagc aggcttcag    49

<210> SEQ ID NO 29
<211> LENGTH: 57
<212> TYPE: DNA
<213> ORGANISM: Artificial sequence
<220> FEATURE:
<223> OTHER INFORMATION: Description of the artificial sequence:
      oligonucleotide

<400> SEQUENCE: 29
agctctgaag cctgcttttt tatactaact tgagcggatg catggccact agtagct    57

<210> SEQ ID NO 30
<211> LENGTH: 29
<212> TYPE: DNA
<213> ORGANISM: Artificial sequence
<220> FEATURE:
<223> OTHER INFORMATION: Description of the artificial sequence:
      oligonucleotide

```
<400> SEQUENCE: 30
gcgtctagaa cagtatcgtg atgacagag                                    29

<210> SEQ ID NO 31
<211> LENGTH: 29
<212> TYPE: DNA
<213> ORGANISM: Artificial sequence
<220> FEATURE:
<223> OTHER INFORMATION: Description of the artificial sequence:
      oligonucleotide

<400> SEQUENCE: 31
gccaagctta gctttgcact ggattgcga                                    29

<210> SEQ ID NO 32
<211> LENGTH: 14
<212> TYPE: DNA
<213> ORGANISM: Artificial sequence
<220> FEATURE:
<223> OTHER INFORMATION: Description of the artificial sequence:
      oligonucleotide

<400> SEQUENCE: 32
aagaaaaaaa agaa                                                    14

<210> SEQ ID NO 33
<211> LENGTH: 36
<212> TYPE: DNA
<213> ORGANISM: Artificial sequence
<220> FEATURE:
<223> OTHER INFORMATION: Description of the artificial sequence:
      oligonucleotide

<400> SEQUENCE: 33
aaagatccgc gtcgactttg tgcttctctg gagtgc                            36

<210> SEQ ID NO 34
<211> LENGTH: 23
<212> TYPE: DNA
<213> ORGANISM: Artificial sequence
<220> FEATURE:
<223> OTHER INFORMATION: Description of the artificial sequence:
      oligonucleotide

<400> SEQUENCE: 34
aaacctagga aatcaaataa tga                                          23

<210> SEQ ID NO 35
<211> LENGTH: 47
<212> TYPE: DNA
<213> ORGANISM: Artificial sequence
<220> FEATURE:
<223> OTHER INFORMATION: Description of the artificial sequence:
      oligonucleotide

<400> SEQUENCE: 35
tcgagttctt tttttcttg aagcctgctt ttttactaac ttgagcg                 47

<210> SEQ ID NO 36
<211> LENGTH: 49
<212> TYPE: DNA
<213> ORGANISM: Artificial sequence
<220> FEATURE:
<223> OTHER INFORMATION: Description of the artificial sequence:
      oligonucleotide
```

<400> SEQUENCE: 36
agctcgctca agttagtata aaaaagcagg cttcaagaaa aaaagaac         49

<210> SEQ ID NO 37
<211> LENGTH: 30
<212> TYPE: DNA
<213> ORGANISM: Artificial sequence
<220> FEATURE:
<223> OTHER INFORMATION: Description of the artificial sequence:
      oligonucleotide

<400> SEQUENCE: 37
atcctaggtc attatttgat ttcaattttg                              30

<210> SEQ ID NO 38
<211> LENGTH: 40
<212> TYPE: DNA
<213> ORGANISM: Artificial sequence
<220> FEATURE:
<223> OTHER INFORMATION: Description of the artificial sequence:
      oligonucleotide

<400> SEQUENCE: 38
caatctagat ttctcgaggc ccgggctcat taggcacccc                   40

<210> SEQ ID NO 39
<211> LENGTH: 61
<212> TYPE: DNA
<213> ORGANISM: Artificial sequence
<220> FEATURE:
<223> OTHER INFORMATION: Description of the artificial sequence:
      oligonucleotide

<400> SEQUENCE: 39
ctaggataaa ccgatacaat taaaggctcc ttttggagcc ttttttttg gagaactagt    60 a                                                             61

<210> SEQ ID NO 40
<211> LENGTH: 61
<212> TYPE: DNA
<213> ORGANISM: Artificial sequence
<220> FEATURE:
<223> OTHER INFORMATION: Description of the artificial sequence:
      oligonucleotide

<400> SEQUENCE: 40
cgcgtactag ttctccaaaa aaaaaggctc caaaaggagc ctttaattgt atcggtttat    60
c                                                             61

<210> SEQ ID NO 41
<211> LENGTH: 23
<212> TYPE: DNA
<213> ORGANISM: Artificial sequence
<220> FEATURE:
<223> OTHER INFORMATION: Description of the artificial sequence:
      oligonucleotide

<400> SEQUENCE: 41
aaactcgagc aatgcttgca taa                                     23

<210> SEQ ID NO 42
<211> LENGTH: 23
<212> TYPE: DNA
<213> ORGANISM: Artificial sequence
<220> FEATURE:

-continued

```
<223> OTHER INFORMATION: Description of the artificial sequence:
      oligonucleotide

<400> SEQUENCE: 42
aaacatatgt tcactccatc caa                                              23

<210> SEQ ID NO 43
<211> LENGTH: 22
<212> TYPE: DNA
<213> ORGANISM: Artificial sequence
<220> FEATURE:
<223> OTHER INFORMATION: Description of the artificial sequence:
      oligonucleotide

<400> SEQUENCE: 43
aaaactagta tggcgattgc aa                                               22

<210> SEQ ID NO 44
<211> LENGTH: 22
<212> TYPE: DNA
<213> ORGANISM: Artificial sequence
<220> FEATURE:
<223> OTHER INFORMATION: Description of the artificial sequence:
      oligonucleotide

<400> SEQUENCE: 44
aaagaattcg cagtcaaacg cg                                               22

<210> SEQ ID NO 45
<211> LENGTH: 27
<212> TYPE: DNA
<213> ORGANISM: Artificial sequence
<220> FEATURE:
<223> OTHER INFORMATION: Description of the artificial sequence:
      oligonucleotide

<400> SEQUENCE: 45
aaaacatatg tacttgacac ttcagga                                          27

<210> SEQ ID NO 46
<211> LENGTH: 30
<212> TYPE: DNA
<213> ORGANISM: Artificial sequence
<220> FEATURE:
<223> OTHER INFORMATION: Description of the artificial sequence:
      oligonucleotide

<400> SEQUENCE: 46
atcctaggtc attatttgat ttcaattttg                                       30

<210> SEQ ID NO 47
<211> LENGTH: 12
<212> TYPE: DNA
<213> ORGANISM: Artificial sequence
<220> FEATURE:
<223> OTHER INFORMATION: Description of the artificial sequence:
      oligonucleotide

<400> SEQUENCE: 47 tcttttttc ct                                                           12

<210> SEQ ID NO 48
<211> LENGTH: 14
<212> TYPE: DNA
<213> ORGANISM: Artificial sequence
<220> FEATURE:
<223> OTHER INFORMATION: Description of the artificial sequence:
```

-continued oligonucleotide

<400> SEQUENCE: 48
ttcttttttt tctt                                                              14

<210> SEQ ID NO 49
<211> LENGTH: 25
<212> TYPE: DNA
<213> ORGANISM: Artificial sequence
<220> FEATURE:
<223> OTHER INFORMATION: Description of the artificial sequence:
      oligonucleotide

<400> SEQUENCE: 49
aaaggcgcca gcttaaaaaa aatcc                                                  25

<210> SEQ ID NO 50
<211> LENGTH: 20
<212> TYPE: DNA
<213> ORGANISM: Artificial sequence
<220> FEATURE:
<223> OTHER INFORMATION: Description of the artificial sequence:
      oligonucleotide

<400> SEQUENCE: 50
catacgtcat tattgacgtc                                                        20